(12) United States Patent
Betebenner et al.

(10) Patent No.: US 9,637,478 B2
(45) Date of Patent: May 2, 2017

(54) ANTIVIRAL COMPOUNDS AND USES THEREOF

(71) Applicant: AbbVie Inc., North Chicago, IL (US)

(72) Inventors: David A. Betebenner, Grayslake, IL (US); John K. Pratt, Kenosha, WI (US); David A. DeGoey, Salem, WI (US); Pamela L. Donner, Mundelein, IL (US); Charles A. Flentge, Salem, WI (US); Douglas K. Hutchinson, Newtown, CT (US); Warren M. Kati, Gurnee, IL (US); Allan C. Krueger, Gurnee, IL (US); Kenton L. Longenecker, Grayslake, IL (US); Clarence J. Maring, Palatine, IL (US); John T. Randolph, Libertyville, IL (US); Todd W. Rockway, Gurnee, IL (US); Michael D. Tufano, Chicago, IL (US); Rolf Wagner, Antioch, IL (US); Dachun Liu, Vernon Hills, IL (US)

(73) Assignee: AbbVie Inc., North Chicago, IL (US)

(*) Notice: Subject to any disclaimer, the term of this patent is extended or adjusted under 35 U.S.C. 154(b) by 0 days.

(21) Appl. No.: 15/141,556

(22) Filed: Apr. 28, 2016

(65) Prior Publication Data
US 2016/0368905 A1    Dec. 22, 2016

Related U.S. Application Data

(60) Continuation of application No. 14/260,504, filed on Apr. 24, 2014, now Pat. No. 9,353,091, which is a division of application No. 13/260,199, filed as application No. PCT/US2010/028560 on Mar. 25, 2010, now Pat. No. 8,748,443.

(60) Provisional application No. 61/163,155, filed on Mar. 25, 2009.

(51) Int. Cl.
| | |
|---|---|
| C07D 409/10 | (2006.01) |
| C07D 239/54 | (2006.01) |
| A61K 31/513 | (2006.01) |
| C07D 213/64 | (2006.01) |
| A61K 31/4418 | (2006.01) |
| C07C 311/08 | (2006.01) |
| A61K 31/18 | (2006.01) |
| C07D 233/72 | (2006.01) |
| A61K 31/4166 | (2006.01) |
| A61K 31/27 | (2006.01) |
| C07D 263/24 | (2006.01) |
| A61K 31/421 | (2006.01) |
| C07D 239/10 | (2006.01) |
| C07D 207/27 | (2006.01) |
| A61K 31/402 | (2006.01) |
| C07D 405/10 | (2006.01) |
| C07D 403/10 | (2006.01) |
| A61K 45/06 | (2006.01) |
| A61K 31/425 | (2006.01) |
| C07D 275/02 | (2006.01) |

(52) U.S. Cl.
CPC ............ *C07D 409/10* (2013.01); *A61K 31/18* (2013.01); *A61K 31/27* (2013.01); *A61K 31/402* (2013.01); *A61K 31/4166* (2013.01); *A61K 31/421* (2013.01); *A61K 31/425* (2013.01); *A61K 31/4418* (2013.01); *A61K 31/513* (2013.01); *A61K 45/06* (2013.01); *C07C 311/08* (2013.01); *C07D 207/27* (2013.01); *C07D 213/64* (2013.01); *C07D 233/72* (2013.01); *C07D 239/10* (2013.01); *C07D 239/54* (2013.01); *C07D 263/24* (2013.01); *C07D 275/02* (2013.01); *C07D 403/10* (2013.01); *C07D 405/10* (2013.01)

(58) Field of Classification Search
CPC ... C07C 275/30; C07C 275/32; C07C 275/40; C07C 275/42; C07C 233/65; C07C 233/67; C07C 233/76; C07C 233/81; C07C 49/303
See application file for complete search history.

(56) References Cited

U.S. PATENT DOCUMENTS

| | | | |
|---|---|---|---|
| 4,337,272 A | 6/1982 | Bernareggi et al. | |
| 4,927,835 A | 5/1990 | Kise et al. | |
| 7,067,535 B2 | 6/2006 | Takahashi et al. | |
| 8,158,631 B2 | 4/2012 | Chin et al. | |
| 8,158,803 B2 | 4/2012 | Lee et al. | |
| 8,178,547 B2 | 5/2012 | Steiner et al. | |
| 8,273,773 B2 | 9/2012 | Brameld et al. | |
| 2005/0176701 A1 | 8/2005 | Borchardt et al. | |

(Continued)

FOREIGN PATENT DOCUMENTS

| | | |
|---|---|---|
| DE | 2256313 | 5/1973 |
| DE | 2651750 | 5/1977 |

(Continued)

OTHER PUBLICATIONS

Liquid Crystals, 2008, 35 (11), pp. 1279-1292.

(Continued)

*Primary Examiner* — Alexander R Pagano
(74) *Attorney, Agent, or Firm* — Neal, Gerber & Eisenber LLP

(57) ABSTRACT

This invention relates to: (a) compounds and salts thereof that, inter alia, inhibit HCV; (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

26 Claims, No Drawings

(56) References Cited

U.S. PATENT DOCUMENTS

| | | |
|---|---|---|
| 2006/0270686 A1 | 11/2006 | Kelly et al. |
| 2007/0142640 A1 | 6/2007 | Arimoto et al. |
| 2008/0280891 A1 | 11/2008 | Kelly et al. |
| 2010/0021423 A1 | 1/2010 | Brameld et al. |
| 2010/0063027 A1 | 3/2010 | Okuno et al. |
| 2010/0158860 A1 | 6/2010 | Steiner et al. |
| 2010/0221211 A1 | 9/2010 | Furuyama et al. |
| 2010/0330032 A1 | 12/2010 | Chin et al. |
| 2012/0082646 A1 | 4/2012 | Betebenner et al. |

FOREIGN PATENT DOCUMENTS

| | | |
|---|---|---|
| DE | 2722383 | 12/1977 |
| EP | 1612211 A1 | 1/2006 |
| EP | 1953147 | 8/2008 |
| EP | 2017261 | 1/2009 |
| JP | H03215456 A | 9/1991 |
| JP | 2001519331 A | 10/2001 |
| JP | 2005539072 | 12/2005 |
| JP | 2006502112 A | 1/2006 |
| JP | 2006519844 | 8/2006 |
| JP | 2007291059 A | 11/2007 |
| JP | 2008515812 A | 5/2008 |
| JP | 2008540487 A | 11/2008 |
| JP | 2008540587 A | 11/2008 |
| JP | 2011528686 A | 11/2011 |
| JP | 2012513434 A | 6/2012 |
| RU | 2008129782 | 7/2008 |
| WO | WO9918074 A1 | 4/1999 |
| WO | WO03059872 A1 | 7/2003 |
| WO | WO2004005279 A2 | 1/2004 |
| WO | WO2004026815 | 4/2004 |
| WO | WO2004080971 | 9/2004 |
| WO | WO2006004107 | 1/2006 |
| WO | WO2006039718 A2 | 4/2006 |
| WO | WO2006120178 | 11/2006 |
| WO | WO2006122631 A1 | 11/2006 |
| WO | WO2007028135 A2 | 3/2007 |
| WO | WO2007081517 | 7/2007 |
| WO | WO2007125952 | 11/2007 |
| WO | WO2007125952 A1 | 11/2007 |
| WO | WO2008100867 | 8/2008 |
| WO | WO2008139984 | 11/2008 |
| WO | WO2009003998 A2 | 1/2009 |
| WO | WO2009007747 | 1/2009 |
| WO | WO2009054332 | 4/2009 |
| WO | WO2009073300 A1 | 6/2009 |
| WO | WO2010010017 A1 | 1/2010 |
| WO | WO2010072598 | 7/2010 |

OTHER PUBLICATIONS

Organic Electronics, 2008, 9(5), pp. 649-655.
CLEAN—Soil, Air, Water, 2007, 35 (5), pp. 433-437.
Macromolecular Chemistry and Physics, 2001, 202 (11), pp. 2367-2376.
Journal of Medicinal Chemistry, 1985, 28 (3), pp. 295-298.
Analytical Sciences, 1995, 11(2), pp. 195-201.
Synthesis, 1980, (6), pp. 483-484.
Journal of the American Chemical Society, 1953, 75, pp. 2635-2639.
Journal of Medicinal Chemistry, 2003, 46(4), pp. 453-456.
Journal of Medicinal Chemistry, 1997, 40 (6), pp. 942-951.
Journal of Organic Chemistry, 1997, 62 (17), pp. 5908-5919.
Journal of Medicinal Chemistry, vol. 29, No. 6, 1986, pp. 924-939.
Organic Letters, vol. 8, No. 17, 2006, pp. 3697-3700.
"Supporting Information" for Organic Letters, vol. 8, No. 17, 2006, pp. 3697-3700.
Beaulieu P.L., et al., "Recent Advances in the Development of NS5B Polymerase Inhibitors for the Treatment of Hepatitis C Virus Infection," Expert Opinion on Therapeutic Patents, 2009, vol. 19 (2), pp. 145-164.
Havelkova M.,et al., "Covalent Analogues of DNA . . . or 4-(purin-9-yl)benzenes," Tetrahedron, 2002, vol. 58 (37), pp. 7431-7435.
International Preliminary Report on Patentability and Written Opinion for Application No. PCT/US2010/028560, mailed on Sep. 27, 2011, 11 pages.
International Search Report for Application No. PCTIUS2010/028560, mailed on Feb. 23, 2011, 6 pages.
Pedrazzoli A.. et al.. "p-Acetylaminophenol Derivatives. II. Mannich Bases and 3-substituted 3,4-dihydro-2H-1.3-benzoxazines." Bollellino Chimico Farmaceutico, 1966, vol. 105 (7), pp. 503-511.
Stout D.M., et al., "Synthesis and Antiarrhythmic and Parasympatholytic Properties of Substituted Phenols. 1. Heteroarylamine Derivatives," Journal of Medicinal Chemistry, 1983, vol. 26 (6), pp. 808-813.
Stout D.M., et al., "Synthesis and Antiarrhythmic and Parasympatholytic Properties of Substituted Phenols. 3. Modifications to the Linkage Region (region 3)," Journal of Medicinal Chemistry, 1985, vol. 28 (3), pp. 295-298.
Suehiro T., "On the Rearrangement of 5-oxo-2 -methyl -4,4 -dibenzyl -3 -ethoxycarbonyl -4,5 -dihydro- indol catalyzed with Acid," Chemische Berichte, 1967, vol. 100 (3), pp. 915-918.
CAS Index of Registry No. 873437-44-6 (Entered STN Feb. 3, 2007).
CAPLUS Abstract w/Indexed Compound Hit of WO 2008139984 (2007) (Entered STN: Nov. 21, 2008).
CAPLUS Abstract w/Indexed Compound Hit of WO 2006004107 (2007) (Entered STN: Jan. 12, 2006).
L.M. Werbel et al., 29 Journal of Medicinal Chemistry, 924-939 (1986).

ANTIVIRAL COMPOUNDS AND USES THEREOF

CROSS-REFERENCE TO RELATED PATENT APPLICATIONS

This patent application is a continuation of U.S. patent application Ser. No. 14/260,504 filed Apr. 24, 2014 as a divisional of U.S. patent application Ser. No. 13/260,199 filed Dec. 9, 2011, now U.S. Pat. No. 8,748,443, which claims priority to PCT/US10/28560 filed on Mar. 25, 2010 which claims priority to U.S. Provisional Patent Application No. 61/163,155 filed Mar. 25, 2009. The entire contents of these applications are incorporated by reference into this patent application.

SEQUENCE LISTING

The instant application contains a Sequence Listing which has been submitted in ASCII format via EFS-Web and is hereby incorporated by reference in its entirety. Said ASCII copy, created on Apr. 28, 2016, is named 9861USC1_SEQ-LIST.txt, and is 1,206 bytes in size.

FIELD OF THE INVENTION

This invention is directed to: (a) compounds and salts thereof that, inter alia, are useful as hepatitis C virus (HCV) inhibitors; (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

BACKGROUND OF THE INVENTION

Hepatitis C is a blood-borne, infectious, viral disease that is caused by a hepatotropic virus called HCV. At least six different HCV genotypes (with several subtypes within each genotype) are known to date. In North America, HCV genotype 1a predominates, followed by HCV genotypes 1b, 2a, 2b, and 3a. In the United States, HCV genotypes 1, 2, and 3 are the most common, with about 80% of the hepatitis C patients having HCV genotype 1. In Europe, HCV genotype 1b is predominant, followed by HCV genotypes 2a, 2b, 2c, and 3a. HCV genotypes 4 and 5 are found almost exclusively in Africa. As discussed below, the patient's HCV genotype is clinically important in determining the patient's potential response to therapy and the required duration of such therapy.

An HCV infection can cause liver inflammation (hepatitis) that is often asymptomatic, but ensuing chronic hepatitis can result in cirrhosis of the liver (fibrotic scarring of the liver), liver cancer, and/or liver failure. The World Health Organization estimates that about 170 million persons worldwide are chronically infected with HCV, and from about three to about four million persons are newly infected globally each year. According to the Centers for Disease Control and Prevention, about four million people in the United States are infected with HCV. Co-infection with the human immunodeficiency virus (HIV) is common, and rates of HCV infection among HIV positive populations are higher.

There is a small chance of clearing the virus spontaneously, but the majority of patients with chronic hepatitis C will not clear it without treatment. Indications for treatment typically include proven HCV infection and persistent abnormal liver function tests. There are two treatment regimens that are primarily used to treat hepatitis C: monotherapy (using an interferon agent—either a "conventional" or longer-acting pegylated interferon) and combination therapy (using an interferon agent and ribavirin). Interferon, which is injected into the bloodstream, works by bolstering the immune response to HCV; and ribavirin, which is taken orally, is believed to work by preventing HCV replication. Taken alone, ribavirin does not effectively suppress HCV levels, but an interferon/ribavirin combination is more effective than interferon alone. Typically, hepatitis C is treated with a combination of pegylated interferon alpha and ribavirin for a period of 24 or 48 weeks, depending on the HCV genotype.

The goal of treatment is sustained viral response—meaning that HCV is not measurable in the blood after therapy is completed. Following treatment with a combination of pegylated interferon alpha and ribavirin, sustained cure rates (sustained viral response) of about 75% or better occur in people with HCV genotypes 2 and 3 in 24 weeks of treatment, about 50% in those with HCV genotype 1 with 48 weeks of treatment, and about 65% in those with HCV genotype 4 in 48 weeks of treatment.

Treatment may be physically demanding, particularly for those with prior history of drug or alcohol abuse, because both interferon and ribavirin have numerous side effects. Common interferon-associated side effects include flu-like symptoms, extreme fatigue, nausea, loss of appetite, thyroid problems, high blood sugar, hair loss, and skin reactions at the injection site. Possible serious interferon-associated side effects include psychoses (e.g., suicidal behavior), heart problems (e.g., heart attack, low blood pressure), other internal organ damage, blood problems (e.g., blood counts falling dangerously low), and new or worsening autoimmune disease (e.g., rheumatoid arthritis). Ribavirin-associated side effects include anemia, fatigue, irritability, skin rash, nasal stuffiness, sinusitis, and cough. Ribavirin can also cause birth defects, so pregnancy in female patients and female partners of male patients must be avoided during treatment and for six months afterward.

Some patients do not complete treatment because of the serious side effects discussed above; other patients (non-responders) continue to have measurable HCV levels despite treatment; and yet other patients (relapsers) "clear" the virus during therapy, but the virus returns sometime after completion of the treatment regimen. Thus, there continues to be a need for alternative compounds, compositions, and methods of treatment (used either in combination with or in lieu of an interferon agent and/or ribavirin) to alleviate the symptoms of hepatitis C, thereby providing partial or complete relief. This invention provides compounds (including salts thereof), compositions, and methods of treatment that generally address such a need.

SUMMARY OF THE INVENTION

This invention is directed to compounds that correspond in structure to formula (I):

(I)

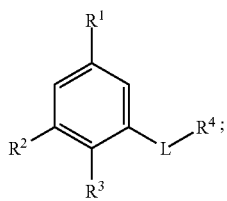

In formula (I):

R¹ is selected from the group consisting of:

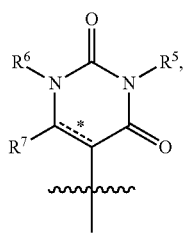 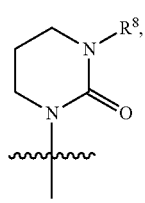

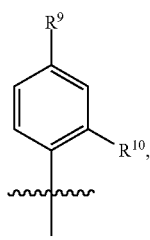 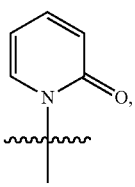

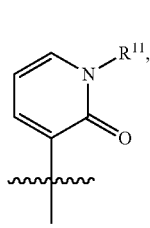 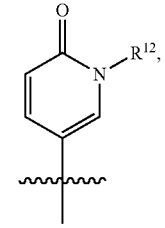

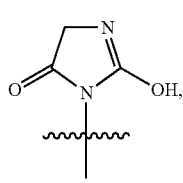

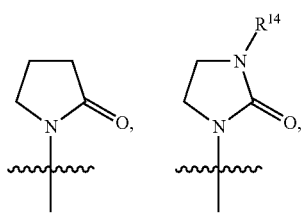

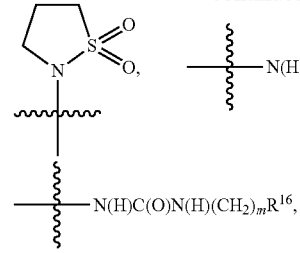

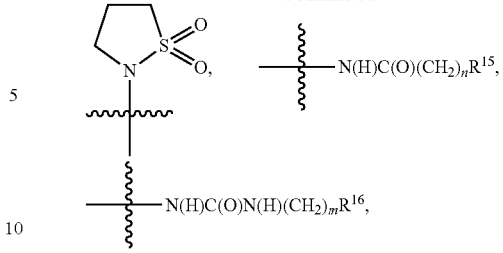

arylcarbonyl, and heteroarylcarbonyl;

--*-- is selected from the group consisting of single carbon-carbon bond and double carbon-carbon bond;

$R^5$, $R^6$, $R^8$, $R^{11}$, $R^{12}$, $R^{13}$, and $R^{14}$ are independently selected from the group consisting of hydrogen, methyl, and nitrogen-protecting group;

$R^7$ is selected from the group consisting of hydrogen and methyl;

$R^9$ is halo;

$R^{10}$ is halo;

n is selected from the group consisting of 1, 2, and 3;

$R^{15}$ is selected from the group consisting of hydrogen, amino, and nitrogen-protecting group substituted amino;

m is selected from the group consisting of 0, 1, 2, and 3;

$R^{16}$ is selected from the group consisting of hydrogen, aryl, alkyl, and alkyloxycarbonyl;

$R^2$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:

(a) the amino, aminocarbonyl, and aminosulfonyl optionally are substituted with:
(1) one or two substituents independently selected from the group consisting of alkyl, alkenyl, alkynyl, and alkylsulfonyl, or
(2) two substituents that, together with the amino nitrogen, form a single-ring heterocyclyl, and (b) the alkyl, alkenyl, alkynyl, alkyloxy, alkenyloxy, alkynyloxy, and alkylsulfonyl, optionally are substituted with one or more substituents independently selected from the group consisting of halo, oxo, nitro, cyano, azido, hydroxy, amino, alkyloxy, trimethylsilyl, carbocyclyl, and heterocyclyl, wherein:
the amino optionally is substituted with:
(1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
(2) two substituents that, together with the amino nitrogen, form a single-ring heterocyclyl, and (c) the carbocyclyl and heterocyclyl optionally are substituted with up to three substituents independently selected from the group consisting of alkyl, alkenyl, alkynyl, halo, oxo, nitro, cyano, azido, hydroxy, amino, alkyloxy, trimethylsilyl, carbocyclyl, and heterocyclyl, wherein:
the amino optionally is substituted with:
(1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
(2) two substituents that, together with the amino nitrogen, form a single-ring heterocyclyl;

$R^3$ is selected from the group consisting of hydrogen, hydroxy, alkyl, alkenyl, alkynyl, alkyloxy, alkenyloxy, alkynyloxy, alkylsulfonyloxy, amino, carbocyclylsulfonyloxy, haloalkylsulfonyloxy, and halo;

as to L and $R^4$:

L is a bond, and $R^4$ is selected from the group consisting of $C_5$-$C_6$-carbocyclyl, fused 2-ring carbocyclyl and fused 2-ring heterocyclyl, wherein each such substituent optionally is substituted with one or more substituents independently selected from the group consisting of $R^E$, $R^F$, $R^G$, $R^H$, $R^I$, $R^J$, and $R^K$, or L is selected from the group consisting of $C(R^A)$=$C(R^B)$, C≡C, $C(O)N(R^C)$, $N(R^D)C(O)$, $C_1$-$C_2$-alkylene, $CH_2O$, $OCH_2$, cyclopropyl-1,2-ene, $CH_2N(R^L)$, $N(R^M)CH_2$, $C(O)CH_2$, and $CH_2C(O)$, and $R^4$ is selected from the group consisting of $C_5$-$C_6$-carbocyclyl and 5-6-membered heterocyclyl, wherein each such substituent optionally is substituted with one or more substituents independently selected from the group consisting of $R^E$, $R^F$, $R^G$, $R^H$, $R^I$, $R^J$, and $R^K$;

$R^A$, $R^B$, $R^L$, and $R^M$ are independently selected from the group consisting of hydrogen, $C_1$-$C_6$-alkyl, $C_1$-$C_6$-alkyloxy, $C_3$-$C_8$-cycloalkyl, and halo, wherein:

the $C_1$-$C_6$-alkyl optionally is substituted with one or more substituents independently selected from the group consisting of carboxy, halo, hydroxy, nitro, oxo, amino, cyano, alkyloxycarbonyl, alkylcarbonyloxy, alkyloxy, carbocyclyl, and heterocyclyl;

$R^C$ is selected from the group consisting of hydrogen and alkyl;

$R^D$ is selected from the group consisting of hydrogen and alkyl;

each $R^E$ is independently selected from the group consisting of halo, nitro, hydroxy, oxo, carboxy, cyano, amino, imino, azido, and aldehydo, wherein:

the amino optionally is substituted with one or two substituents independently selected from the group consisting of alkyl, alkenyl, and alkynyl;

each $R^F$ is independently selected from the group consisting of alkyl, alkenyl, and alkynyl, wherein:

each such substituent optionally is substituted with one or more substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:

the amino, imino, aminosulfonyl, aminocarbonyl, carbocyclyl, and heterocyclyl optionally are substituted with one or two substituents independently selected from the group consisting of alkyl, alkenyl, alkynyl, alkylsulfonyl, alkenylsulfonyl, alkynylsulfonyl, alkylsulfonylamino, hydroxy, and alkyloxy, wherein: amino portion of the alkylsulfonylamino optionally is substituted with a substituent selected from the group consisting of alkyl, alkenyl, and alkynyl;

each $R^G$ is independently selected from the group consisting of carbocyclyl and heterocyclyl, wherein:

each such substituent optionally is substituted with one or more substituents independently selected from the group consisting of alkyl, alkenyl, alkynyl, carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:

the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl;

each $R^H$ is independently selected from the group consisting of alkyloxy, alkenyloxy, alkynyloxy, alkylsulfonyloxy, alkenylsulfonyloxy, and alkynylsulfonyloxy, wherein:

each such substituent optionally is substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:

the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl;

each $R^I$ is independently selected from the group consisting of alkylcarbonyl, alkenylcarbonyl, alkynylcarbonyl, aminocarbonyl, alkyloxycarbonyl, carbocyclylcarbonyl, and heterocyclylcarbonyl, wherein:

(a) the alkylcarbonyl, alkenylcarbonyl, and alkynylcarbonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, and (b) the aminocarbonyl optionally is substituted with one or two substituents independently selected from the group consisting of alkyl, alkenyl, alkynyl, alkyloxyalkyl, carbocyclyl, heterocyclyl, alkylsulfonyl, and alkylsulfonylamino, wherein:

the carbocyclyl and heterocyclyl optionally are substituted with one or two substituents independently selected from the group consisting of halo, alkyl, and oxo;

each $R^J$ is independently selected from the group consisting of carbocyclylsulfonylamino, heterocyclylsulfonylamino, alkylcarbonylamino, alkenylcarbonylamino, alkynylcarbonylamino, alkyloxycarbonylamino, alkenyloxycarbonylamino, alkynyloxycarbonylamino, alkylsulfonylamino, alkenylsulfonylamino, alkynylsulfonylamino, aminocarbonylamino, alkyloxycarbonylaminoimino, alkylsulfonylaminoimino, alkenylsulfonylaminoimino, and alkynylsulfonylaminoimino, wherein:

(a) the amino portion of such substituents optionally is substituted with a substituent independently selected from the group consisting of carbocyclylalkyl, heterocyclylalkyl, alkylcarbonyloxy, aminocarbonylalkyl, alkyl, alkenyl, alkynyl, alkylcarbonyl, alkenylcarbonyl, alkynylcarbonyl, alkyloxycarbonyl, alkyloxyalkyloxycarbonyl, alkylcarbonyloxyalkyl, and alkylsulfonyl, wherein:

(1) the carbocyclyl portion of the carbocyclylalkyl and the heterocyclyl portion of the heterocyclylalkyl optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, oxo, and amino, and (2) the amino portion of the aminocarbonylalkyl optionally is substituted with one or two substituents independently selected from the group consisting of alkyl, alkenyl, and alkynyl, (b) the alkyl, alkenyl, and alkynyl portion of such substituents optionally is substituted with one or more substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:

the amino optionally is substituted with one or two substituents independently selected from the group consisting of alkyl, alkenyl, alkynyl, alkyloxy, alkenyloxy, and alkynyloxy, wherein:

the alkyl optionally is substituted with one or more hydroxy;

(c) the carbocyclyl and heterocyclyl portions of such substituents optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, and amino, wherein:

the amino optionally is substituted with one or two substituents independently selected from the group consisting of alkyl, alkenyl, and alkynyl; and each $R^K$ is independently selected from the group consisting of aminosulfonyl, alkylsulfonyl, alkenylsulfonyl, and alkynylsulfonyl, wherein:

(a) the alkylsulfonyl, alkenylsulfonyl, and alkynylsulfonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:

the amino, aminosulfonyl, and aminocarbonyl optionally are substituted with one or two substituents independently selected from the group consisting of alkyl, alkenyl, and alkynyl; and (b) the aminosulfonyl optionally is substituted with one or two substituents independently selected from the group consisting of alkyl, alkenyl, and alkynyl.

This invention also is directed to the salts (including pharmaceutically acceptable salts) of the compounds of the invention.

This invention also is directed to compositions (including pharmaceutical compositions) that comprise one or more compounds and/or salts of the invention, and, optionally, one or more additional therapeutic agents.

This invention also is directed to kits that comprise one or more compounds and/or salts of the invention, and, optionally, one or more additional therapeutic agents.

This invention also is directed to methods of use of the compounds, salts, compositions, and/or kits of the invention to, for example, inhibit replication of an RNA virus (including HCV), treat a disease treatable by inhibiting HCV ribonucleic acid (RNA) polymerase (including hepatitis C).

This invention also is directed to a use of one or more compounds and/or salts of the invention to prepare a medicament. The medicament optionally can comprise one or more additional therapeutic agents. In some embodiments, the medicament is useful for treating hepatitis C.

Further benefits of Applicants' invention will be apparent to one skilled in the art from reading this patent application.

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

A. DEFINITIONS

The term "alkyl" (alone or in combination with another term(s)) means a straight- or branched-chain saturated hydrocarbyl substituent typically containing from 1 to about 20 carbon atoms, more typically from 1 to about 8 carbon atoms, and even more typically from 1 to about 6 carbon atoms. Examples of such substituents include methyl, ethyl, n-propyl, isopropyl, n-butyl, isobutyl, sec-butyl, tert-butyl, pentyl, iso-amyl, and hexyl. As in this definition, throughout this detailed description Applicants have provided illustrative examples. The provision of such illustrative examples should not be interpreted as if the provided illustrative examples are the only options available to one skilled in the art.

The term "alkenyl" (alone or in combination with another term(s)) means a straight- or branched-chain hydrocarbyl substituent containing one or more double bonds and typically from 2 to about 20 carbon atoms, more typically from about 2 to about 8 carbon atoms, and even more typically from about 2 to about 6 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl.

The term "alkynyl" (alone or in combination with another term(s)) means a straight- or branched-chain hydrocarbyl substituent containing one or more triple bonds and typically from 2 to about 20 carbon atoms, more typically from about 2 to about 8 carbon atoms, and even more typically from about 2 to about 6 carbon atoms. Examples of such substituents include ethynyl, 2-propynyl, 3-propynyl, 2-butynyl, and 3-butynyl.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single ring, which typically contains from 3 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl alternatively may be 2 or 3 rings fused together, such as naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 6 carbon ring atoms. Examples of single-ring cycloalkyls include cyclopropyl, cyclobutyl, cyclopentyl, and cyclohexyl. A cycloalkyl alternatively may be 2 or 3 carbon rings fused together, such as, decalinyl.

The term "aryl" (alone or in combination with another term(s)) means an aromatic carbocyclyl containing from 6 to 14 carbon ring atoms. Examples of aryls include phenyl, naphthalenyl, and indenyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

The term "hydrogen" (alone or in combination with another term(s)) means a hydrogen radical, and may be depicted as —H.

The term "hydroxy" (alone or in combination with another term(s)) means —OH.

The term "nitro" (alone or in combination with another term(s)) means —$NO_2$.

The term "cyano" (alone or in combination with another term(s)) means —CN, which also may be depicted as —C≡N.

The term "keto" (alone or in combination with another term(s)) means an oxo radical, and may be depicted as =O.

The term "carboxy" (alone or in combination with another term(s)) means —C(O)—OH.

The term "amino" (alone or in combination with another term(s)) means —$NH_2$.

The term "imino" (alone or in combination with another term(s)) means =NH.

The term "aminoimino" (alone or in combination with another term(s)) means =$NNH_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less.

Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—$NH_2$.

The term "oxy" (alone or in combination with another term(s)) means an ether substituent, and may be depicted as —O—.

The term "alkyloxy" or "alkoxy" (alone or in combination with another term(s)) means an alkylether substituent, i.e., —O-alkyl. Examples of such a substituent include methoxy (—O—$CH_3$), ethoxy, n-propoxy, isopropoxy, n-butoxy, isobutoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)— alkyl-$NH_2$.

The term "alkyloxycarbonyl" (alone or in combination with another term(s)) means —C(O)—O— alkyl.

The term "carbocyclylcarbonyl" (alone or in combination with another term(s)) means —C(O)— carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl alternatively may be 2 or 3 rings fused together, such as, for example, indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "2-fused ring" heterocyclyl (alone or in combination with another term(s)) means a saturated, partially saturated, or aryl heterocyclyl containing 2 fused rings. Examples of 2-fused-ring heterocyclyls include indolizinyl, quinolizinyl, purinyl, naphthyridinyl, pteridinyl, indolyl, isoindolyl, indoleninyl, isoindazolyl, phthalazinyl, quinoxalinyl, quinazolinyl, benzodiazinyl, benzopyranyl, benzothiopyranyl, benzoxazolyl, anthranilyl, benzodioxolyl, benzodioxanyl, benzoxadiazolyl, benzofuranyl, isobenzofuranyl, benzothiazolyl, benzothiadiazolyl, benzimidazolyl, benzotriazolyl, benzoxazinyl, and tetrahydroisoquinolinyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkoxyalkyl indicates that only the alkoxy component of the alkoxyalkyl substituent is substituted with one or more halogen radicals. If halogen substitution may alternatively or additionally occur on the alkyl component, the substituent would instead be described as "halogen-substituted alkoxyalkyl" rather than "haloalkoxyalkyl." And finally, if the halogen substitution may only occur on the alkyl component, the substituent would instead be described as "alkoxyhaloalkyl."

If substituents are described as being "independently selected" from a group, each substituent is selected independent of the other. Each substituent therefore may be identical to or different from the other substituent(s).

When words are used to describe a substituent, the rightmost-described component of the substituent is the component that has the free valence.

When a chemical formula is used to describe a substituent, the dash on the left side of the formula indicates the portion of the substituent that has the free valence.

When a chemical formula is used to describe a linking element between two other elements of a depicted chemical structure, the leftmost dash of the substituent indicates the portion of the substituent that is bound to the left element in the depicted structure. The rightmost dash, on the other hand, indicates the portion of the substituent that is bound to the right element in the depicted structure. To illustrate, if the depicted chemical structure is X-L-Y and L is described as —C(O)—NH—, then the chemical would be X—C(O)—NH—Y.

With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below.

ChemDraw software has been used to generate the compound names in this patent application.

The term "purity", unless otherwise qualified, means the chemical purity of a compound according to conventional HPLC assay.

B. COMPOUNDS

As discussed above, this invention is directed, in part, to compounds that correspond in structure to formula (I):

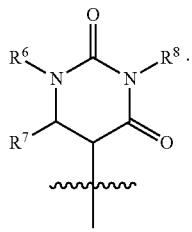

(I)

B1. Substituents $R^1$

In some embodiments, $R^1$ is:

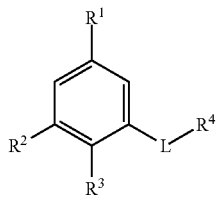

In these embodiments, the compounds correspond in structure to formula I-1:

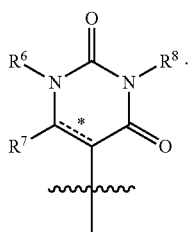

(I-1)

In some such embodiments, $R^1$ is:

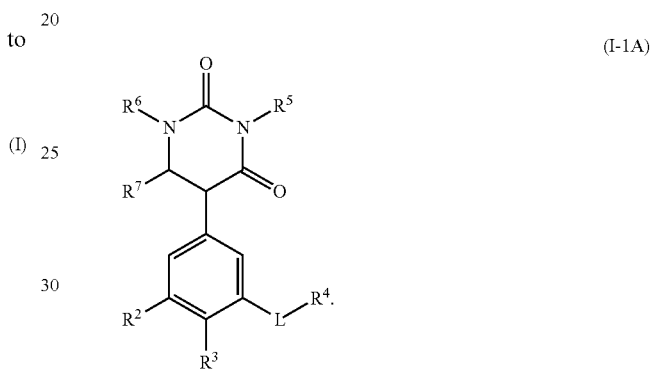

In these embodiments, the compounds correspond in structure to formula I-1A:

(I-1A)

In other such embodiments, $R^1$ is:

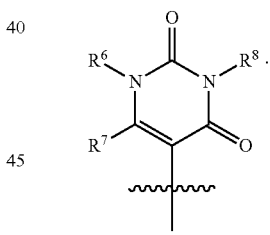

In these embodiments, the compounds correspond in structure to formula I-1B:

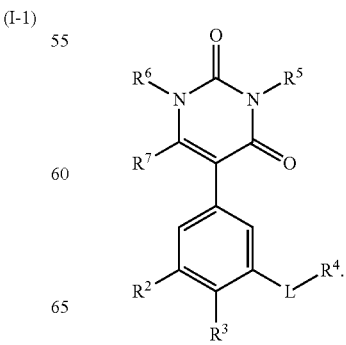

(I-1B)

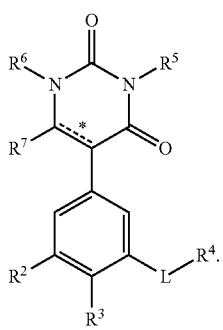

In some embodiments, $R^1$ is:

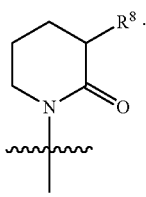
(I-2-1)

In these embodiments, the compounds correspond in structure to formula I-2:

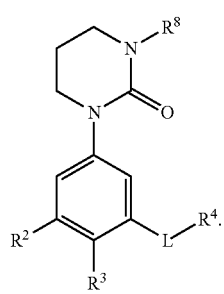
(I-2)

In some embodiments, $R^1$ is:

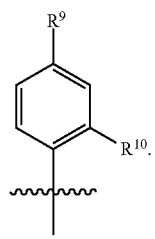

In these embodiments, the compounds correspond in structure to formula I-3:

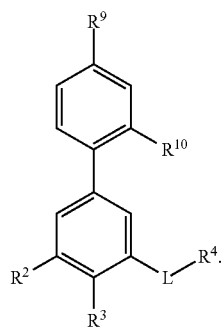
(I-3)

In some embodiments, $R^1$ is:

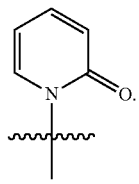
(I-4-1)

In these embodiments, the compounds correspond in structure to formula I-4:

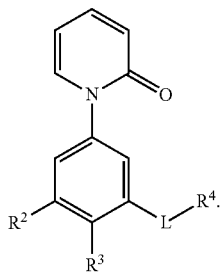
(I-4)

In some embodiments, $R^1$ is:

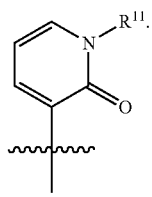

In these embodiments, the compounds correspond in structure to formula I-5:

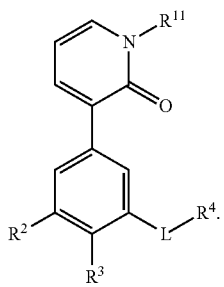
(I-5)

In some embodiments, $R^1$ is:

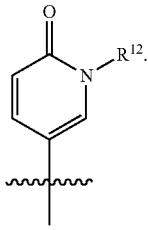
(I-6-1)

In these embodiments, the compounds correspond in structure to formula I-6:

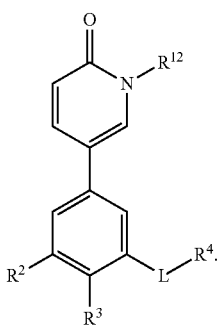
(I-6)

In some embodiments, $R^1$ is:

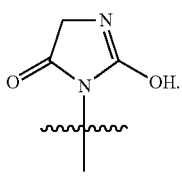 [SMILES: *N1C(=O)CN=C1O]

In these embodiments, the compounds correspond in structure to formula I-7:

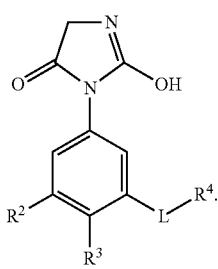
(I-7)

In some embodiments, $R^1$ is:

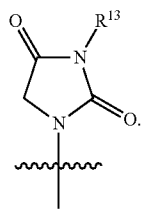

In these embodiments, the compounds correspond in structure to formula I-8:

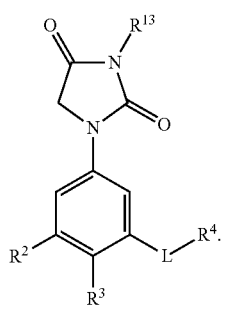
(I-8)

In some embodiments, $R^1$ is:

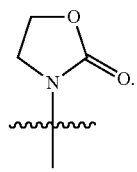 [SMILES: *N1CCOC1=O]

In these embodiments, the compounds correspond in structure to formula I-9:

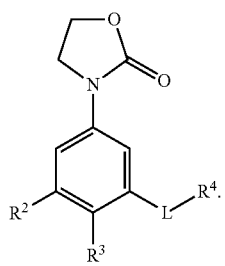
(I-9)

In some embodiments, $R^1$ is:

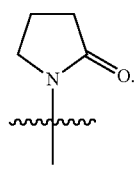 [SMILES: *N1CCCC1=O]

In these embodiments, the compounds correspond in structure to formula I-10:

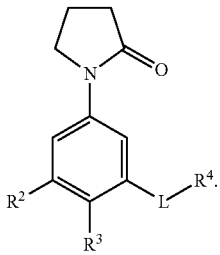
(I-10)

In some embodiments, $R^1$ is:

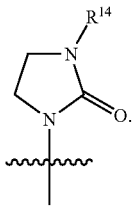

In these embodiments, the compounds correspond in structure to formula I-11:

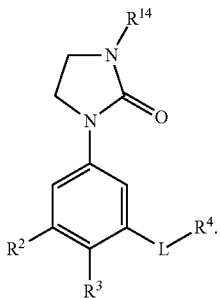
(I-11)

In some embodiments, $R^1$ is:

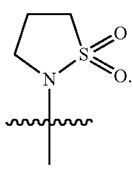 [SMILES: *N1CCCS1(=O)=O]

In these embodiments, the compounds correspond in structure to formula I-12:

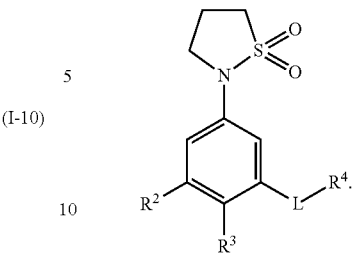
(I-12)

In some embodiments, $R^1$ is

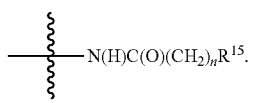

In some embodiments, $R^1$ is

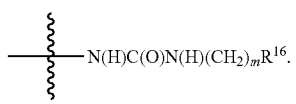

In some embodiments, $R^1$ is arylcarbonyl. In some such embodiments, $R^1$ is phenylcarbonyl.

In some embodiments, $R^1$ is heteroarylcarbonyl.

B2. Substituents $R^5$ $R^5$ is selected from the group consisting of hydrogen, methyl, and nitrogen-protecting group.

In some embodiments, $R^5$ is hydrogen.
In some embodiments, $R^5$ is methyl.
In some embodiments, $R^5$ is selected from the group consisting of hydrogen and methyl.
In some embodiments, $R^5$ is a nitrogen-protecting group. In these embodiments, the compounds are useful as intermediates for the preparation of compounds of formula (I). Nitrogen-protecting groups suitable for preparing compounds of formula (I) are known to those skilled in the art.

B3. Substituents $R^6$ $R^6$ is selected from the group consisting of hydrogen, methyl, and nitrogen-protecting group.

In some embodiments, $R^6$ is hydrogen.
In some embodiments, $R^6$ is methyl.
In some embodiments, $R^6$ is selected from the group consisting of hydrogen and methyl.
In some embodiments, $R^6$ is a nitrogen-protecting group. In these embodiments, the compounds are useful as intermediates for the preparation of compounds of formula (I). Nitrogen-protecting groups suitable for preparing compounds of formula (I) are known to those skilled in the art.

B4. Substituents $R^7$ $R^7$ is selected from the group consisting of hydrogen and methyl.

In some embodiments, $R^7$ is hydrogen.
In some embodiments, $R^7$ is methyl.

B5. Substituents $R^8$ $R^8$ is selected from the group consisting of hydrogen, methyl, and nitrogen-protecting group.

In some embodiments, $R^8$ is hydrogen.
In some embodiments, $R^8$ is methyl.
In some embodiments, $R^8$ is selected from the group consisting of hydrogen and methyl.
In some embodiments, $R^8$ is a nitrogen-protecting group. In these embodiments, the compounds are useful as intermediates for the preparation of compounds of formula (I). Nitrogen-protecting groups suitable for preparing compounds of formula (I) are known to those skilled in the art.

B6. Substituents $R^9$ $R^9$ is halo. In some such embodiments, $R^9$ is fluoro.

B7. Substituents $R^{10}$ $R^{10}$ is halo. In some such embodiments, $R^{10}$ is fluoro.

B8. Substituents $R^{11}$ $R^{11}$ is selected from the group consisting of hydrogen, methyl, and nitrogen-protecting group.

In some embodiments, $R^{11}$ is hydrogen.
In some embodiments, $R^{11}$ is methyl.
In some embodiments, $R^{11}$ is selected from the group consisting of hydrogen and methyl.
In some embodiments, $R^{11}$ is a nitrogen-protecting group. In these embodiments, the compounds are useful as intermediates for the preparation of compounds of formula (I). Nitrogen-protecting groups suitable for preparing compounds of formula (I) are known to those skilled in the art.

B9. Substituents $R^{12}$ $R^{12}$ is selected from the group consisting of hydrogen, methyl, and nitrogen-protecting group.

In some embodiments, $R^{12}$ is hydrogen.
In some embodiments, $R^{12}$ is methyl.
In some embodiments, $R^{12}$ is selected from the group consisting of hydrogen and methyl.
In some embodiments, $R^{12}$ is a nitrogen-protecting group. In these embodiments, the compounds are useful as intermediates for the preparation of compounds of formula (I). Nitrogen-protecting groups suitable for preparing compounds of formula (I) are known to those skilled in the art.

B10. Substituents $R^{13}$ $R^{13}$ is selected from the group consisting of hydrogen, methyl, and nitrogen-protecting group.

In some embodiments, $R^{13}$ is hydrogen.
In some embodiments, $R^{13}$ is methyl.
In some embodiments, $R^{13}$ is selected from the group consisting of hydrogen and methyl.
In some embodiments, $R^{13}$ is a nitrogen-protecting group. In these embodiments, the compounds are useful as intermediates for the preparation of compounds of formula (I). Nitrogen-protecting groups suitable for preparing compounds of formula (I) are known to those skilled in the art.

B11. Substituents $R^{14}$ $R^{14}$ is selected from the group consisting of hydrogen, methyl, and nitrogen-protecting group.

In some embodiments, $R^{14}$ is hydrogen.
In some embodiments, $R^{14}$ is methyl.
In some embodiments, $R^{14}$ is selected from the group consisting of hydrogen and methyl.
In some embodiments, $R^{14}$ is a nitrogen-protecting group. In these embodiments, the compounds are useful as intermediates for the preparation of compounds of formula (I). Nitrogen-protecting groups suitable for preparing compounds of formula (I) are known to those skilled in the art.

B12. Substituents $R^{15}$ $R^{15}$ is selected from the group consisting of hydrogen, amino, and nitrogen-protecting group substituted amino.

In some embodiments, $R^{15}$ is hydrogen.
In some embodiments, $R^{15}$ is amino.
In some embodiments, $R^{15}$ is a nitrogen-protecting group substituted amino. Nitrogen-protecting groups suitable for preparing compounds of formula (I) are known to those skilled in the art.

B13. Substituents $R^{16}$ $R^{16}$ is selected from the group consisting of hydrogen, aryl, alkyl, and alkyloxycarbonyl.

In some embodiments, $R^{16}$ is hydrogen.
In some embodiments, $R^{16}$ is aryl.
In some embodiments, $R^{16}$ is alkyl.
In some embodiments, $R^{16}$ is alkyloxycarbonyl.

B14. Substituent $R^2$ $R^2$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:
  (a) the amino, aminocarbonyl, and aminosulfonyl optionally are substituted with:
    (1) one or two substituents independently selected from the group consisting of alkyl, alkenyl, alkynyl, and alkylsulfonyl, or
    (2) two substituents that, together with the amino nitrogen, form a single-ring heterocyclyl,
  (b) the alkyl, alkenyl, alkynyl, alkyloxy, alkenyloxy, alkynyloxy, and alkylsulfonyl, optionally are substituted with one or more substituents independently selected from the group consisting of halo, oxo, nitro, cyano, azido, hydroxy, amino, alkyloxy, trimethylsilyl, carbocyclyl, and heterocyclyl, wherein:
    the amino optionally is substituted with:
    (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
    (2) two substituents that, together with the amino nitrogen, form a single-ring heterocyclyl, and
  (c) the carbocyclyl and heterocyclyl optionally are substituted with up to three substituents independently selected from the group consisting of alkyl, alkenyl, alkynyl, halo, oxo, nitro, cyano, azido, hydroxy, amino, alkyloxy, trimethylsilyl, carbocyclyl, and heterocyclyl, wherein:
    the amino optionally is substituted with:
    (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or (2) two substituents that, together with the amino nitrogen, form a single-ring heterocyclyl.

In some embodiments, $R^2$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:

the amino, aminocarbonyl, and aminosulfonyl optionally are substituted with:
 (1) one or two substituents independently selected from the group consisting of alkyl, alkenyl, alkynyl, and alkylsulfonyl, or
 (2) two substituents that, together with the amino nitrogen, form a single-ring heterocyclyl.

In some embodiments, $R^2$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:

the alkyl, alkenyl, alkynyl, alkyloxy, alkenyloxy, alkynyloxy, and alkylsulfonyl, optionally are substituted with one or more substituents independently selected from the group consisting of halo, oxo, nitro, cyano, azido, hydroxy, amino, alkyloxy, trimethylsilyl, carbocyclyl, and heterocyclyl, wherein:

the amino optionally is substituted with:
 (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
 (2) two substituents that, together with the amino nitrogen, form a single-ring heterocyclyl.

In some embodiments, $R^2$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:

the carbocyclyl and heterocyclyl optionally are substituted with up to three substituents independently selected from the group consisting of alkyl, alkenyl, alkynyl, halo, oxo, nitro, cyano, azido, hydroxy, amino, alkyloxy, trimethylsilyl, carbocyclyl, and heterocyclyl, wherein:

the amino optionally is substituted with:
 (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or
 (2) two substituents that, together with the amino nitrogen, form a single-ring heterocyclyl.

In some embodiments, $R^2$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:

(a) the amino, aminocarbonyl, and aminosulfonyl optionally are substituted with:
 (1) one or two substituents independently selected from the group consisting of alkyl, alkenyl, and alkynyl, or,
 (2) two substituents that, together with the amino nitrogen, form a single-ring heterocyclyl; and (b) the alkyl, alkenyl, alkynyl, alkyloxy, alkenyloxy, alkynyloxy, alkylsulfonyl, carbocyclyl, and heterocyclyl optionally are substituted with up to three substituents independently selected from the group consisting of halo, oxo, nitro, cyano, azido, hydroxy, amino, alkyloxy, carbocyclyl, and heterocyclyl, wherein the amino optionally is substituted with:
 (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or,
 (2) two substituents that, together with the amino nitrogen, form a single-ring heterocyclyl.

In some embodiments, $R^2$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:

the amino, aminocarbonyl, and aminosulfonyl optionally are substituted with:
 (1) one or two substituents independently selected from the group consisting of alkyl, alkenyl, and alkynyl, or,
 (2) two substituents that, together with the amino nitrogen, form a single-ring heterocyclyl.

In some embodiments, $R^2$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl, wherein:

the alkyl, alkenyl, alkynyl, alkyloxy, alkenyloxy, alkynyloxy, alkylsulfonyl, carbocyclyl, and heterocyclyl optionally are substituted with up to three substituents independently selected from the group consisting of halo, oxo, nitro, cyano, azido, hydroxy, amino, alkyloxy, carbocyclyl, and heterocyclyl, wherein the amino optionally is substituted with:
 (1) one or two substituents independently selected from the group consisting of alkyl, alkenyl, alkynyl, alkylcarbonyl, alkylsulfonyl, alkyloxycarbonyl, carbocyclyl, heterocyclyl, carbocyclylalkyl, and heterocyclylalkyl, or,
 (2) two substituents that, together with the amino nitrogen, form a single-ring heterocyclyl.

In some embodiments, $R^2$ is selected from the group consisting of halo, $C_1$-$C_4$-alkyl, $C_2$-$C_4$-alkenyl, $C_2$-$C_4$-alkynyl, amino, $C_1$-$C_4$-alkylsulfonyl, $C_3$-$C_6$-carbocyclyl, and 5-6-membered heterocyclyl, wherein:

(a) the amino optionally is substituted with one or two substituents independently selected from the group consisting of alkyl, alkenyl, alkynyl, and alkylsulfonyl, (b) the $C_1$-$C_4$-alkyl, $C_2$-$C_4$-alkenyl, and $C_2$-$C_4$-alkynyl optionally are substituted with one or more substituents independently selected from the group consisting of halo, oxo, hydroxy, alkyloxy, and trimethylsilyl, and (c) the $C_3$-$C_6$-carbocyclyl and 5-6-membered heterocyclyl optionally are substituted with up to three substituents independently selected from the group consisting of alkyl, alkenyl, alkynyl, halo, and amino, wherein:

the amino optionally is substituted with one or two substituents independently selected from the group consisting of alkyl, alkenyl, alkynyl, and alkylsulfonyl.

In some embodiments, $R^2$ is selected from the group consisting of $C_1$-$C_4$-alkyl, $C_2$-$C_4$-alkenyl, $C_2$-$C_4$-alkynyl, amino, $C_1$-$C_4$-alkylsulfonyl, $C_3$-$C_6$-carbocyclyl, and 5-6-membered heterocyclyl, wherein:

(a) the amino optionally is substituted with one or two substituents independently selected from the group consisting of alkyl, alkenyl, alkynyl, and alkylsulfonyl,
(b) the $C_1$-$C_4$-alkyl, $C_2$-$C_4$-alkenyl, and $C_2$-$C_4$-alkynyl optionally are substituted with one or more substituents independently selected from the group consisting of halo, oxo, hydroxy, alkyloxy, and trimethylsilyl, and
(c) the $C_3$-$C_6$-carbocyclyl and 5-6-membered heterocyclyl optionally are substituted with up to three substituents independently selected from the group consisting of alkyl, alkenyl, alkynyl, halo, and amino, wherein:
the amino optionally is substituted with one or two substituents independently selected from the group consisting of alkyl, alkenyl, alkynyl, and alkylsulfonyl.

In some embodiments, $R^2$ is selected from the group consisting of halo, $C_1$-$C_4$-alkyl, $C_3$-$C_6$-carbocyclyl, and 5-6-membered heterocyclyl, wherein:
(a) the $C_1$-$C_4$-alkyl optionally is substituted with up to three substituents independently selected from the group consisting of halo, oxo, hydroxy, alkyloxy, and trimethylsilyl, and
(b) the $C_3$-$C_6$-carbocyclyl and 5-6-membered heterocyclyl optionally are substituted with one or two substituents independently selected from the group consisting of alkyl, halo, and alkylsulfonylamino.

In some embodiments, $R^2$ is selected from the group consisting of halo, $C_1$-$C_4$-alkyl, $C_3$-$C_6$-carbocyclyl, and 5-6-membered heterocyclyl, wherein:
(a) the $C_1$-$C_4$-alkyl optionally is substituted with one or two substituents independently selected from the group consisting of halo, oxo, hydroxy, alkyloxy, and trimethylsilyl, and
(b) the $C_3$-$C_6$-carbocyclyl and 5-6-membered heterocyclyl optionally are substituted with a substituent selected from the group consisting of alkyl, halo, and alkylsulfonylamino.

In some embodiments, $R^2$ is selected from the group consisting of $C_1$-$C_4$-alkyl, $C_3$-$C_6$-carbocyclyl, and 5-6-membered heterocyclyl, wherein:
(a) the $C_1$-$C_4$-alkyl optionally is substituted with up to three substituents independently selected from the group consisting of halo, oxo, hydroxy, alkyloxy, and trimethylsilyl, and
(b) the $C_3$-$C_6$-carbocyclyl and 5-6-membered heterocyclyl optionally are substituted with one or two substituents independently selected from the group consisting of alkyl, halo, and alkylsulfonylamino.

In some embodiments, $R^2$ is selected from the group consisting of halo, tert-butyl, $C_3$-$C_6$-carbocyclyl, and 5-6-membered heterocyclyl, wherein:
the $C_3$-$C_6$-carbocyclyl and 5-6-membered heterocyclyl optionally are substituted with a substituent selected from the group consisting of alkyl, halo, and alkylsulfonylamino.

In some embodiments, $R^2$ is selected from the group consisting of tert-butyl, $C_3$-$C_6$-carbocyclyl, and 5-6-membered heterocyclyl, wherein:
the $C_3$-$C_6$-carbocyclyl and 5-6-membered heterocyclyl optionally are substituted with a substituent selected from the group consisting of alkyl, halo, and alkylsulfonylamino.

In some embodiments, $R^2$ is selected from the group consisting of halo, alkyl, haloalkyl, carboxyalkyl, hydroxyalkyl, alkyloxyalkyl, trimethylsilylalkynyl, alkylcarbocyclyl, carbocyclyl, alkylheterocyclyl, heterocyclyl, halocarbocyclyl, alkylsulfonylamino, and alkylsulfonyl.

In some embodiments, $R^2$ is selected from the group consisting of halo, alkyl, alkenyl, alkynyl, nitro, cyano, azido, alkyloxy, alkenyloxy, alkynyloxy, amino, aminocarbonyl, aminosulfonyl, alkylsulfonyl, carbocyclyl, and heterocyclyl.

In some embodiments, $R^2$ is selected from the group consisting of halo, $C_1$-$C_4$-alkyl, $C_2$-$C_4$-alkenyl, $C_2$-$C_4$-alkynyl, amino, $C_1$-$C_4$-alkylsulfonyl, $C_3$-$C_6$-carbocyclyl, and 5-6-membered heterocyclyl. In some such embodiment, $R^2$ is selected from the group consisting of halo, $C_1$-$C_4$-alkyl, $C_2$-$C_4$-alkenyl, $C_2$-$C_4$-alkynyl, amino, $C_1$-$C_4$-alkylsulfonyl, $C_6$-carbocyclyl, and 5-6-membered heterocyclyl. In other such embodiment, $R^2$ is selected from the group consisting of halo, $C_1$-$C_4$-alkyl, $C_2$-$C_4$-alkenyl, $C_2$-$C_4$-alkynyl, amino, $C_1$-$C_4$-alkylsulfonyl, phenyl, and 5-6-membered heteroaryl.

In some embodiments, $R^2$ is selected from the group consisting of $C_1$-$C_4$-alkyl, $C_2$-$C_4$-alkenyl, $C_2$-$C_4$-alkynyl, amino, $C_1$-$C_4$-alkylsulfonyl, $C_3$-$C_6$-carbocyclyl, and 5-6-membered heterocyclyl. In some such embodiment, $R^2$ is selected from the group consisting of $C_1$-$C_4$-alkyl, $C_2$-$C_4$-alkenyl, $C_2$-$C_4$-alkynyl, amino, $C_1$-$C_4$-alkylsulfonyl, $C_6$-carbocyclyl, and 5-6-membered heterocyclyl. In other such embodiment, $R^2$ is selected from the group consisting of $C_1$-$C_4$-alkyl, $C_2$-$C_4$-alkenyl, $C_2$-$C_4$-alkynyl, amino, $C_1$-$C_4$-alkylsulfonyl, phenyl, and 5-6-membered heteroaryl.

In some embodiments, $R^2$ is selected from the group consisting of halo, $C_1$-$C_4$-alkyl, $C_3$-$C_6$-carbocyclyl, and 5-6-membered heterocyclyl. In some such embodiments, $R^2$ is selected from the group consisting of halo, $C_1$-$C_4$-alkyl, $C_6$-carbocyclyl, and 5-6-membered heterocyclyl. In other such embodiments, $R^2$ is selected from the group consisting of halo, $C_1$-$C_4$-alkyl, phenyl, and 5-6-membered heteroaryl.

In some embodiments, $R^2$ is selected from the group consisting of $C_1$-$C_4$-alkyl, $C_3$-$C_6$-carbocyclyl, and 5-6-membered heterocyclyl. In some such embodiments, $R^2$ is selected from the group consisting of $C_1$-$C_4$-alkyl, $C_6$-carbocyclyl, and 5-6-membered heterocyclyl. In other such embodiments, $R^2$ is selected from the group consisting of $C_1$-$C_4$-alkyl, phenyl, and 5-6-membered heteroaryl.

In some embodiments, $R^2$ is selected from the group consisting of halo, tert-butyl, $C_3$-$C_6$-carbocyclyl, and 5-6-membered heterocyclyl. In some such embodiments, $R^2$ is selected from the group consisting of halo, tert-butyl, $C_6$-carbocyclyl, and 5-6-membered heterocyclyl. In other such embodiments, $R^2$ is selected from the group consisting of halo, tert-butyl, phenyl, and 5-6-membered heteroaryl.

In some embodiments, $R^2$ is selected from the group consisting of tert-butyl, $C_3$-$C_6$-carbocyclyl, and 5-6-membered heterocyclyl. In some such embodiments, $R^2$ is selected from the group consisting of tert-butyl, $C_6$-carbocyclyl, and 5-6-membered heterocyclyl. In other such embodiments, $R^2$ is selected from the group consisting of tert-butyl, phenyl, and 5-6-membered heteroaryl.

In some embodiments, $R^2$ is selected from the group consisting of $C_3$-$C_6$-carbocyclyl and 5-6-membered heterocyclyl. In some such embodiments, $R^2$ is selected from the group consisting of $C_6$-carbocyclyl, and 5-6-membered heterocyclyl. In other such embodiments, $R^2$ is selected from the group consisting of phenyl and 5-6-membered heteroaryl.

In some embodiments, $R^2$ is selected from the group consisting of $C_3$-$C_6$-carbocyclyl and 5-6-membered heterocyclyl. In some such embodiments, $R^2$ is selected from the group consisting of $C_6$-carbocyclyl, and 5-6-membered heterocyclyl. In other such embodiments, $R^2$ is selected from the group consisting of phenyl, furanyl, pyrazolyl, and thiophenyl.

Suitable carbocyclyls for the above embodiments include, for example, cyclopropyl and phenyl.

Suitable heterocyclyls for the above embodiments include, for example, furanyl, pyrazolyl, and thiophenyl.

In some embodiments, $R^2$ is selected from the group consisting of halo, alkyl, and alkyloxy.

In some embodiments, $R^2$ is alkyl.

In some embodiments, $R^2$ is tert-butyl.

B15. Substituent $R^3$ $R^3$ is selected from the group consisting of hydrogen, hydroxy, alkyl, alkenyl, alkynyl, alkyloxy, alkenyloxy, alkynyloxy, alkylsulfonyloxy, amino, carbocyclylsulfonyloxy, haloalkylsulfonyloxy, and halo.

In some embodiments, $R^3$ is selected from the group consisting of hydrogen, hydroxy, alkyloxy, and halo. In some such embodiments, $R^3$ is selected from the group consisting of hydrogen, hydroxy, alkyloxy, and fluoro. In other such embodiments, $R^3$ is selected from the group consisting of hydrogen, hydroxy, alkyloxy, and fluoro. In yet other such embodiments, $R^3$ is selected from the group consisting of hydrogen, hydroxy, alkyloxy, and chloro. In yet other such embodiments, $R^3$ is selected from the group consisting of hydrogen, hydroxy, alkyloxy, and bromo. In further such embodiments, $R^3$ is selected from the group consisting of hydrogen, hydroxy, alkyloxy, and iodo.

In some embodiments, $R^3$ is selected from the group consisting of hydrogen, hydroxy, methoxy, and halo. In some such embodiments, $R^3$ is selected from the group consisting of hydrogen, hydroxy, methoxy, and fluoro. In other such embodiments, $R^3$ is selected from the group consisting of hydrogen, hydroxy, methoxy, and chloro. In yet other such embodiments, $R^3$ is selected from the group consisting of hydrogen, hydroxy, methoxy, and bromo. In further such embodiments, $R^3$ is selected from the group consisting of hydrogen, hydroxy, methoxy, and iodo.

In some embodiments, $R^3$ is selected from the group consisting of hydrogen, hydroxy, and alkyloxy. In some such embodiments, $R^3$ is selected from the group consisting of hydrogen, hydroxy, methoxy, and ethoxy.

In some embodiments, $R^3$ is selected from the group consisting of hydrogen, amino, alkyl, and alkenyl. In some such embodiments, $R^3$ is selected from the group consisting of hydrogen, methyl, ethyl, ethenyl, and amino.

In some embodiments, $R^3$ is s hydrogen.

In some embodiments, $R^3$ is hydroxy.

In some embodiments, $R^3$ is amino.

In some embodiments, $R^3$ is halo.

In some embodiments, $R^3$ is iodo.

In some embodiments, $R^3$ is alkenyl.

In some embodiments, $R^3$ is ethenyl.

In some embodiments, $R^3$ is alkyl.

In some embodiments, $R^3$ is methyl.

In some embodiments, $R^3$ is ethyl.

In some embodiments, $R^3$ is alkyloxy.

In some embodiments, $R^3$ is methoxy.

In some embodiments, $R^3$ is ethoxy.

B16. Substituent L

L is selected from the group consisting of bond, $C(R^A)=C(R^B)$, $C\equiv C$, $C(O)N(R^C)$, $N(R^D)C(O)$, $C_1$-$C_2$-alkylene, $CH_2O$, $OCH_2$, cyclopropyl-1,2-ene, $CH_2N(R^L)$, $N(R^M)CH_2$, $C(O)CH_2$, and $CH_2C(O)$, wherein $R^A$, $R^B$, $R^C$, $R^D$, $R^L$, and $R^M$ are as discussed below.

In some embodiments, L is selected from the group consisting of bond, $C(R^A)=C(R^B)$, $C\equiv C$, $C(O)N(R^C)$, $N(R^D)C(O)$, $C_1$-$C_2$-alkylene, $CH_2O$, $OCH_2$, cyclopropyl-1,2-ene, $CH_2N(R^L)$, and $N(R^M)CH_2$.

In some embodiments, L is selected from the group consisting of $C(R^A)=C(R^B)$, ethylene, and cyclopropyl-1,2-ene.

In some embodiments, L is selected from the group consisting of $C(R^A)=C(R^B)$, $C\equiv C$, $C(O)N(R^C)$, $N(R^D)C(O)$, $C_1$-$C_2$-alkylene, $CH_2O$, $OCH_2$, cyclopropyl-1,2-ene, $CH_2N(R^L)$, $N(R^M)CH_2$, $C(O)CH_2$, and $CH_2C(O)$.

In some embodiments, L is selected from the group consisting of $C\equiv C$, $C(O)N(R^C)$, $N(R^D)C(O)$, $CH_2O$, $OCH_2$, $CH_2N(R^L)$, and $N(R^M)CH_2$.

In some embodiments, L is a bond. In these embodiments, the compounds of formula (I) correspond in structure to formula I-L0:

(I-L0)

In some embodiments, L is $C(R^A)=C(R^B)$, wherein $R^A$ and $R^B$ are as discussed below. In these embodiments, the compounds of formula (I) correspond in structure to formula I-L1:

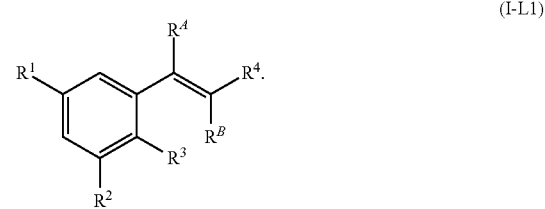

(I-L1)

In some embodiments, L is $C\equiv C$. In these embodiments, the compounds of formula (I) correspond in structure to formula I-L2:

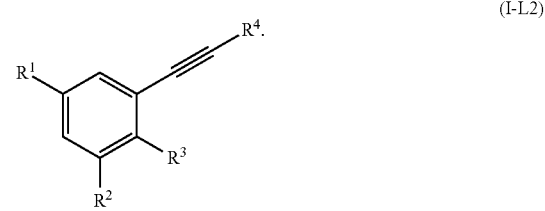

(I-L2)

In some embodiments, L is $C(O)N(R^C)$, wherein $R^C$ is as discussed below. In these embodiments, the compounds of formula (I) correspond in structure to formula I-L3:

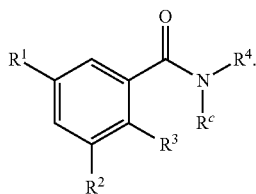
(I-L3)

In some embodiments, L is N(R$^D$)C(O), wherein R$^D$ is as discussed below. In these embodiments, the compounds of formula (I) correspond in structure to formula I-L4:

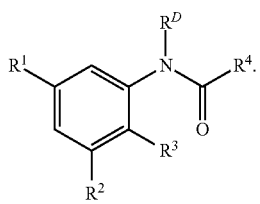
(I-L4)

In some embodiments, L is C$_1$-C$_2$-alkylene. In these embodiments, the compounds of formula (I) correspond in structure to formula I-L5-1 (if L is methylene) or I-L5-2 (if L is ethylene):

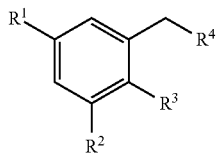
(I-L5-1)

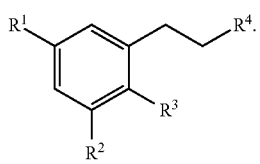
(I-L5-2)

In some embodiments, L is CH$_2$O. In these embodiments, the compounds of formula (I) correspond in structure to formula I-L6:

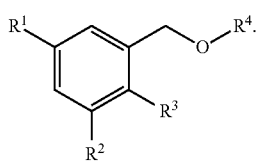
(I-L6)

In some embodiments, L is OCH$_2$. In these embodiments, the compounds of formula (I) correspond in structure to formula I-L7:

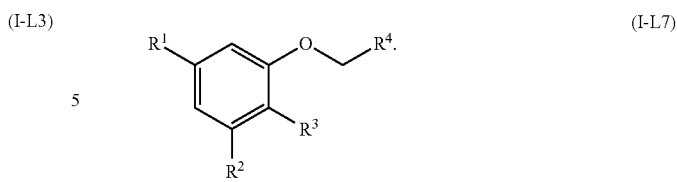
(I-L7)

In some embodiments, L is cyclopropyl-1,2-ene. In these embodiments, the compounds of formula (I) correspond in structure to formula I-L8:

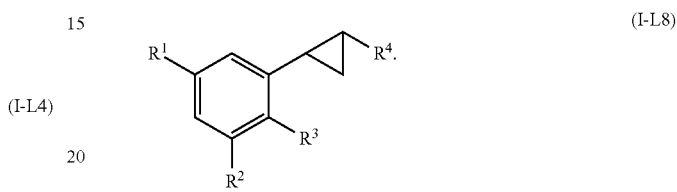
(I-L8)

In some embodiments, L is C(H)$_2$N(R$^L$). In these embodiments, the compounds of formula (I) correspond in structure to formula I-L9:

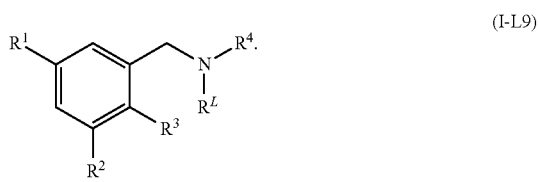
(I-L9)

In some embodiments, L is N(R$^M$)C(H)$_2$. In these embodiments, the compounds of formula (I) correspond in structure to formula I-L10:

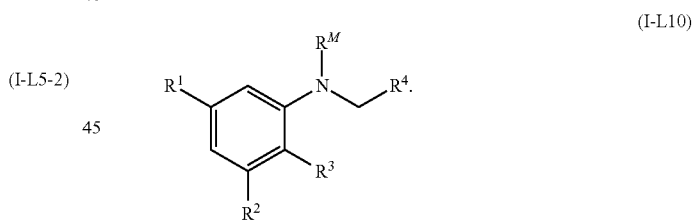
(I-L10)

In some embodiments, L is C(O)CH$_2$. In these embodiments, the compounds of formula (I) correspond in structure to formula I-L11:

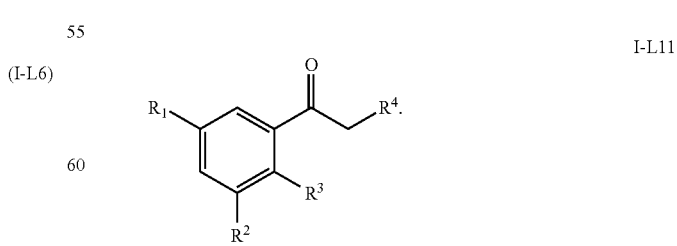
I-L11

In some embodiments, L is CH$_2$C(O). In these embodiments, the compounds of formula (I) correspond in structure to formula I-L12:

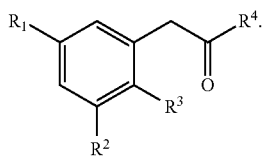

I-L12

B17. Substituents $R^A$ and $R^B$ $R^A$ and $R^B$ are independently selected from the group consisting of hydrogen, $C_1$-$C_6$-alkyl, $C_1$-$C_6$-alkyloxy, $C_3$-$C_8$-cycloalkyl, and halo, wherein:

the $C_1$-$C_6$-alkyl optionally is substituted with one or more substituents independently selected from the group consisting of carboxy, halo, hydroxy, nitro, oxo, amino, cyano, alkyloxycarbonyl, alkylcarbonyloxy, alkyloxy, carbocyclyl, and heterocyclyl.

In some embodiments, one of $R^A$ and $R^B$ is hydrogen, and the other is selected from the group consisting of $C_1$-$C_6$-alkyl, $C_1$-$C_6$-alkyloxy, $C_3$-$C_8$-cycloalkyl, and halo, wherein:

the $C_1$-$C_6$-alkyl optionally is substituted with one or more substituents independently selected from the group consisting of carboxy, halo, hydroxy, nitro, oxo, amino, cyano, alkyloxycarbonyl, alkylcarbonyloxy, alkyloxy, carbocyclyl, and heterocyclyl.

In some embodiments, $R^A$ and $R^B$ are independently selected from the group consisting of hydrogen, $C_1$-$C_6$-alkyl, $C_1$-$C_6$-alkyloxy, $C_3$-$C_8$-cycloalkyl, and halo.

In some of the above embodiments, $R^A$ is hydrogen. In other of the above embodiments, $R^B$ is hydrogen.

In some embodiment, one of $R^A$ and $R^B$ is hydrogen, and the other is selected from the group consisting of hydrogen, methyl, methoxy, and halo.

In some embodiments, $R^A$ is hydrogen, and $R^B$ is selected from the group consisting of methyl, methoxy, and halo. In some such embodiments, $R^B$ is selected from the group consisting of methyl, methoxy, and fluoro. In other such embodiments, $R^B$ is selected from the group consisting of methyl, methoxy, and chloro. In yet other such embodiments, $R^B$ is selected from the group consisting of methyl, methoxy, and bromo. In further such embodiments, $R^B$ is selected from the group consisting of methyl, methoxy, and iodo. In yet further such embodiments, $R^B$ is selected from the group consisting of methyl, methoxy, chloro, and fluoro.

In some embodiments, $R^B$ is hydrogen, and $R^A$ is selected from the group consisting of methyl, methoxy, and halo. In some such embodiments, $R^A$ is selected from the group consisting of methyl, methoxy, and fluoro. In other such embodiments, $R^A$ is selected from the group consisting of methyl, methoxy, and chloro. In yet other such embodiments, $R^A$ is selected from the group consisting of methyl, methoxy, and bromo. In further such embodiments, $R^A$ is selected from the group consisting of methyl, methoxy, and iodo. In yet further such embodiments, $R^A$ is selected from the group consisting of methyl, methoxy, chloro, and fluoro.

In some embodiments, $R^A$ is hydrogen, and $R^B$ is hydrogen.

B18. Substituent $R^C$ $R^C$ is selected from the group consisting of hydrogen and alkyl. In some such embodiments, $R^C$ is selected from the group consisting of hydrogen and methyl.

In some embodiments, $R^C$ is hydrogen.

In some embodiments, $R^C$ is alkyl. In some such embodiments, $R^C$ is methyl.

B19. Substituent $R^D$ $R^D$ is selected from the group consisting of hydrogen and alkyl. In some such embodiments, $R^D$ is selected from the group consisting of hydrogen and methyl.

In some embodiments, $R^D$ is hydrogen.

In some embodiments, $R^D$ is alkyl. In some such embodiments, $R^D$ is methyl.

B20. Substituent $R^L$ $R^L$ is selected from the group consisting of hydrogen, $C_1$-$C_6$-alkyl, $C_1$-$C_6$-alkyloxy, $C_3$-$C_8$-cycloalkyl, and halo, wherein:

the $C_1$-$C_6$-alkyl optionally is substituted with one or more substituents independently selected from the group consisting of carboxy, halo, hydroxy, nitro, oxo, amino, cyano, alkyloxycarbonyl, alkylcarbonyloxy, alkyloxy, carbocyclyl, and heterocyclyl.

In some embodiments, $R^L$ is selected from the group consisting of hydrogen, $C_1$-$C_6$-alkyl, $C_1$-$C_6$-alkyloxy, $C_3$-$C_8$-cycloalkyl, and halo.

In some embodiments, $R^L$ is selected from the group consisting of hydrogen, $C_1$-$C_6$-alkyl, $C_1$-$C_6$-alkyloxy, and halo, wherein:

the $C_1$-$C_6$-alkyl optionally is substituted with one or more substituents independently selected from the group consisting of carboxy, halo, hydroxy, nitro, oxo, amino, cyano, alkyloxycarbonyl, alkylcarbonyloxy, alkyloxy, carbocyclyl, and heterocyclyl.

In some embodiments, $R^L$ is selected from the group consisting of hydrogen, $C_1$-$C_6$-alkyl, $C_1$-$C_6$-alkyloxy, and halo.

In some of the above embodiments, $R^L$ is halo. In some such embodiments, the halo is fluoro. In other such embodiments, the halo is chloro. In yet other such embodiments, the halo is bromo. In further such embodiments, the halo is iodo.

In some of the above embodiments, $R^L$ is hydrogen.

In some of the above embodiments, $R^L$ is $C_1$-$C_6$-alkyl.

In some of the above embodiments, $R^L$ is $C_1$-$C_6$-alkyloxy.

B21. Substituent $R^M$ $R^M$ is selected from the group consisting of hydrogen, $C_1$-$C_6$-alkyl, $C_1$-$C_6$-alkyloxy, $C_3$-$C_8$-cycloalkyl, and halo, wherein:

the $C_1$-$C_6$-alkyl optionally is substituted with one or more substituents independently selected from the group consisting of carboxy, halo, hydroxy, nitro, oxo, amino, cyano, alkyloxycarbonyl, alkylcarbonyloxy, alkyloxy, carbocyclyl, and heterocyclyl.

In some embodiments, $R^M$ is selected from the group consisting of hydrogen, $C_1$-$C_6$-alkyl, $C_1$-$C_6$-alkyloxy, $C_3$-$C_8$-cycloalkyl, and halo.

In some embodiments, $R^M$ is selected from the group consisting of hydrogen, $C_1$-$C_6$-alkyl, $C_1$-$C_6$-alkyloxy, and halo, wherein:

the $C_1$-$C_6$-alkyl optionally is substituted with one or more substituents independently selected from the group consisting of carboxy, halo, hydroxy, nitro, oxo, amino, cyano, alkyloxycarbonyl, alkylcarbonyloxy, alkyloxy, carbocyclyl, and heterocyclyl.

In some embodiments, $R^M$ is selected from the group consisting of hydrogen, $C_1$-$C_6$-alkyl, $C_1$-$C_6$-alkyloxy, and halo.

In some of the above embodiments, $R^M$ is halo. In some such embodiments, the halo is fluoro. In other such embodiments, the halo is chloro. In yet other such embodiments, the halo is bromo. In further such embodiments, the halo is iodo.

In some of the above embodiments, $R^M$ is hydrogen.

In some of the above embodiments, $R^M$ is $C_1$-$C_6$-alkyl.

In some of the above embodiments, $R^M$ is $C_1$-$C_6$-alkyloxy.

B22. Substituent $R^4$ $R^4$ is selected from the group consisting of $C_5$-$C_6$-carbocyclyl, 5-6-membered heterocyclyl, fused 2-ring carbocyclyl, and fused 2-ring heterocyclyl, wherein each such substituent optionally is substituted with one or more substituents independently selected from the group consisting of $R^E$, $R^F$, $R^G$, $R^H$, $R^I$, $R^J$, and $R^K$, wherein $R^E$, $R^F$, $R^G$, $R^H$, $R^I$, $R^J$, and $R^K$ are as described below. In some such embodiments, the $C_5$-$C_6$-carbocyclyl, 5-6-membered heterocyclyl, fused 2-ring carbocyclyl, and fused 2-ring heterocyclyl are not substituted. In other such embodiments, the $C_5$-$C_6$-carbocyclyl, 5-6-membered heterocyclyl, fused 2-ring carbocyclyl, and fused 2-ring heterocyclyl are substituted with a substituent selected from the group consisting of $R^E$, $R^F$, $R^G$, $R^H$, $R^I$, $R^J$, and $R^K$. In other such embodiments, the $C_5$-$C_6$-carbocyclyl, 5-6-membered heterocyclyl, fused 2-ring carbocyclyl, and fused 2-ring heterocyclyl are substituted with a substituent selected from the group consisting of $R^E$, $R^F$, $R^I$, $R^J$, and $R^K$. In other such embodiments, the $C_5$-$C_6$-carbocyclyl, 5-6-membered heterocyclyl, fused 2-ring carbocyclyl, and fused 2-ring heterocyclyl are substituted with a substituent selected from the group consisting of $R^E$, $R^F$, and $R^J$. In other such embodiments, the $C_5$-$C_6$-carbocyclyl, 5-6-membered heterocyclyl, fused 2-ring carbocyclyl, and fused 2-ring heterocyclyl are substituted with a substituent selected from the group consisting of $R^F$ and $R^J$. In other such embodiments, the $C_5$-$C_6$-carbocyclyl, 5-6-membered heterocyclyl, fused 2-ring carbocyclyl, and fused 2-ring heterocyclyl are substituted with $R^J$. In yet other such embodiments, the $C_5$-$C_6$-carbocyclyl, 5-6-membered heterocyclyl, fused 2-ring carbocyclyl, and fused 2-ring heterocyclyl are substituted with two substituents independently selected from the group consisting of $R^E$, $R^F$, $R^G$, $R^H$, $R^I$, $R^J$, and $R^K$. In yet other such embodiments, the $C_5$-$C_6$-carbocyclyl, 5-6-membered heterocyclyl, fused 2-ring carbocyclyl, and fused 2-ring heterocyclyl are substituted with two substituents independently selected from the group consisting of $R^E$, $R^F$, $R^I$, $R^J$, and $R^K$. In yet other such embodiments, the $C_5$-$C_6$-carbocyclyl, 5-6-membered heterocyclyl, fused 2-ring carbocyclyl, and fused 2-ring heterocyclyl are substituted with two substituents independently selected from the group consisting of $R^E$, $R^F$, and $R^J$. In yet other such embodiments, the $C_5$-$C_6$-carbocyclyl, 5-6-membered heterocyclyl, fused 2-ring carbocyclyl, and fused 2-ring heterocyclyl are substituted with two substituents independently selected from the group consisting of $R^F$ and $R^J$. In further such embodiments, the $C_5$-$C_6$-carbocyclyl, 5-6-membered heterocyclyl, fused 2-ring carbocyclyl, and fused 2-ring heterocyclyl are substituted with three substituents independently selected from the group consisting of $R^E$, $R^F$, $R^G$, $R^H$, $R^I$, $R^J$, and $R^K$. In further such embodiments, the $C_5$-$C_6$-carbocyclyl, 5-6-membered heterocyclyl, fused 2-ring carbocyclyl, and fused 2-ring heterocyclyl are substituted with three substituents independently selected from the group consisting of $R^E$, $R^F$, $R^I$, $R^J$, and $R^K$. In further such embodiments, the $C_5$-$C_6$-carbocyclyl, 5-6-membered heterocyclyl, fused 2-ring carbocyclyl, and fused 2-ring heterocyclyl are substituted with three substituents independently selected from the group consisting of $R^E$, $R^F$, and $R^J$. In further such embodiments, the $C_5$-$C_6$-carbocyclyl, 5-6-membered heterocyclyl, fused 2-ring carbocyclyl, and fused 2-ring heterocyclyl are substituted with three substituents independently selected from the group consisting of $R^F$ and $R^J$. In further such embodiments, the $C_5$-$C_6$-carbocyclyl, 5-6-membered heterocyclyl, fused 2-ring carbocyclyl, and fused 2-ring heterocyclyl are substituted with one, two, or three substituents independently selected from the group consisting of $R^E$, $R^F$, $R^G$, $R^H$, $R^I$, $R^J$, and $R^K$. In further such embodiments, the $C_5$-$C_6$-carbocyclyl, 5-6-membered heterocyclyl, fused 2-ring carbocyclyl, and fused 2-ring heterocyclyl are substituted with one, two, or three substituents independently selected from the group consisting of $R^E$, $R^F$, $R^I$, $R^J$, and $R^K$. In further such embodiments, the $C_5$-$C_6$-carbocyclyl, 5-6-membered heterocyclyl, fused 2-ring carbocyclyl, and fused 2-ring heterocyclyl are substituted with one, two, or three substituents independently selected from the group consisting of $R^E$, $R^F$, and $R^J$. In further such embodiments, the $C_5$-$C_6$-carbocyclyl, 5-6-membered heterocyclyl, fused 2-ring carbocyclyl, and fused 2-ring heterocyclyl are substituted with one, two, or three substituents independently selected from the group consisting of $R^F$ and $R^J$.

In some embodiments, $R^4$ is selected from the group consisting of $C_5$-$C_6$-carbocyclyl and 5-6-membered heterocyclyl, wherein each such substituent optionally is substituted with one or more substituents independently selected from the group consisting of $R^E$, $R^F$, $R^G$, $R^H$, $R^I$, $R^J$, and $R^K$. In some such embodiments, the $C_5$-$C_6$-carbocyclyl and 5-6-membered heterocyclyl are not substituted. In other such embodiments, the $C_5$-$C_6$-carbocyclyl and 5-6-membered heterocyclyl are substituted with a substituent selected from the group consisting of $R^E$, $R^F$, $R^G$, $R^H$, $R^I$, $R^J$, and $R^K$. In yet other such embodiments, the $C_5$-$C_6$-carbocyclyl and 5-6-membered heterocyclyl are substituted with two substituents independently selected from the group consisting of $R^E$, $R^F$, $R^G$, $R^H$, $R^I$, $R^J$, and $R^K$. In further such embodiments, the $C_5$-$C_6$-carbocyclyl and 5-6-membered heterocyclyl are substituted with three substituents independently selected from the group consisting of $R^E$, $R^F$, $R^G$, $R^H$, $R^I$, $R^J$, and $R^K$. In further such embodiments, the $C_5$-$C_6$-carbocyclyl and 5-6-membered heterocyclyl are substituted with one, two, or three substituents independently selected from the group consisting of $R^E$, $R^F$, $R^G$, $R^H$, $R^I$, $R^J$, and $R^K$.

In some embodiments, $R^4$ is $C_5$-$C_6$-carbocyclyl optionally substituted with one or more substituents independently selected from the group consisting of $R^E$, $R^F$, $R^G$, $R^H$, $R^I$, $R^J$, and $R^K$. In some such embodiments, the $C_5$-$C_6$-carbocyclyl is not substituted. In other such embodiments, the $C_5$-$C_6$-carbocyclyl is substituted with a substituent selected from the group consisting of $R^E$, $R^F$, $R^G$, $R^H$, $R^I$, $R^J$, and $R^K$. In yet other such embodiments, the $C_5$-$C_6$-carbocyclyl is substituted with two substituents independently selected from the group consisting of $R^E$, $R^F$, $R^G$, $R^H$, $R^I$, $R^J$, and $R^K$. In further such embodiments, the $C_5$-$C_6$-carbocyclyl is substituted with three substituents independently selected from the group consisting of $R^E$, $R^F$, $R^G$, $R^H$, $R^I$, $R^J$, and $R^K$. In further such embodiments, the $C_5$-$C_6$-carbocyclyl is substituted with one, two, or three substituents independently selected from the group consisting of $R^E$, $R^F$, $R^G$, $R^H$, $R^I$, $R^J$, and $R^K$.

In some embodiments, $R^4$ is 5-6-membered heterocyclyl optionally substituted with one or more substituents independently selected from the group consisting of $R^E$, $R^F$, $R^G$, $R^H$, $R^I$, $R^J$, and $R^K$. In some such embodiments, the 5-6-membered heterocyclyl is not substituted. In other such embodiments, the 5-6-membered heterocyclyl is substituted with a substituent selected from the group consisting of $R^E$, $R^F$, $R^G$, $R^H$, $R^I$, $R^J$, and $R^K$. In yet other such embodiments, the 5-6-membered heterocyclyl is substituted with two substituents independently selected from the group consisting of $R^E$, $R^F$, $R^G$, $R^H$, $R^I$, $R^J$, and $R^K$. In further such embodiments, the 5-6-membered heterocyclyl is substituted with three substituents independently selected from the group consisting of $R^E$, $R^F$, $R^G$, $R^H$, $R^I$, $R^J$, and $R^K$. In further such embodiments, the 5-6-membered heterocyclyl is substituted with one, two, or three substituents independently selected from the group consisting of $R^E$, $R^F$, $R^G$, $R^H$, $R^I$, $R^J$, and $R^K$.

In some embodiments, $R^4$ is selected from the group consisting of fused 2-ring carbocyclyl and fused 2-ring heterocyclyl, wherein each such substituent optionally is substituted with one or more substituents independently selected from the group consisting of $R^E$, $R^F$, $R^G$, $R^H$, $R^I$, $R^J$, and $R^K$. In some such embodiments, the fused 2-ring carbocyclyl and fused 2-ring heterocyclyl are not substituted. In other such embodiments, the fused 2-ring carbocyclyl and fused 2-ring heterocyclyl are substituted with a substituent selected from the group consisting of $R^E$, $R^F$, $R^G$, $R^H$, $R^I$, $R^J$, and $R^K$. In yet other such embodiments, the fused 2-ring carbocyclyl and fused 2-ring heterocyclyl are substituted with two substituents independently selected from the group consisting of $R^E$, $R^F$, $R^G$, $R^H$, $R^I$, $R^J$, and $R^K$. In further such embodiments, the fused 2-ring carbocyclyl and fused 2-ring heterocyclyl are substituted with three substituents independently selected from the group consisting of $R^E$, $R^F$, $R^G$, $R^H$, $R^I$, $R^J$, and $R^K$. In further such embodiments, the fused 2-ring carbocyclyl and fused 2-ring heterocyclyl are substituted with one, two, or three substituents independently selected from the group consisting of $R^E$, $R^F$, $R^G$, $R^H$, $R^I$, $R^J$, and $R^K$.

In some embodiments, $R^4$ is fused 2-ring carbocyclyl optionally substituted with one or more substituents independently selected from the group consisting of $R^E$, $R^F$, $R^G$, $R^H$, $R^I$, $R^J$, and $R^K$. In some such embodiments, the fused 2-ring carbocyclyl is not substituted. In other such embodiments, the fused 2-ring carbocyclyl is substituted with a substituent selected from the group consisting of $R^E$, $R^F$, $R^G$, $R^H$, $R^I$, $R^J$, and $R^K$. In yet other such embodiments, the fused 2-ring carbocyclyl is substituted with two substituents independently selected from the group consisting of $R^E$, $R^F$, $R^G$, $R^H$, $R^I$, $R^J$, and $R^K$. In further such embodiments, the fused 2-ring carbocyclyl is substituted with three substituents independently selected from the group consisting of $R^E$, $R^F$, $R^G$, $R^H$, $R^I$, $R^J$, and $R^K$. In further such embodiments, the fused 2-ring carbocyclyl is substituted with one, two, or three substituents independently selected from the group consisting of $R^E$, $R^F$, $R^G$, $R^H$, $R^I$, $R^J$, and $R^K$.

In some embodiments, $R^4$ is fused 2-ring heterocyclyl optionally substituted with one or more substituents independently selected from the group consisting of $R^E$, $R^F$, $R^G$, $R^H$, $R^I$, $R^J$, and $R^K$. In some such embodiments, the fused 2-ring heterocyclyl is not substituted. In other such embodiments, the fused 2-ring heterocyclyl is substituted with a substituent selected from the group consisting of $R^E$, $R^F$, $R^G$, $R^H$, $R^I$, $R^J$, and $R^K$. In yet other such embodiments, the fused 2-ring heterocyclyl is substituted with two substituents independently selected from the group consisting of $R^E$, $R^F$, $R^G$, $R^H$, $R^I$, $R^J$, and $R^K$. In further such embodiments, the fused 2-ring heterocyclyl is substituted with three substituents independently selected from the group consisting of $R^E$, $R^F$, $R^G$, $R^H$, $R^I$, $R^J$, and $R^K$. In further such embodiments, the fused 2-ring heterocyclyl is substituted with one, two, or three substituents independently selected from the group consisting of $R^E$, $R^F$, $R^G$, $R^H$, $R^I$, $R^J$, and $R^K$.

In some of the above embodiments, the optionally substituted $C_5$-$C_6$-carbocyclyl is selected from the group consisting of cyclopentyl, cyclopentenyl, cyclopentadienyl, cyclohexyl, cyclohexenyl, cyclohexadienyl, and phenyl. In some such embodiments, the optionally substituted $C_5$-$C_6$-carbocyclyl is phenyl.

In some of the above embodiments, the optionally substituted $C_5$-$C_6$-carbocyclyl is $C_5$-carbocyclyl. Examples of $C_5$-carbocyclyls include cyclopentyl, cyclopentenyl, and cyclopentadienyl.

In other of the above embodiments, the optionally substituted $C_5$-$C_6$-carbocyclyl is $C_6$-carbocyclyl. Examples of $C_6$-carbocyclyls include cyclohexyl, cyclohexenyl, cyclohexadienyl, and phenyl.

In some of the above embodiments, the optionally substituted 5-6-membered-heterocyclyl is selected from the group consisting of furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, oxazolyl, dihydrooxazolyl, isoxazolyl, dihydroisoxazolyl, oxazolidinyl, isoxazolidinyl, thiazolyl, isothiazolyl, thiazolinyl, isothiazolinyl, thiazolidinyl, isothiazolidinyl, imidazolyl, imidazolidinyl, pyrazolyl, pyrazolinyl, pyrazolidinyl, oxathiolyl, oxathiolanyl, triazolyl, oxadiazolyl, furazanyl, tetrazolyl, oxatriazolyl, dioxazolyl, oxathiazolyl, oxathiazolidinyl, dihydrooxadiazolyl, dioxazolidinyl, pyranyl, dihydropyranyl, tetrahydropyranyl, pyridinyl, dihydropyridinyl, tetrahydropyridinyl, piperidinyl, diazinyl, pyrazinyl, pyridazinyl, pyrimidinyl, dihydropyrazinyl, tetrahydropyrazinyl, piperazinyl, triazinyl, dihydrotriazinyl, tetrahydrotriazinyl, triazinanyl, oxazinyl, dihydrooxazinyl, morpholinyl, oxathiazinyl, dihydrooxathiazinyl, oxathiazinanyl, oxadiazinyl, dihydrooxadiazinyl, oxadiazinanyl, thiopyranyl, dihydrothiopyranyl, and tetrahydrothiopyranyl.

In some of the above embodiments, the optionally substituted 5-6-membered-heterocyclyl is 5-membered heterocyclyl. Examples of such 5-membered heterocyclyl include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, oxazolyl, dihydrooxazolyl, isoxazolyl, dihydroisoxazolyl, oxazolidinyl, isoxazolidinyl, thiazolyl, isothiazolyl, thiazolinyl, isothiazolinyl, thiazolidinyl, isothiazolidinyl, imidazolyl, imidazolidinyl, pyrazolyl, pyrazolinyl, pyrazolidinyl, oxathiolyl, oxathiolanyl, triazolyl, oxadiazolyl, furazanyl, tetrazolyl, oxatriazolyl, dioxazolyl, oxathiazolyl, oxathiazolidinyl, dihydrooxadiazolyl, and dioxazolidinyl.

In other of the above embodiments, the optionally substituted 5-6-membered-heterocyclyl is 6-membered heterocyclyl. Examples of 6-membered heterocyclyls include pyranyl, dihydropyranyl, tetrahydropyranyl, pyridinyl, dihydropyridinyl, tetrahydropyridinyl, piperidinyl, diazinyl, pyrazinyl, pyridazinyl, pyrimidinyl, dihydropyrazinyl, tetrahydropyrazinyl, piperazinyl, triazinyl, dihydrotriazinyl, tetrahydrotriazinyl, triazinanyl, oxazinyl, dihydrooxazinyl, morpholinyl, oxathiazinyl, dihydrooxathiazinyl, oxathiazinanyl, oxadiazinyl, dihydrooxadiazinyl, oxadiazinanyl, thiopyranyl, dihydrothiopyranyl, and tetrahydrothiopyranyl.

In some of the above embodiments, the optionally substituted fused 2-ring carbocyclyl is selected from the group consisting of naphthalenyl, dihydronaphthalenyl, tetrahydronaphthalenyl, hexahydronaphthalenyl, octahydronaphthalenyl, decahydronaphthalenyl, indenyl, dihydroindenyl, hexahydroindenyl, octahydroindenyl, pentalenyl, octahydropentalenyl, and hexahydropentalenyl. In some such embodiments, the optionally substituted fused 2-ring carbocyclyl is selected from the group consisting of naphthalenyl and dihydroindenyl. In some such embodiments, the optionally substituted fused 2-ring carbocyclyl is naphthalenyl. In other such embodiments, the optionally substituted fused 2-ring carbocyclyl is dihydroindenyl. In further such embodiments, the optionally substituted fused 2-ring carbocyclyl is indenyl.

In some of the above embodiments, the optionally substituted fused 2-ring heterocyclyl is selected from the group consisting of

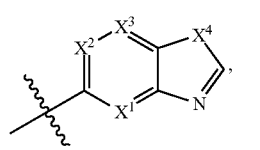 (H1)

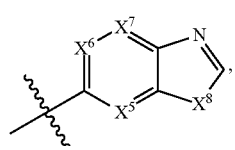 (H2)

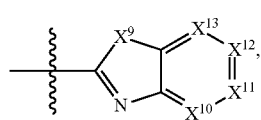 (H3)

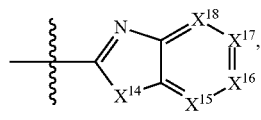 (H4)

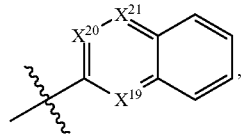 (H5)

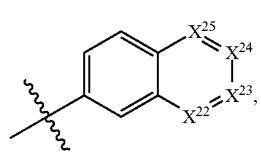 (H6)

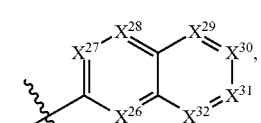 (H7)

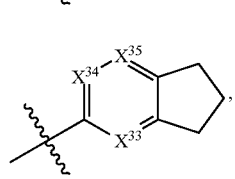 (H8)

-continued

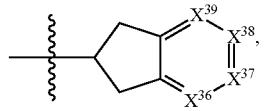 (H9)

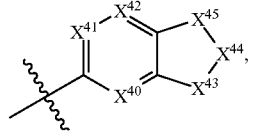 (H10)

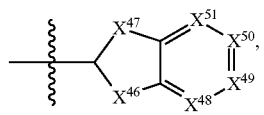 (H11)

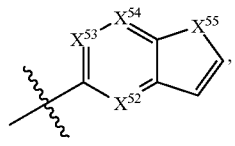 (H12)

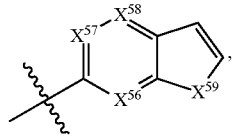 (H13)

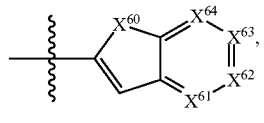 (H14)

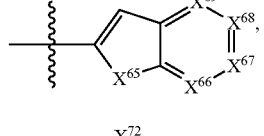 (H15)

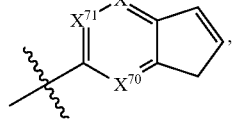 (H16)

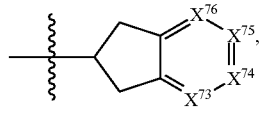 (H17)

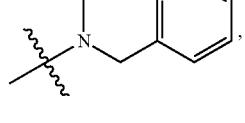 (H18)

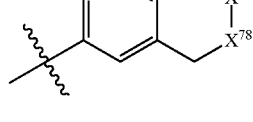 (H19)

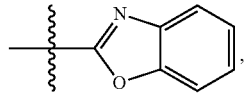 (H20)

-continued

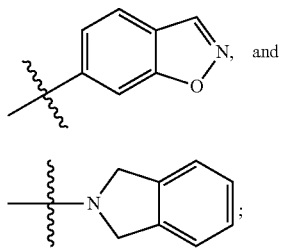
(H21)

(H22)

$X^1$, $X^2$, and $X^3$ are independently selected from the group consisting of N and C(H);
$X^4$ is selected from the group consisting of N(H), O, and S;
$X^5$, $X^6$, and $X^7$ are independently selected from the group consisting of N and C(H);
$X^8$ is selected from the group consisting of N(H), O, and S;
$X^9$ is selected from the group consisting of N(H), O, and S;
$X^{10}$, $X^{11}$, $X^{12}$, and $X^{13}$ are independently selected from the group consisting of N and C(H);
$X^{14}$ is selected from the group consisting of N(H), O, and S;
$X^{15}$, $X^{16}$, $X^{17}$, and $X^{18}$ are independently selected from the group consisting of N and C(H);
one or more of $X^{19}$, $X^{20}$, and $X^{21}$ is N, and the remaining one(s) is/are C(H);
one or more of $X^{22}$, $X^{23}$, $X^{24}$, and $X^{25}$ is N, and the remaining one(s) is/are C(H);
one or more of $X^{26}$, $X^{27}$, and $X^{28}$ is N, and the remaining one(s) is/are C(H);
one or more of $X^{29}$, $X^{30}$, $X^{31}$, and $X^{32}$ is N, and the remaining one(s) is/are C(H);
one or more of $X^{33}$, $X^{34}$, and $X^{35}$ is N, and the remaining one(s) is/are C(H);
one or more of $X^{36}$, $X^{37}$, $X^{38}$, and $X^{39}$ is N, and the remaining one(s) is/are C(H);
$X^{40}$, $X^{41}$, and $X^{42}$ are independently selected from the group consisting of N and C(H);
one of $X^{43}$, $X^{44}$, and $X^{45}$ is selected from the group consisting of N(H), O, and S, and the remaining two are $C(H)_2$;
one of $X^{46}$ and $X^{47}$ is selected from the group consisting of N(H), O, and S, and the other one is $C(H)_2$;
$X^{48}$, $X^{49}$, $X^{50}$, and $X^{51}$ are independently selected from the group consisting of N and C(H);
$X^{52}$, $X^{s3}$, and $X^{54}$ are independently selected from the group consisting of N and C(H);
$X^{55}$ is selected from the group consisting of N(H), O, and S;
$X^{56}$, $X^{57}$, and $X^{58}$ are independently selected from the group consisting of N and C(H);
$X^{59}$ is selected from the group consisting of N(H), O, and S;
$X^{60}$ is selected from the group consisting of N(H), O, and S;
$X^{61}$, $X^{62}$, $X^{63}$, and $X^{64}$ are independently selected from the group consisting of N and C(H);
$X^{65}$ is selected from the group consisting of N(H), O, and S;
$X^{66}$, $X^{67}$, $X^{68}$, and $X^{69}$ are independently selected from the group consisting of N and C(H);

one or more of $X^{70}$, $X^{71}$, and $X^{72}$ is N, and the remaining one(s) is/are C(H);
one or more of $X^{73}$, $X^{74}$, $X^{75}$, and $X^{76}$ is N, and the remaining one(s) is/are C(H); and
one of $X^{77}$ and $X^{78}$ is N(H), and the remaining one is $C(H)_2$.

In some of the above embodiments, the optionally substituted fused 2-ring heterocyclyl is selected from the group consisting of

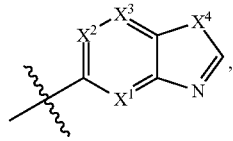
(H1)

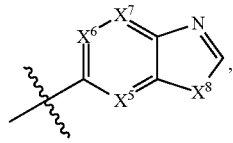
(H2)

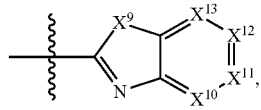
(H3)

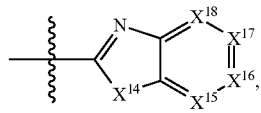
(H4)

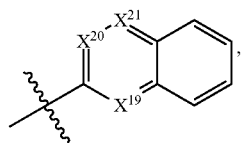
(H5)

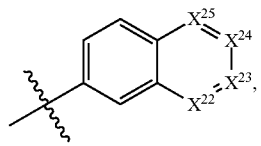
(H6)

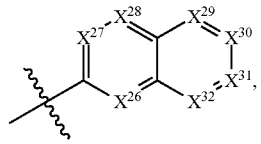
(H7)

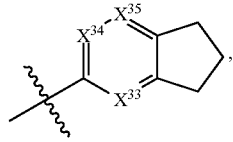
(H8)

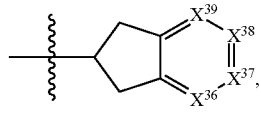
(H9)

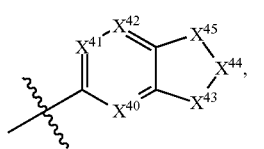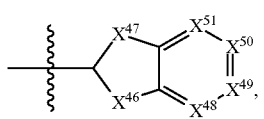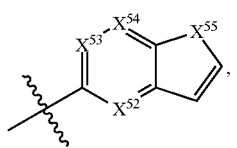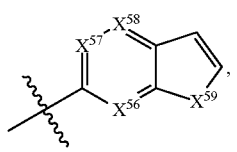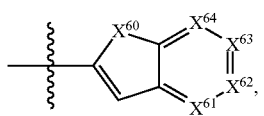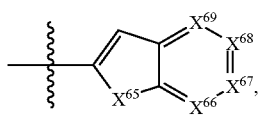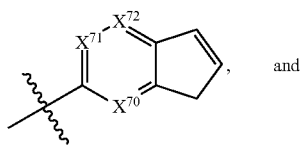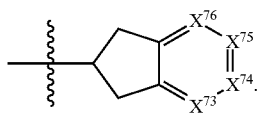

In some of the above embodiments, the optionally substituted fused 2-ring heterocyclyl is selected from the group consisting of:

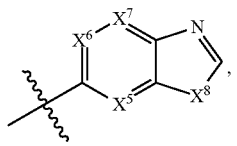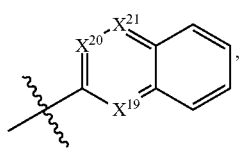

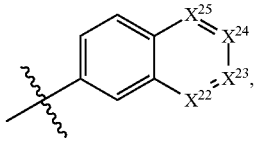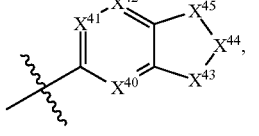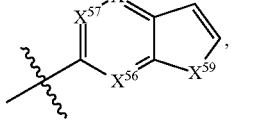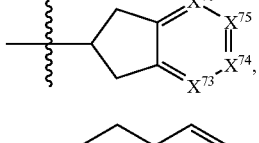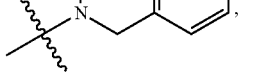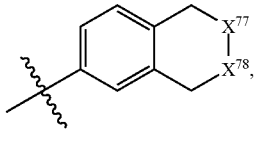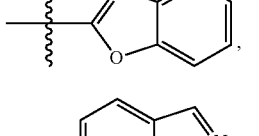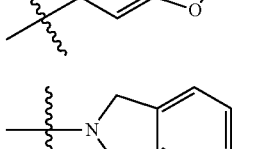

In some of the above embodiments, $X^1$, $X^2$, and $X^3$ are C(H).

In some of the above embodiments, $X^5$, $X^6$, and $X^7$ are C(H).

In some of the above embodiments, $X^{10}$, $X^{11}$, $X^{12}$, and $X^{13}$ are C(H).

In some of the above embodiments, $X^{15}$, $X^{16}$, $X^{17}$, and $X^{18}$ are C(H).

In some of the above embodiments, one of $X^{19}$, $X^{20}$, and $X^{21}$ is N.

In some of the above embodiments, one of $X^{22}$, $X^{23}$, $X^{24}$, and $X^{25}$ is N.

In some of the above embodiments, one of $X^{26}$, $X^{27}$, and $X^{28}$ is N, and one of $X^{29}$, $X^{30}$, $X^{31}$, and $X^{32}$ is N.

In some of the above embodiments, $X^{40}$, $X^{41}$, and $X^{42}$ are C(H).

In some of the above embodiments, $X^{48}$, $X^{49}$, $X^{50}$, and $X^{51}$ are C(H).

In some of the above embodiments, $X^{52}$, $X^{53}$, and $X^{54}$ are C(H).

In some of the above embodiments, $X^{56}$, $X^{57}$, and $X^{58}$ are C(H).

In some of the above embodiments, $X^{56}$, $X^{57}$, and $X^{58}$ are C(H), and $X^{59}$ is S.

In some of the above embodiments, $X^{61}$, $X^{62}$, $X^{63}$, and $X^{64}$ are C(H).

In some of the above embodiments, $X^{66}$, $X^{67}$, $X^{68}$, and $X^{69}$ are C(H).

In some of the above embodiments, one or more of $X^{70}$, $X^{71}$, and $X^{72}$ is N, and the remaining one(s) is/are C(H).

In some of the above embodiments, one or more of $X^{73}$, $X^{74}$, $X^{75}$, and $X^{76}$ is N, and the remaining one(s) is/are C(H).

B23. Substituent $R^E$

Each $R^E$ is independently selected from the group consisting of halo, nitro, hydroxy, oxo, carboxy, cyano, amino, imino, azido, and aldehydo, wherein the amino optionally is substituted with one or two substituents independently selected from the group consisting of alkyl, alkenyl, and alkynyl.

In some embodiment, each $R^E$ is independently selected from the group consisting of halo, nitro, hydroxy, oxo, carboxy, amino, imino, and aldehydo, wherein the amino optionally is substituted with one or two independently selected alkyl.

In some embodiment, each $R^E$ is independently selected from the group consisting of halo, nitro, hydroxy, oxo, carboxy, amino, imino, aldehydo, and alkylamino.

In some embodiment, each $R^E$ is independently selected from the group consisting of chloro, fluoro, nitro, hydroxy, oxo, carboxy, amino, imino, aldehydo, and alkylamino.

In some embodiment, each $R^E$ is independently selected from the group consisting of halo, nitro, hydroxy, oxo, carboxy, cyano, amino, imino, and azido. In some such embodiments, each $R^E$ is halo. In other such embodiments, each $R^E$ is nitro. In yet other such embodiments, each $R^E$ is hydroxy. In yet other such embodiments, each $R^E$ is oxo. In yet other such embodiments, each $R^E$ is carboxy. In yet other such embodiments, each $R^E$ is cyano. In yet other such embodiments, each $R^E$ is amino. In further such embodiments, each $R^E$ is imino. In yet further such embodiments, each $R^E$ is and azido.

In some embodiments, each $R^E$ is independently selected from the group consisting of halo, nitro, hydroxy, oxo, carboxy, cyano, amino, and imino.

B24. Substituent $R^E$

Each $R^F$ is independently selected from the group consisting of alkyl, alkenyl, and alkynyl, wherein:
 each such substituent optionally is substituted with one or more substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
  the amino, imino, aminosulfonyl, aminocarbonyl, carbocyclyl, and heterocyclyl optionally are substituted with one or two substituents independently selected from the group consisting of alkyl, alkenyl, alkynyl, alkylsulfonyl, alkenylsulfonyl, alkynylsulfonyl, alkylsulfonylamino, hydroxy, and alkyloxy, wherein:
   amino portion of the alkylsulfonylamino optionally is substituted with a substituent selected from the group consisting of alkyl, alkenyl, and alkynyl.

In some embodiment, each $R^F$ is independently selected from the group consisting of alkyl, alkenyl, and alkynyl, wherein:
 each such substituent optionally is substituted with one or more substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
  the amino, imino, aminosulfonyl, and aminocarbonyl optionally are substituted with one or two substituents independently selected from the group consisting of alkyl, alkenyl, alkynyl, alkylsulfonyl, alkenylsulfonyl, alkynylsulfonyl, and alkylsulfonylamino, wherein:
   amino portion of the alkylsulfonylamino optionally is substituted with a substituent selected from the group consisting of alkyl, alkenyl, and alkynyl.

In some of the above embodiments, each $R^F$ is independently selected from the group consisting of the alkyl, alkynyl, and alkynyl, wherein such substituents are not substituted.

In some embodiments, each $R^F$ is independently selected from the group consisting of alkyl, alkenyl, and alkynyl, wherein:
 each such substituent optionally is substituted with one or two substituents independently selected from the group consisting of carboxy, hydroxy, halo, amino, imino, nitro, oxo, aminosulfonyl, alkylsulfonyl, alkyloxycarbonyl, alkylcarbonyloxy, alkyloxy, carbocyclyl, heterocyclyl, cyano, and aminocarbonyl, wherein:
  the amino, imino, aminosulfonyl, and aminocarbonyl optionally are substituted with one or two substituents independently selected from the group consisting of alkyl, alkylsulfonyl, and alkylsulfonylamino, wherein:
   amino portion of the alkylsulfonylamino optionally is substituted with alkyl.

In some embodiments, each $R^F$ is an independently selected alkyl optionally substituted with a substituent selected from the group consisting of carboxy, hydroxy, halo, amino, imino, nitro, oxo, aminosulfonyl, alkylsulfonyl, alkyloxycarbonyl, alkylcarbonyloxy, alkyloxy, carbocyclyl, heterocyclyl, cyano, and aminocarbonyl, wherein:
 the amino, imino, aminosulfonyl, and aminocarbonyl optionally are substituted with one or two substituents independently selected from the group consisting of alkyl, alkylsulfonyl, and alkylsulfonylamino, wherein:
  amino portion of the alkylsulfonylamino optionally is substituted with alkyl.

In some embodiments, each $R^F$ is an independently selected alkyl optionally substituted with a substituent selected from the group consisting of carboxy, halo, amino, imino, and aminosulfonyl, wherein:

the amino, imino, and aminosulfonyl optionally are substituted with one or two substituents independently selected from the group consisting of alkyl, alkylsulfonyl, and alkylsulfonylamino.

In some embodiments, each $R^F$ is an independently selected alkyl optionally substituted with amino, wherein the amino optionally is substituted with alkylsulfonyl.

In some embodiments, each $R^F$ is an independently selected alkyl substituted with amino, wherein the amino is substituted with alkylsulfonyl. In some such embodiments, each $R^F$ is methylsulfonylaminomethyl.

In some embodiments, each $R^F$ is independently selected from the group consisting of alkyl, alkenyl, and alkynyl, wherein:
    each such substituent optionally is substituted with one, two, or three substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl.

In some embodiments, each $R^F$ is independently selected alkyl substituted with one or more substituents independently selected from the group consisting of carboxy, hydroxy, halo, amino, imino, nitro, azido, oxo, aminosulfonyl, alkylsulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl.

B25. Substituent $R^G$

Each $R^G$ is independently selected from the group consisting of carbocyclyl and heterocyclyl, wherein:
    each such substituent optionally is substituted with one or more substituents independently selected from the group consisting of alkyl, alkenyl, alkynyl, carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
        the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl.

In some of the above embodiments, each $R^G$ is independently selected from the group consisting of carbocyclyl and heterocyclyl, wherein such substituents are not substituted.

In some embodiments, each $R^G$ is independently selected from the group consisting of carbocyclyl and heterocyclyl, wherein:
    each such substituent optionally is substituted with one or two substituents independently selected from the group consisting of alkyl, carboxy, hydroxy, halo, amino, nitro, oxo, aminosulfonyl, alkyloxycarbonyl, alkylcarbonyloxy, alkyloxy, carbocyclyl, heterocyclyl, cyano, and aminocarbonyl, wherein:
        the amino, aminosulfonyl, and aminocarbonyl optionally are substituted with one or two substituents independently selected from the group consisting of alkyl and alkylsulfonyl.

In some of the above embodiments, the carbocyclyl is $C_3$-$C_6$-carbocyclyl.

In some of the above embodiments, the heterocyclyl is 5-6-membered heterocyclyl.

B26. Substituent $R^H$

Each $R^H$ is independently selected from the group consisting of alkyloxy, alkenyloxy, alkynyloxy, alkylsulfonyloxy, alkenylsulfonyloxy, and alkynylsulfonyloxy, wherein:
    each such substituent optionally is substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
        the amino, aminosulfonyl, and aminocarbonyl optionally are substituted with one or two substituents independently selected from the group consisting of alkyl, alkenyl, alkynyl, alkylsulfonyl, alkenylsulfonyl, and alkynylsulfonyl.

In some of the above embodiments, each $R^H$ is independently selected from the group consisting of alkyloxy, alkenyloxy, alkynyloxy, alkylsulfonyloxy, alkenylsulfonyloxy, and alkynylsulfonyloxy, wherein such substituents are not substituted.

In some embodiments, each $R^U$ is independently selected from the group consisting of alkyloxy and alkylsulfonyloxy, wherein:
    each such substituent optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, carbocyclyl, heterocyclyl, cyano, and aminocarbonyl, wherein:
        the amino, aminosulfonyl, and aminocarbonyl optionally are substituted with one or two substituents independently selected from the group consisting of alkyl and alkylsulfonyl.

In some embodiments, each $R^H$ is independently selected from the group consisting of alkyloxy and alkylsulfonyloxy, wherein:
    each such substituent optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, cyano, and aminocarbonyl, wherein:
        the amino, aminosulfonyl, and aminocarbonyl optionally are substituted with one or two substituents independently selected from the group consisting of alkyl and alkylsulfonyl.

In some embodiments, each $R^H$ is independently selected from the group consisting of alkyloxy and alkylsulfonyloxy, wherein:
    each such substituent optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, cyano, and aminocarbonyl.

In some embodiments, each $R^H$ is independently selected alkyloxy.

In some embodiments, each $R^H$ is independently selected alkylsulfonyloxy.

B27. Substituent $R^I$

Each $R^I$ is independently selected from the group consisting of alkylcarbonyl, alkenylcarbonyl, alkynylcarbonyl, aminocarbonyl, alkyloxycarbonyl, carbocyclylcarbonyl, and heterocyclylcarbonyl, wherein:
- (a) the alkylcarbonyl, alkenylcarbonyl, and alkynylcarbonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, and
- (b) the aminocarbonyl optionally is substituted with one or two substituents independently selected from the group consisting of alkyl, alkenyl, alkynyl, alkyloxyalkyl, carbocyclyl, heterocyclyl, alkylsulfonyl, and alkylsulfonylamino, wherein:
    the carbocyclyl and heterocyclyl optionally are substituted with one or two substituents independently selected from the group consisting of halo, alkyl, and oxo.

In some embodiments, each $R^I$ is independently selected from the group consisting of alkylcarbonyl, alkenylcarbonyl, alkynylcarbonyl, aminocarbonyl, alkyloxycarbonyl, carbocyclylcarbonyl, and heterocyclylcarbonyl, wherein such substituents are not substituted.

In some embodiments, each $R^I$ is independently selected from the group consisting of alkylcarbonyl, aminocarbonyl, alkyloxycarbonyl, carbocyclylcarbonyl, and heterocyclylcarbonyl, wherein:
- (a) the alkylcarbonyl optionally is substituted with a substituent selected from the group consisting of carboxy, hydroxy, halo, amino, nitro, oxo, aminosulfonyl, alkyloxycarbonyl, alkylcarbonyloxy, alkyloxy, and aminocarbonyl, and
- (b) the aminocarbonyl optionally is substituted with a substituent selected from the group consisting of alkyl, alkyloxyalkyl, alkylsulfonyl, and alkylsulfonylamino.

In some embodiments, each $R^I$ is independently selected from the group consisting of alkylcarbonyl and aminocarbonyl, wherein:
    the aminocarbonyl optionally is substituted with a substituent selected from the group consisting of alkyl, alkyloxyalkyl, alkylsulfonyl, and alkylsulfonylamino.

In some embodiment, each $R^I$ is independently selected from the group consisting of alkylcarbonyl, alkenylcarbonyl, alkynylcarbonyl, and aminocarbonyl, wherein:
- (a) the alkylcarbonyl, alkenylcarbonyl, and alkynylcarbonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, and
- (b) the aminocarbonyl optionally is substituted with one or two substituents independently selected from the group consisting of alkyl, alkenyl, alkynyl, and alkylsulfonylamino.

In some of the above embodiments, each $R^I$ is independently selected from the group consisting of alkylcarbonyl, alkenylcarbonyl, alkynylcarbonyl, and aminocarbonyl, wherein such substituents are not substituted.

In some embodiments, each $R^I$ is independently selected from the group consisting of alkylcarbonyl and aminocarbonyl, wherein:
- (a) the alkylcarbonyl optionally is substituted with one or two substituents independently selected from the group consisting of carboxy, hydroxy, halo, amino, nitro, azido, oxo, aminosulfonyl, alkyloxycarbonyl, alkylcarbonyloxy, alkyloxy, carbocyclyl, heterocyclyl, cyano, and aminocarbonyl, and
- (b) the aminocarbonyl optionally is substituted with one or two substituents independently selected from the group consisting of alkyl and alkylsulfonylamino.

In some embodiments, each $R^I$ is independently selected from the group consisting of alkylcarbonyl and aminocarbonyl, wherein:
- (a) the alkylcarbonyl optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, cyano, and aminocarbonyl, and
- (b) the aminocarbonyl optionally is substituted with one or two substituents independently selected from the group consisting of alkyl and alkylsulfonylamino.

In some embodiments, each $R^I$ is independently selected from the group consisting of alkylcarbonyl and aminocarbonyl, wherein:
    the alkylcarbonyl optionally is substituted with one or two substituents independently selected from the group consisting of carboxy, hydroxy, halo, amino, nitro, azido, oxo, aminosulfonyl, alkyloxycarbonyl, alkylcarbonyloxy, alkyloxy, carbocyclyl, heterocyclyl, cyano, and aminocarbonyl.

In some embodiments, each $R^I$ is independently selected alkylcarbonyl.

In some embodiments, each $R^I$ is independently selected aminocarbonyl.

B28. Substituent $R^J$

Each $R^J$ is independently selected from the group consisting of carbocyclylsulfonylamino, heterocyclylsulfonylamino, alkylcarbonylamino, alkenylcarbonylamino, alkynylcarbonylamino, alkyloxycarbonylamino, alkenyloxycarbonylamino, alkynyloxycarbonylamino, alkylsulfonylamino, alkenylsulfonylamino, alkynylsulfonylamino, aminocarbonylamino, alkyloxycarbonylaminoimino, alkylsulfonylaminoimino, alkenylsulfonylaminoimino, and alkynylsulfonylaminoimino, wherein:
- (a) the amino portion of such substituents optionally is substituted with a substituent independently selected from the group consisting of carbocyclylalkyl, heterocyclylalkyl, alkylcarbonyloxy, aminocarbonylalkyl, alkyl, alkenyl, alkynyl, alkylcarbonyl, alkenylcarbonyl, alkynylcarbonyl, alkyloxycarbonyl, alkyloxyalkyloxycarbonyl, alkylcarbonyloxyalkyl, and alkylsulfonyl, wherein:
    - (1) the carbocyclyl portion of the carbocyclylalkyl and the heterocyclyl portion of the heterocyclylalkyl optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, oxo, and amino, and
    - (2) the amino portion of the aminocarbonylalkyl optionally is substituted with one or two substituents independently selected from the group consisting of alkyl, alkenyl, and alkynyl,
- (b) the alkyl, alkenyl, and alkynyl portion of such substituents optionally is substituted with one or more substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl, alkenyl, alkynyl, alkyloxy, alkenyloxy, and alkynyloxy, wherein:
the alkyl optionally is substituted with one or more hydroxy;
(c) the carbocyclyl and heterocyclyl portions of such substituents optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, and amino, wherein:
the amino optionally is substituted with one or two substituents independently selected from the group consisting of alkyl, alkenyl, and alkynyl.

In some embodiment, each $R^J$ is independently selected from the group consisting of carbocyclylsulfonylamino, heterocyclylsulfonylamino, alkylcarbonylamino, alkenylcarbonylamino, alkynylcarbonylamino, alkyloxycarbonylamino, alkenyloxycarbonylamino, alkynyloxycarbonylamino, alkylsulfonylamino, alkenylsulfonylamino, alkynylsulfonylamino, aminocarbonylamino, alkylsulfonylaminoimino, alkenylsulfonylaminoimino, and alkynylsulfonylaminoimino, wherein:
(a) the amino portion of such substituents optionally is substituted with a substituent independently selected from the group consisting of carbocyclylalkyl, heterocyclylalkyl, alkylcarbonyloxy, aminocarbonylalkyl, alkyl, alkenyl, alkynyl, alkylcarbonyl, alkenylcarbonyl, alkynylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, oxo, and amino, and
(2) the amino portion of the aminocarbonylalkyl optionally is substituted with one or two substituents independently selected from the group consisting of alkyl, alkenyl, and alkynyl,
(b) the alkyl, alkenyl, and alkynyl portion of such substituents optionally is substituted with one or more substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl, alkenyl, alkynyl, alkyloxy, alkenyloxy, and alkynyloxy, wherein:
the alkyl optionally is substituted with one or more hydroxy;
(c) the carbocyclyl and heterocyclyl portions of such substituents optionally are substituted with one or more substituents independently selected from the group consisting of alkyl, alkenyl, alkynyl, carboxy, hydroxy, alkyloxy, alkenyloxy, alkynyloxy, halo, nitro, cyano, azido, and amino, wherein:
the amino optionally is substituted with one or two substituents independently selected from the group consisting of alkyl, alkenyl, and alkynyl; and In some of the above embodiments, each $R^J$ is independently selected from the group consisting of carbocyclylsulfonylamino, heterocyclylsulfonylamino, alkylcarbonylamino, alkenylcarbonylamino, alkynylcarbonylamino, alkyloxycarbonylamino, alkenyloxycarbonylamino, alkynyloxycarbonylamino, alkylsulfonylamino, alkenylsulfonylamino, alkynylsulfonylamino, aminocarbonylamino, alkylsulfonylaminoimino, alkenylsulfonylaminoimino, and alkynylsulfonylaminoimino, wherein such substituents are not substituted.

In some embodiments, each $R^J$ is independently selected from the group consisting of carbocyclylsulfonylamino, heterocyclylsulfonylamino, alkylcarbonylamino, alkyloxycarbonylamino, alkylsulfonylamino, aminocarbonylamino, and alkylsulfonylaminoimino, wherein:
(a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl,
(b) the alkyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy;
(c) the carbocyclyl and heterocyclyl portions of such substituents optionally are substituted with one or two substituents independently selected from the group consisting of alkyl, carboxy, hydroxy, alkyloxy, halo, nitro, cyano, and amino, wherein:
the amino optionally is substituted with one or two substituents independently selected alkyl.

In some embodiments, each $R^J$ is independently selected from the group consisting of carbocyclylsulfonylamino, heterocyclylsulfonylamino, alkylsulfonylamino, and alkylsulfonylaminoimino, wherein:
(a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and (2) the amino portion of the aminocarbonylalkyl optionally is substituted with one or two substituents independently selected from the group consisting of alkyl, alkenyl, and alkynyl, (b) the alkyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:

the amino optionally is substituted with one or two substituents independently selected from the group consisting of alkyl and alkyloxy, wherein:

the alkyl optionally is substituted with one or more hydroxy;

(c) the carbocyclyl and heterocyclyl portions of such substituents optionally are substituted with one or two substituents independently selected from the group consisting of alkyl, carboxy, hydroxy, alkyloxy, halo, nitro, cyano, and amino, wherein:

the amino optionally is substituted with one or two substituents independently selected alkyl.

In some embodiments, each $R^1$ is independently selected from the group consisting of carbocyclylsulfonylamino, heterocyclylsulfonylamino, alkylsulfonylamino, and alkylsulfonylaminoimino, wherein:

the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:

(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and (2) the amino portion of the aminocarbonylalkyl optionally is substituted with one or two substituents independently selected from the group consisting of alkyl, alkenyl, and alkynyl.

In some embodiments, each $R^1$ is independently selected from the group consisting of carbocyclylsulfonylamino, heterocyclylsulfonylamino, alkylsulfonylamino, and alkylsulfonylaminoimino, wherein:

the alkyl portion of the alkylsulfonylamino and alkylsulfonylaminoimino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:

the amino optionally is substituted with one or two substituents independently selected from the group consisting of alkyl and alkyloxy, wherein:

the alkyl optionally is substituted with one or more hydroxy.

In some embodiments, each $R^J$ is independently selected from the group consisting of carbocyclylsulfonylamino, heterocyclylsulfonylamino, alkylsulfonylamino, and alkylsulfonylaminoimino, wherein:

the carbocyclyl and heterocyclyl portions of such substituents optionally are substituted with one or two substituents independently selected from the group consisting of alkyl, carboxy, hydroxy, alkyloxy, halo, nitro, cyano, and amino.

In some embodiments, each $R^J$ is independently selected from the group consisting of alkylsulfonylamino, alkenylsulfonylamino, alkynylsulfonylamino, and alkylsulfonylaminoimino, wherein:

(a) the amino portion of such substituents optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:

(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and (2) the amino portion of the aminocarbonylalkyl optionally is substituted with one or two substituents independently selected from the group consisting of alkyl, alkenyl, and alkynyl, (b) the alkyl, alkenyl, and alkynyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:

the amino optionally is substituted with one or two substituents independently selected from the group consisting of alkyl and alkyloxy, wherein:

the alkyl optionally is substituted with one or more hydroxy.

In some embodiments, each $R^J$ is an independently selected alkylsulfonylamino, wherein:

(a) the amino portion of the alkylsulfonylamino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:

(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and (2) the amino portion of the aminocarbonylalkyl optionally is substituted with one or two substituents independently selected from the group consisting of alkyl, alkenyl, and alkynyl, (b) the alkyl portion of the alkylsulfonylamino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:

the amino optionally is substituted with one or two substituents independently selected from the group consisting of alkyl and alkyloxy, wherein:
the alkyl optionally is substituted with one or more hydroxy.

In some embodiments, each $R^J$ is an independently selected alkylsulfonylamino, wherein:
the amino portion of the alkylsulfonylamino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl.

In some embodiments, each $R^J$ is an independently selected alkylsulfonylamino, wherein:
the amino portion of the alkylsulfonylamino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl.

In some embodiments, each $R^J$ is an independently selected alkylsulfonylamino, wherein:
the alkyl portion of the alkylsulfonylamino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy.

In some embodiments, each $R^J$ is an independently selected alkylsulfonylamino, wherein:
the alkyl portion of the alkylsulfonylamino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano.

In some embodiments, each $R^J$ is an independently selected alkylsulfonylamino. In some such embodiments, each $R^J$ is methylsulfonylamino.

In some embodiments, each $R^J$ is an independently selected alkylsulfonylaminoimino, wherein:
(a) the amino portion of the alkylsulfonylaminoimino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl,
(b) the alkyl portion of the alkylsulfonylaminoimino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy.

In some embodiments, each $R^J$ is an independently selected alkylsulfonylaminoimino, wherein:
the amino portion of the alkylsulfonylaminoimino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl, wherein:
(1) the carbocyclyl portion of the carbocyclylalkyl and the heterocyclyl portion of the heterocyclylalkyl optionally are substituted with one or two substituents independently selected from the group consisting of alkyl, carboxy, hydroxy, alkyloxy, halo, nitro, cyano, oxo, and amino, and
(2) the amino portion of the aminocarbonylalkyl optionally is substituted with one or two substituents independently selected from the group consisting of alkyl, alkenyl, and alkynyl.

In some embodiments, each $R^J$ is an independently selected alkylsulfonylaminoimino, wherein:
the amino portion of the alkylsulfonylaminoimino optionally is substituted with a substituent independently selected from the group consisting of carbocyclylalkyl, heterocyclylalkyl, alkylcarbonyloxy, aminocarbonylalkyl, alkyl, alkylcarbonyl, alkyloxycarbonyl, alkyloxyalkyloxycarbonyl, alkylcarbonyloxyalkyl, and alkylsulfonyl.

In some embodiments, each $R^J$ is an independently selected alkylsulfonylaminoimino, wherein:
the alkyl portion of the alkylsulfonylaminoimino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano, wherein:
the amino optionally is substituted with one or two substituents independently selected from the group consisting of alkyl and alkyloxy, wherein:
the alkyl optionally is substituted with one or more hydroxy.

In some embodiments, each $R^J$ is an independently selected alkylsulfonylaminoimino, wherein:
the alkyl portion of the alkylsulfonylaminoimino optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano.

In some embodiments, each $R^J$ is an independently selected alkylsulfonylaminoimino. In some such embodiments, each $R^J$ is methylsulfonylaminoimino.

In some embodiments, each $R^J$ is independently selected from the group consisting of alkylcarbonylamino and alkyloxycarbonylamino, wherein:
the alkyl portion of such substituents optionally is substituted with one or two substituents independently selected from the group consisting of carboxy, halo, oxo, amino, alkyloxycarbonyl, alkylcarbonyloxy, hydroxy, alkyloxy, carbocyclyl, heterocyclyl, and cyano.

B29. Substituent $R^K$

Each $R^K$ is independently selected from the group consisting of aminosulfonyl, alkylsulfonyl, alkenylsulfonyl, and alkynylsulfonyl, wherein:
(a) the alkylsulfonyl, alkenylsulfonyl, and alkynylsulfonyl optionally are substituted with one or more substituents independently selected from the group consisting of carboxy, hydroxy, halo, amino, nitro, azido, oxo, aminosulfonyl, alkyloxycarbonyl, alkenyloxycarbonyl, alkynyloxycarbonyl, alkylcarbonyloxy, alkenylcarbonyloxy, alkynylcarbonyloxy, alkyloxy, alkenyloxy, alkynyloxy, carbocyclyl, heterocyclyl, cyano, and aminocarbonyl, wherein:
the amino, aminosulfonyl, and aminocarbonyl optionally are substituted with one or two substituents independently selected from the group consisting of alkyl, alkenyl, and alkynyl; and
(b) the aminosulfonyl optionally is substituted with one or two substituents independently selected from the group consisting of alkyl, alkenyl, and alkynyl.

In some of the above embodiments, each $R^K$ is independently selected from the group consisting of aminosulfonyl, alkylsulfonyl, alkenylsulfonyl, and alkynylsulfonyl, wherein such substituents are not substituted.

In some embodiments, each $R^K$ is independently selected from the group consisting of aminosulfonyl and alkylsulfonyl, wherein:
(a) the alkylsulfonyl optionally is substituted with one or two substituents independently selected from the group consisting of carboxy, hydroxy, halo, amino, nitro, oxo, aminosulfonyl, alkyloxycarbonyl, alkylcarbonyloxy, alkyloxy, carbocyclyl, heterocyclyl, cyano, and aminocarbonyl; and
(b) the aminosulfonyl optionally is substituted with one or two substituents independently selected alkyl.

In some embodiments, each $R^K$ is independently selected from the group consisting of aminosulfonyl and alkylsulfonyl.

C. EMBODIMENTS OF COMPOUNDS OF FORMULA (I)

Various embodiments of substituents $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, L, $R^A$, $R^B$, $R^C$, $R^D$, $R^L$, $R^M$, $R^E$, $R^F$, $R^G$, $R^H$, $R^I$, $R^J$, and $R^K$ have been discussed above. These substituent embodiments can be combined to form various embodiments of compounds of formula (I). All embodiments of compounds of formula (I) formed by combining the substituent embodiments discussed above are within the scope of Applicants' invention, and some illustrative embodiments of the compounds of formula (I) are provided below.

In some embodiments, the compounds of formula (I) correspond in structure to formula (I-1), wherein:
--*-- is selected from the group consisting of single carbon-carbon bond and double carbon-carbon bond;
$R^5$ is selected from the group consisting of hydrogen and methyl;
$R^6$ is selected from the group consisting of hydrogen, methyl, and nitrogen-protecting group;
$R^7$ is hydrogen;
$R^2$ is selected from the group consisting of alkyl, and heterocyclyl, wherein:
(a) the alkyl optionally is substituted with one or more halo, and
(b) the heterocyclyl optionally is substituted with up to two alkyl substituents;
$R^3$ is selected from the group consisting of alkyl, alkenyl, alkyloxy, amino, and halo;
as to L and $R^4$:
L is a bond, and $R^4$ is selected from the group consisting of $C_5$-$C_6$-carbocyclyl, 5-6-membered heterocyclyl, fused 2-ring carbocyclyl and fused 2-ring heterocyclyl, wherein each such substituent optionally is substituted with one or more substituents independently selected from the group consisting of $R^E$, $R^F$, $R^G$, $R^H$, $R^I$, $R^J$, and $R^K$, or
L is $C(R^A)\!=\!C(R^B)$, and $R^4$ is selected from the group consisting of $C_5$-$C_6$-carbocyclyl and 5-6-membered heterocyclyl, wherein each such substituent optionally is substituted with one or more substituents independently selected from the group consisting of $R^E$, $R^F$, $R^G$, $R^H$, $R^I$, $R^J$, and $R^K$; and
$R^A$ and $R^B$ are independently selected from the group consisting of hydrogen and $C_1$-$C_6$-alkyl.

In some embodiments, the compounds of formula (I) correspond in structure to formula (I-1), wherein:
--*-- is a double carbon-carbon bond;
$R^5$ is hydrogen;
$R^6$ is hydrogen;
$R^7$ is hydrogen;
$R^2$ is alkyl;
$R^3$ is alkyloxy;
L is a bond;
$R^4$ is fused 2-ring heterocyclyl optionally substituted with $R^F$; and
$R^F$ is alkyl substituted with amino, wherein the amino is substituted with alkylsulfonyl.

D. ISOMERS

This invention also is directed, in part, to all isomers of the compounds of formula (I) (and their salts) (i.e., structural and stereoisomers). Structural isomers include chain and position isomers. Stereoisomers include E/Z isomers (i.e., isomers with regard to one or more double bonds), enantiomers (i.e., stereo-isomers that have opposite configurations at all stereogenic centers), and diastereoisomers (i.e., stereo-isomers that have the same configuration at one or more stereogenic centers, but differ at other stereogenic centers).

E. SALTS

This invention also is directed, in part, to all salts of the compounds of formula (I). A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula (I) can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula (I) include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

F. PURITY

Compounds of formula (I) (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

G. COMPOSITIONS

This invention also is directed, in part, to compositions comprising one or more compounds and/or salts of the invention (including the crystalline compounds and salts discussed in section G above). In some embodiments, the compositions comprise one or more substantially phase pure crystalline forms (compounds/salts/solvates/hydrates) discussed in section G above. The compositions can be pharmaceutical compositions.

In some embodiments, the compositions further comprise one or more additional therapeutic agents. Such therapeutic agents can, but need not be, additional HCV inhibitors.

The preferred composition depends on the method of administration, and typically comprises one or more conventional pharmaceutically acceptable carriers, adjuvants, and/or vehicles (together referred to as "excipients"). Formulation of drugs is generally discussed in, for example, Hoover, J., Remington's Pharmaceutical Sciences (Mack Publishing Co., 1975) and Ansel's Pharmaceutical Dosage Forms and Drug Delivery Systems (Lippincott Williams & Wilkins, 2005).

Solid dosage forms for oral administration include, for example, capsules, tablets, pills, powders, and granules. In such solid dosage forms, the compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

Liquid dosage forms for oral administration include, for example, pharmaceutically acceptable emulsions (including both oil-in-water and water-in-oil emulsions), solutions (including both aqueous and non-aqueous solutions), suspensions (including both aqueous and non-aqueous suspensions), syrups, and elixirs containing inert diluents commonly used in the art (e.g., water). Such compositions also can comprise, for example, wetting, emulsifying, suspending, flavoring (e.g., sweetening), and/or perfuming agents.

Parenteral administration includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

Formulations for parenteral administration may, for example, be prepared from sterile powders or granules having one or more of the excipients mentioned for use in the formulations for oral administration. A compound or salt of the invention can be dissolved in water, polyethylene glycol, propylene glycol, ethanol, corn oil, cottonseed oil, peanut oil, sesame oil, benzyl alcohol, sodium chloride, and/or various buffers. The pH may be adjusted, if necessary, with a suitable acid, base, or buffer.

Suppositories for rectal administration can be prepared by, for example, mixing a compound or salt of the invention with a suitable nonirritating excipient that is solid at ordinary temperatures, but liquid at the rectal temperature, and will therefore melt in the rectum to release the drug. Suitable excipients include, for example, cocoa butter; synthetic mono-, di-, or triglycerides, fatty acids, and/or polyethylene glycols.

Topical administration includes the use of transdermal administration, such as transdermal patches or iontophoresis devices.

Other excipients and modes of administration known in the pharmaceutical art also may be used.

The preferred total daily dose of the compound or salt (administered in single or divided doses) is typically from about 0.001 to about 100 mg/kg, more preferably from about 0.001 to about 30 mg/kg, and even more preferably from about 0.01 to about 10 mg/kg (i.e., mg of the compound or salt per kg body weight). Dosage unit compositions can contain such amounts or submultiples thereof to make up the daily dose. In many instances, the administration of the compound or salt will be repeated a plurality of times. Multiple doses per day typically may be used to increase the total daily dose, if desired.

Factors affecting the preferred dosage regimen include the type, age, weight, sex, diet, and condition of the patient; the severity of the pathological condition; the severity of the pathological condition; the route of administration; pharmacological considerations, such as the activity, efficacy, pharmacokinetic, and toxicology profiles of the particular compound or salt used; whether a drug delivery system is utilized; and whether the compound or salt is administered as part of a drug combination. Thus, the dosage regimen actually employed can vary widely, and therefore, can derive from the preferred dosage regimen set forth above.

H. KITS

This invention also is directed, in part, to a kit comprising one or more compounds and/or salts of the in invention. The kit can optionally contain one or more additional therapeutic agents and/or instructions for, for example, using the kit.

I. METHODS OF USE

This invention also is directed, in part, to a method for inhibiting replication of an RNA virus. The method comprises exposing the virus to one or more compounds and/or salts of this invention. In some embodiments, replication of the RNA virus is inhibited in vitro. In other embodiments, replication of the RNA virus is inhibited in vivo. In some embodiments, the RNA virus whose replication is being inhibited is a single-stranded, positive sense RNA virus. In some such embodiments, the RNA virus whose replication is being inhibited is a virus from the Flaviviridae family. In some such embodiments, the RNA virus whose replication is being inhibited is HCV.

This invention also is directed, in part, to a method for inhibiting HCV RNA polymerase. The method comprises exposing the polymerase with one or more compounds and/or salts of this invention. In some embodiments, HCV RNA polymerase activity is inhibited in vitro. In other embodiments, HCV RNA polymerase activity is inhibited in vivo.

The term "inhibiting" means reducing the level of RNA virus replication/HCV polymerase activity either in vitro or in vivo. For example, if a compound/salt of the invention reduces the level of RNA virus replication by at least about 10% compared to the level of RNA virus replication before the virus was exposed to the compound/salt, then the compound/salt inhibits RNA virus replication.

In some embodiments, the compound/salt can inhibit RNA virus replication by at least about 20%, at least about 30%, at least about 40%, at least about 50%, at least about 60%, at least about 70%, at least about 80%, at least about 90%, or at least about 95%.

This invention also is directed, in part, to a method for treating a disease that can be treated by inhibiting HCV RNA polymerase. Thus, this invention also is directed, in part, to a method for treating hepatitis C in an animal in need of such treatment. These methods comprise administering to the animal one or more compounds and/or salts of the invention, and, optionally, one or more additional therapeutic agents. In some embodiments, a therapeutically effective amount of the compound(s) and/or salt(s) is administered to the animal. "Treating" means ameliorating, suppressing, eradicating, preventing, reducing the risk of, and/or delaying the onset of the disease being treated. Applicants specifically intend that the term "treating" encompass administration of the compounds and/or salts of the invention to an HCV-negative patient that is a candidate for an organ transplant. The methods of treatment are particularly suitable for use with humans, but may be used with other animals, particularly mammals. A "therapeutically-effective amount" or "effective amount" is an amount that will achieve the goal of treating the targeted condition.

In some embodiments, the methods comprise combination therapy, wherein the compound(s) and/or salt(s) of the invention is/are co-administered with a second (or even a third, fourth, etc.) compound, such as, for example, another therapeutic agent used to treat hepatitis C (e.g., interferon or interferon/ribavirin combination, or an HCV inhibitor such as, for example, an HCV polymerase inhibitor or an HCV protease inhibitor). The compound(s) and/or salt(s) of this invention can also be co-administered with therapeutic agents other than therapeutic agents used to treat hepatitis C (e.g., anti-HIV agents). In these co-administration embodiments, the compound(s) and/or salt(s) of the invention and the second, etc. therapeutic agent(s) may be administered in a substantially simultaneous manner (e.g., or within about 5 minutes of each other), in a sequential manner, or both. It is contemplated that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. The compound(s) and/or salt(s) of this invention and the second, etc. therapeutic agent may also be administered in a single formulation.

This invention also is directed, in part, to a use of one or more compounds and/or salts of the invention, and, optionally one or more additional therapeutic agents to prepare a medicament. In some embodiments, the medicament is for co-administration with one or more additional therapeutic agents.

In some embodiments, the medicament is for inhibiting replication of an RNA virus.

In some embodiments, the medicament is for treating hepatitis C.

This invention also is directed, in part, to one or more compounds and/or salts of the invention, and, optionally one or more additional therapeutic agents, for use as a medicament. In some embodiments, the medicament is for inhibiting replication of an RNA virus. In other embodiments, the medicament is for treating hepatitis C.

J. METHODS FOR PREPARATION

Additional information about the preparation of compounds of formulas (I) and (II) (and their salts) is provided in the general discussion and/or specific synthesis examples below. In the discussion below, $R^1$, $R^2$, $R^3$, $R^4$, $R^5$, L, $R^A$, $R^B$, $R^C$, $R^D$, $R^6$, $R^E$, $R^F$, $R^G$, $R^H$, $R^I$, $R^J$, $R^K$, $X^1$, and $X^2$ have the meaning discussed above unless otherwise stated.

Scheme 1

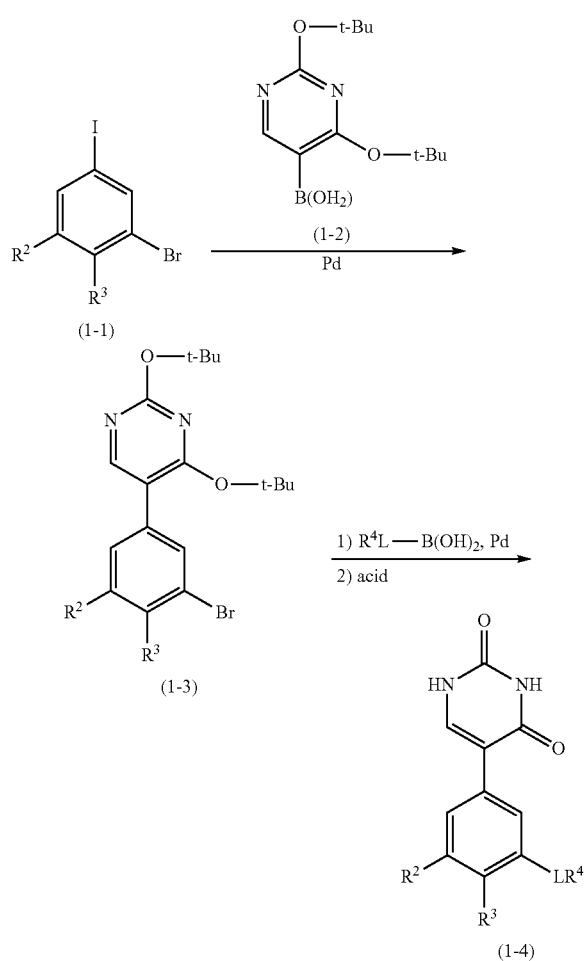

As described in Scheme 1, compounds of formula (1-4), wherein $R^2$ and $R^3$ are described in the Summary of the Invention and L-$R^4$ is aryl, heteroaryl, styrylaryl or styrylheteroaryl, can be prepared from compounds of formula (1-1). Accordingly, compounds of formula (1-1) can be reacted with a boronic acid of formula (1-2) under Suzuki reaction conditions to supply compounds of formula (1-3). Compounds of formula (1-3) can be converted to compounds of formula (1-4) using a second Suzuki reaction to introduce L-$R^4$ followed by acid hydrolysis to give the uracil moiety. Compounds of formula (1-4) are representative of compounds of formula (I).

Scheme 2

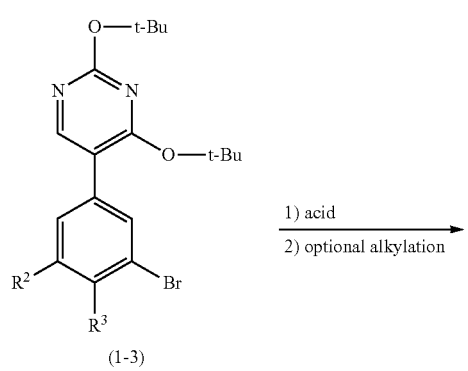

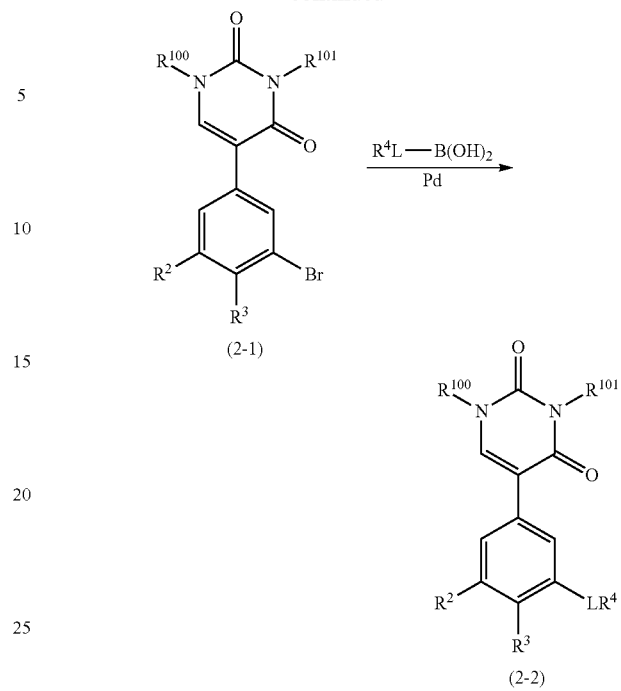

As described in Scheme 2, compounds of formula (2-2), wherein $R^2$ and $R^3$ are described in the Summary of the Invention and L-$R^4$ is aryl, heteroaryl, styrylaryl or styrylheteroaryl, and $R^{100}$ and $R^{101}$ are optionally alkyl groups, can be prepared from compounds of formula (1-3). Compounds of formula (1-3) can be hydrolyzed under acid conditions to reveal a uracil ring. The nitrogens of the uracil can be optionally alkylated at this point yielding compounds of formula (2-1). Compounds of formula (2-1) can be transformed to compounds of formula (2-2) using a Suzuki reaction to introduce L-$R^4$. Compounds of formula (2-2) are representative of compounds of formula (I).

Scheme 3

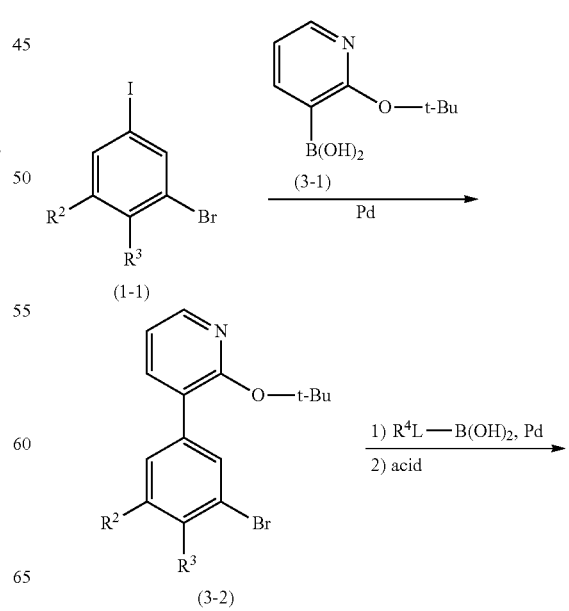

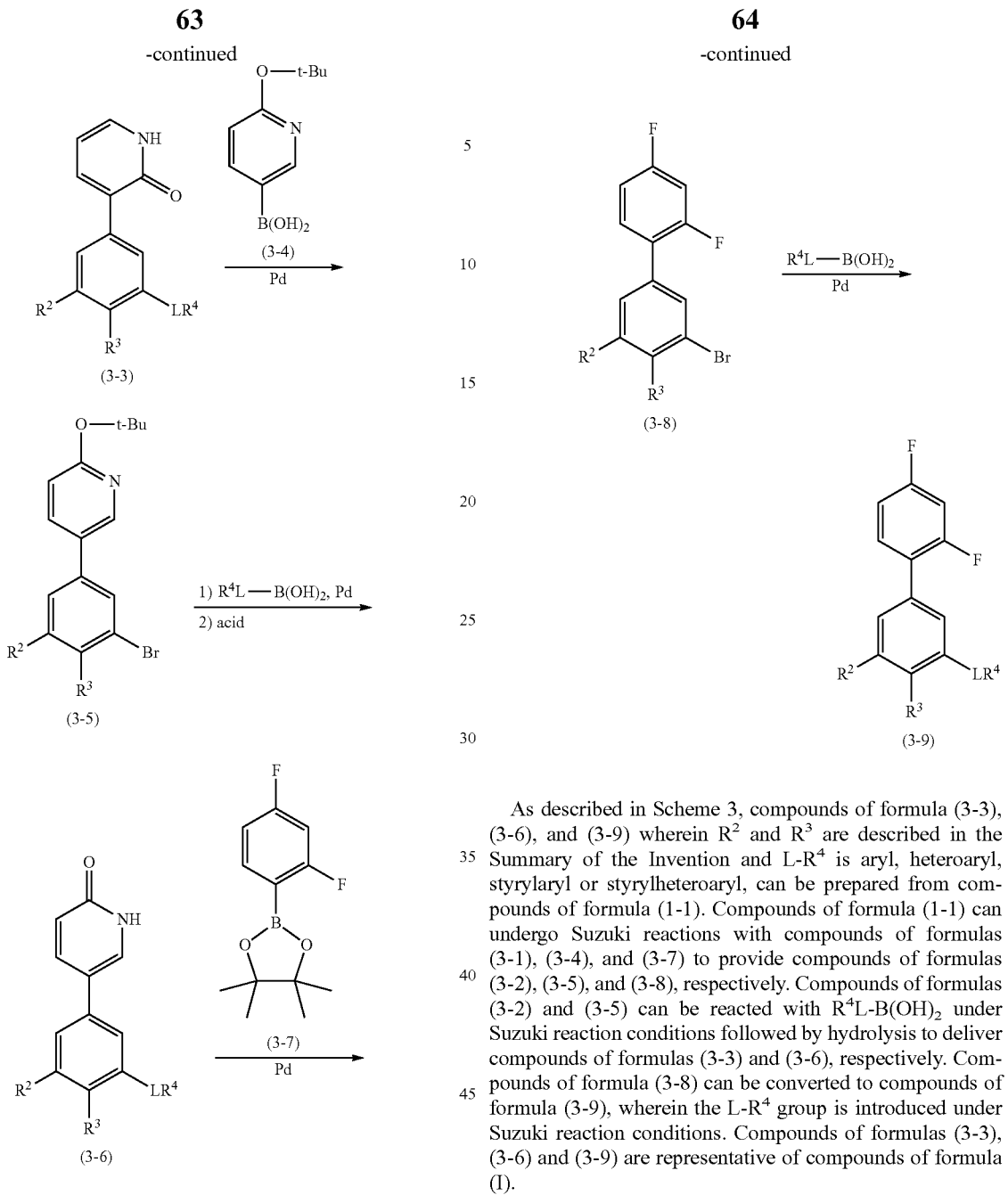

As described in Scheme 3, compounds of formula (3-3), (3-6), and (3-9) wherein $R^2$ and $R^3$ are described in the Summary of the Invention and L-$R^4$ is aryl, heteroaryl, styrylaryl or styrylheteroaryl, can be prepared from compounds of formula (1-1). Compounds of formula (1-1) can undergo Suzuki reactions with compounds of formulas (3-1), (3-4), and (3-7) to provide compounds of formulas (3-2), (3-5), and (3-8), respectively. Compounds of formulas (3-2) and (3-5) can be reacted with $R^4$L-B(OH)$_2$ under Suzuki reaction conditions followed by hydrolysis to deliver compounds of formulas (3-3) and (3-6), respectively. Compounds of formula (3-8) can be converted to compounds of formula (3-9), wherein the L-$R^4$ group is introduced under Suzuki reaction conditions. Compounds of formulas (3-3), (3-6) and (3-9) are representative of compounds of formula (I).

Scheme 4

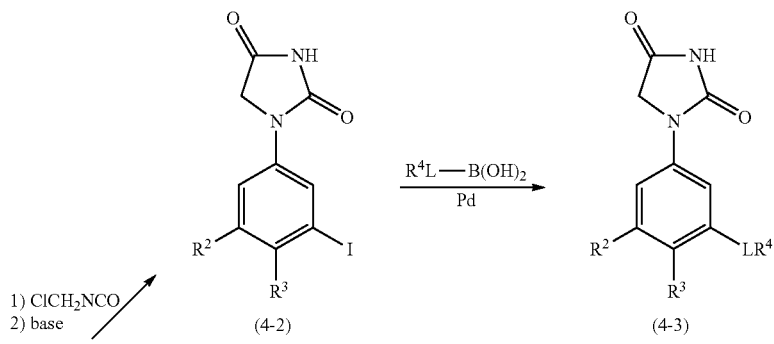

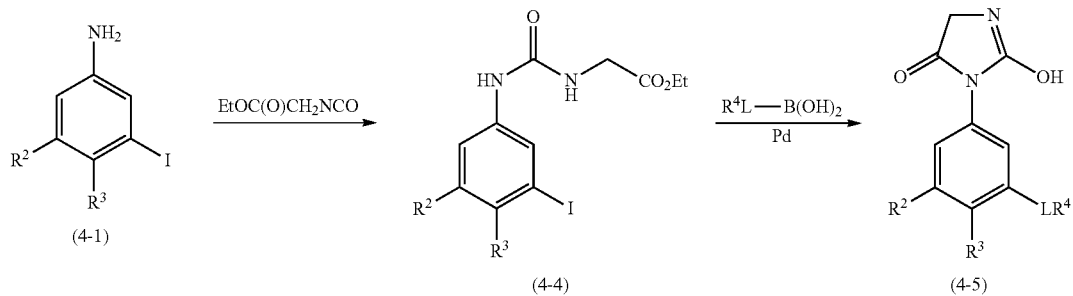

As described in Scheme 4, compounds of formula (4-3) and (4-5), wherein $R^2$ and $R^3$ are described in the Summary of the Invention and L-$R^4$ is aryl, heteroaryl, styrylaryl or styrylheteroaryl, can be prepared from compounds of formula (4-1). Compounds of formula (4-1) can be reacted with ClCH$_2$NCO and then treated with base to give compounds of formula (4-2). A Suzuki reaction to introduce L-$R^4$ gives compounds of formula (4-3). Compounds of formula (4-1) can also be reacted with EtOC(O)CH$_2$NCO to give compounds of formula (4-4). Under Suzuki reaction conditions to introduce L-$R^4$, cyclization also occurs giving compounds of formula (4-5). Compounds of formulas (4-3) an (4-5) are representative of compounds of formula (I).

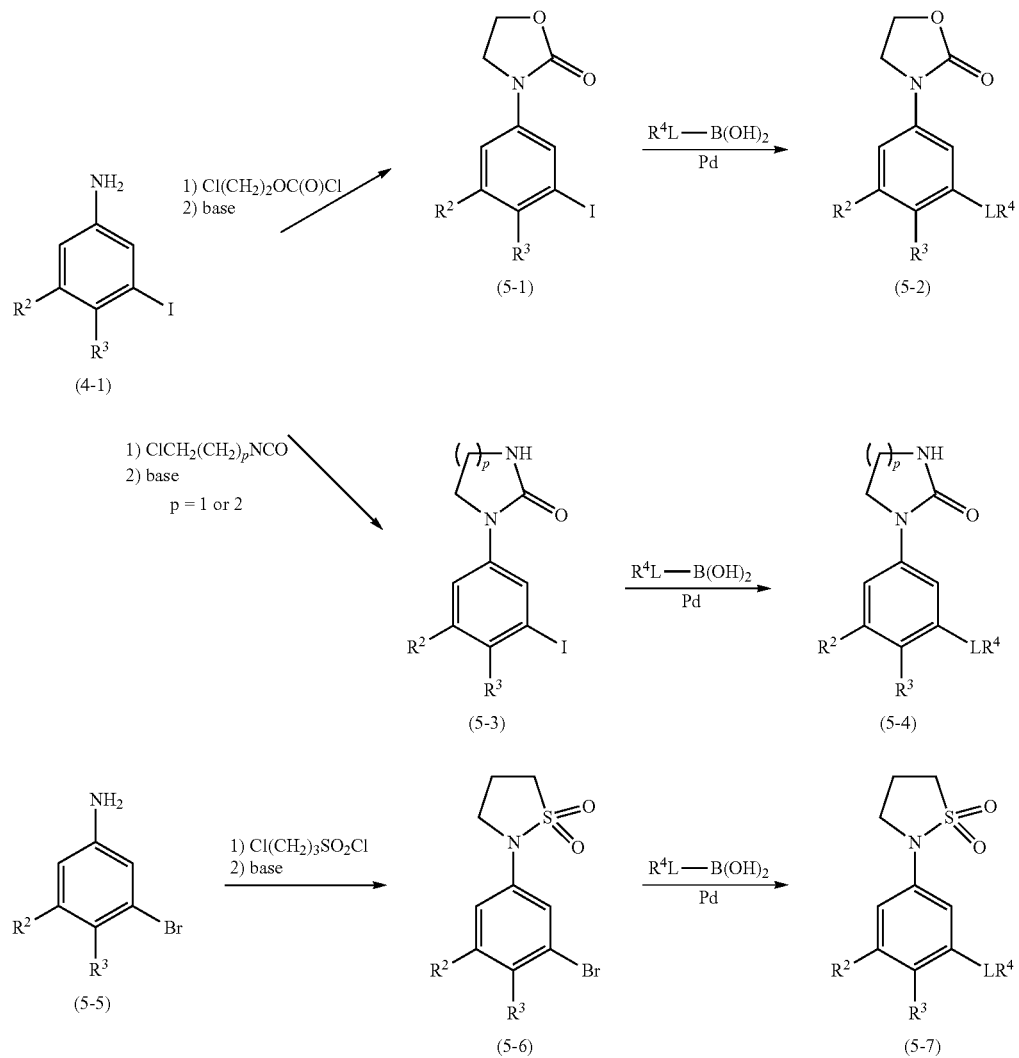

As described in Scheme 5, compounds of formula (5-2) and (5-4), wherein $R^2$ and $R^3$ are described in the Summary of the Invention and L-$R^4$ is aryl, heteroaryl, styrylaryl or styrylheteroaryl, can be prepared from compounds of formula (4-1). Compounds of formula (4-1) can be reacted with $Cl(CH_2)_2OC(O)Cl$ and then treated with a base to give oxazolidinones of formula (5-1). Introduction of L-$R^4$ under Suzuki reaction conditions supplies compounds of formula (5-2). A similar conversion occurs when compounds of formula (4-1) are treated with $ClCH_2(CH_2)_pNCO$ and then a base to give compounds of formula (5-3). A Suzuki reaction completes the sequence to compounds of formula (5-4).

Also described in Scheme 5 is the preparation of compounds of formula (5-7), wherein $R^2$, $R^3$ are described in the Summary of the Invention and L-$R^4$ is aryl, heteroaryl, styrylaryl or styrylheteroaryl, from compounds of formula (5-5). Compounds of formula (5-5) can be reacted with $Cl(CH_2)_3SO_2Cl$ and then base to give compounds of formula (5-6). L-$R^4$ is introduced as described for compounds of formulas (5-2) and (5-4) to give compounds of formula (5-7).

Compounds of formulas (5-2), (5-4), and (5-7) are representative of compounds of formula (I).

As described in Scheme 6, compounds of formula (6-2) and (6-4), wherein n, m, $R^2$, $R^3$, $R^{15}$ and $R^{15}$ are described in the Summary of the Invention and L-$R^4$ is aryl, heteroaryl, styrylaryl or styrylheteroaryl, can be prepared from compounds of formula (4-1). Compounds of formula (4-1) can be reacted with carboxylic acids, $R^{15}(CH_2)_nCO_2H$, under amide bond forming reaction conditions to give compounds of formula (6-1). Suzuki reaction conditions deliver L-$R^4$ providing compounds of formula (6-2).

Compounds of formula (4-1) can be reacted with isocyanates of formula $R^{16}(CH_2)_mNCO$ giving compounds of formula (6-3). Compounds are also converted under Suzuki reaction conditions to compounds of formula (6-4).

Compounds of formulas (6-2) and (6-4) are representative of compounds of formula (I).

Scheme 7

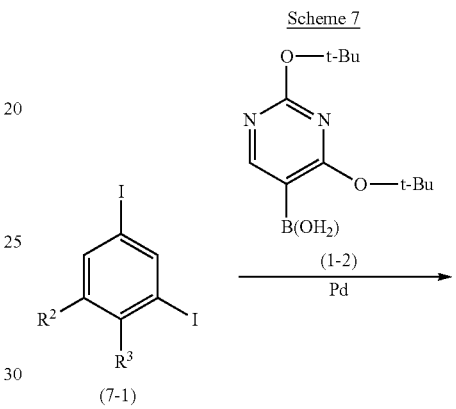

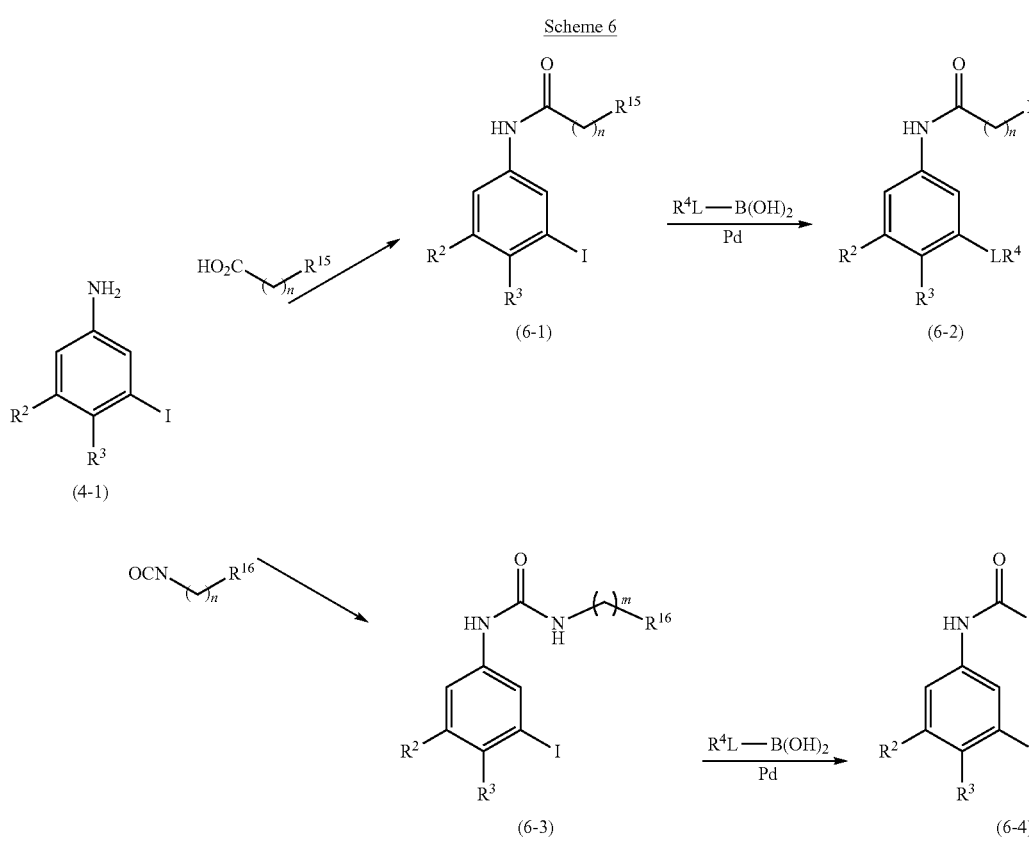

-continued

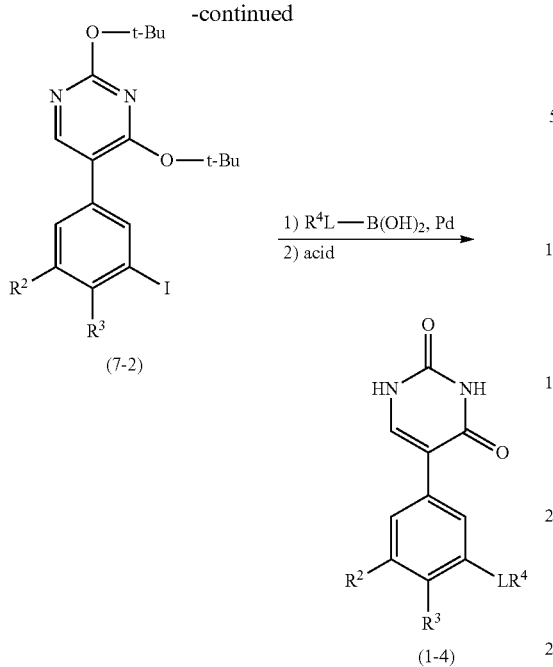

As described in Scheme 7, compounds of formula (1-4), wherein $R^2$ and $R^3$ are described in the Summary of the Invention and L-$R^4$ is aryl, heteroaryl, styrylaryl or styryl-heteroaryl, can be prepared from compounds of formula (7-1). Accordingly, compounds of formula (7-1) can be selectively reacted with a boronic acid of formula (1-2) under Suzuki reaction conditions to supply compounds of formula (7-2). Compounds of formula (7-2) can be converted to compounds of formula (1-4) using a second Suzuki reaction to introduce L-$R^4$ followed by acid hydrolysis to give the uracil moiety. Compounds of formula (1-4) are representative of compounds of formula (I).

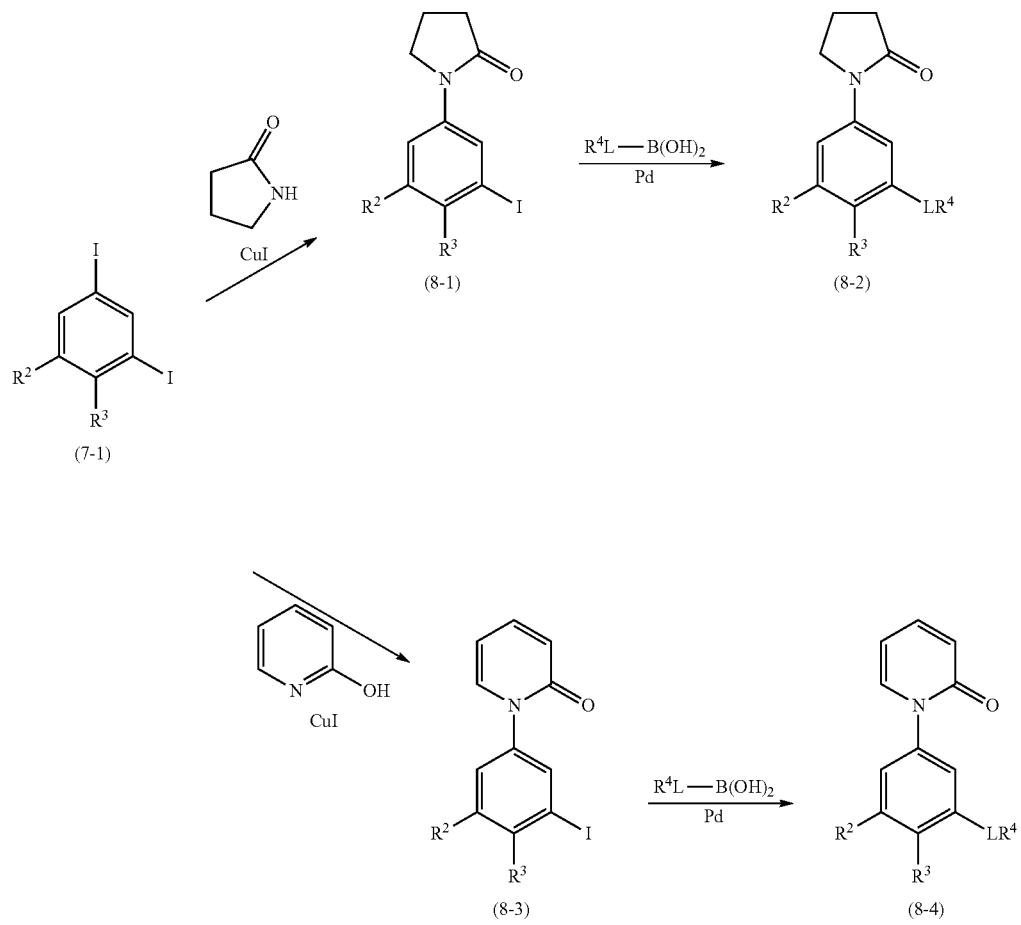

As described in Scheme 8, compounds of formula (8-2) and (8-3), wherein $R^2$ and $R^3$ are described in the Summary of the Invention and L-$R^4$ is aryl, heteroaryl, styrylaryl or styrylheteroaryl, can be prepared from compounds of formula (7-1). Accordingly, compounds of formula (7-1) can be selectively reacted in a copper mediated coupling reaction with heterocyclic compounds such as but not limited to 2-pyrrolidone or pyridin-2-ol to furnish compounds of formulas (8-1) and (8-3), respectively. Compounds of formulas (8-1) and (8-3) can then be treated with $R^4$L-B(OH)$_2$ under Suzuki reaction conditions to provide compounds of formulas (8-2) and (8-4), respectively. Compounds of formulas (8-2) and (8-4) are representative of compounds of formula (I).

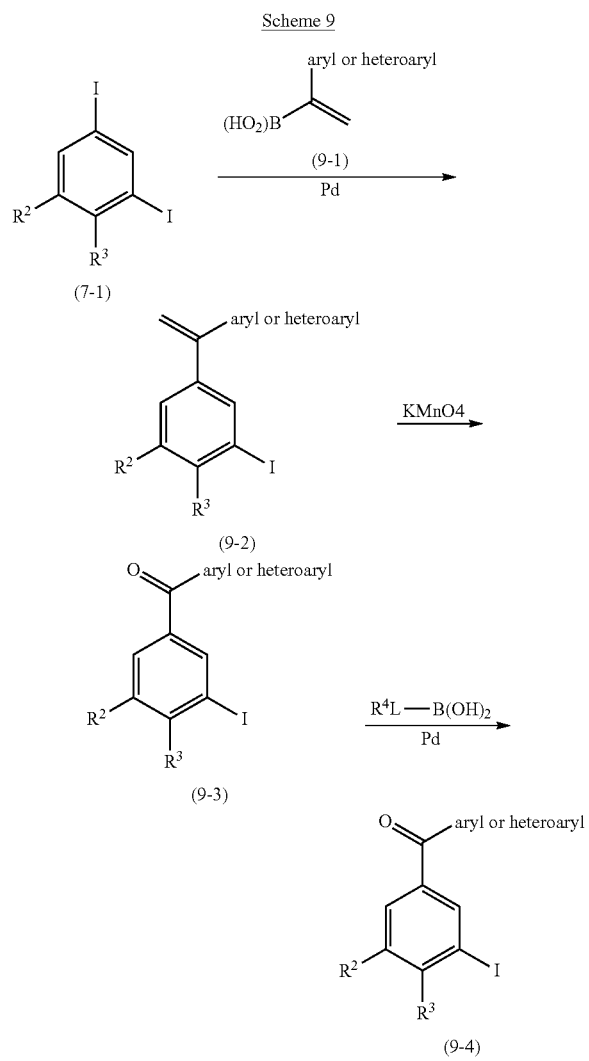

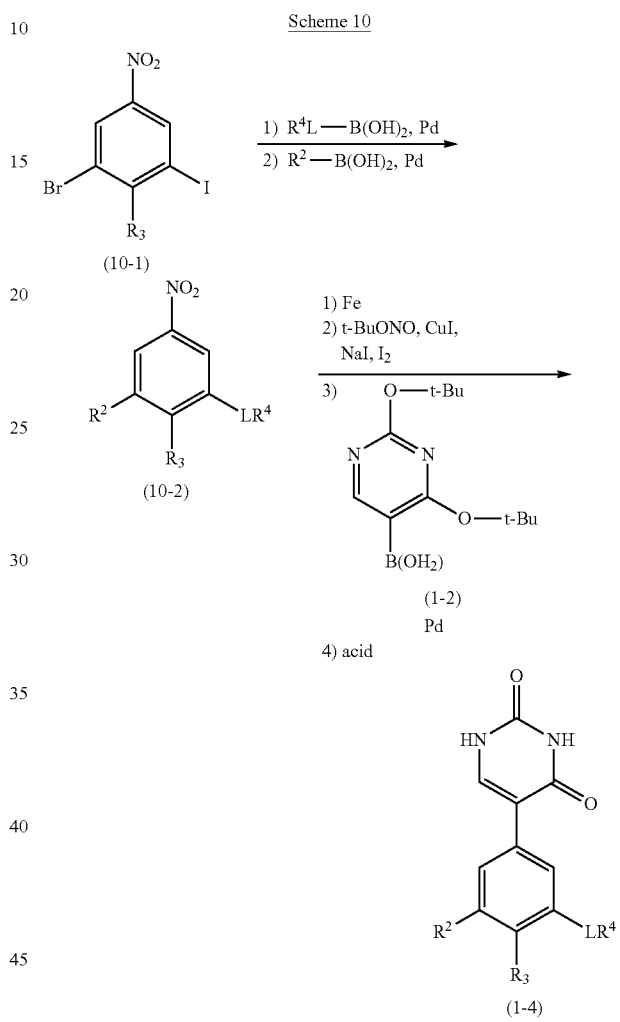

As depicted in Scheme 9, compounds of formula (9-4), wherein $R^2$ and $R^3$ are described in the Summary of the Invention and L-$R^4$ is aryl, heteroaryl, styrylaryl or styrylheteroaryl, can be prepared from compounds of formula (7-1). Compounds of formula (7-1) can be reacted under Suzuki reaction conditions with compounds of formula (9-1) to supply compounds of formula (9-2). Oxidation of compounds of formula (9-2) to give compounds of formula (9-3) can be achieved with a reagent such as potassium permanganate. Compounds of formulas (9-3) can then be treated with $R^4$L-B(OH)$_2$ under Suzuki reaction conditions to provide compounds of formulas (9-4). Compounds of formulas (9-4) are representative of compounds of formula (I).

As depicted in Scheme 10, compounds of formula (1-4), wherein $R^2$ is aryl or heteroaryl, $R^3$ is described in the Summary of the Invention and L-$R^4$ is aryl, heteroaryl, styrylaryl or styrylheteroaryl, can be prepared from compounds of formula (10-1). Compounds of formula (10-1) can be reacted in two sequential Suzuki reaction to deliver compounds of formula (10-2). The nitro group of compounds of formula (10-2) can then be reduced to the corresponding aniline by reduction with iron. The aniline can then be treated with t-butyl nitrite to convert the aniline to the corresponding diazonium salt which in the presence of iodide ions converts to the corresponding aryl iodide. Suzuki reaction with compounds of formula (1-2) followed by treatment with acid give compounds of formula (1-4). Compounds of formula (1-4) are representative of compounds of formula (I).

Scheme 11

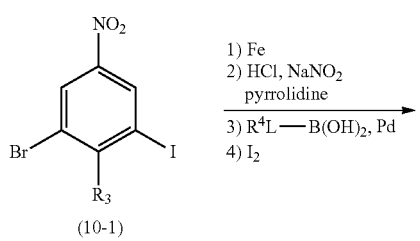
(10-1)

1) Fe
2) HCl, NaNO$_2$
 pyrrolidine
3) R$^4$L—B(OH)$_2$, Pd
4) I$_2$

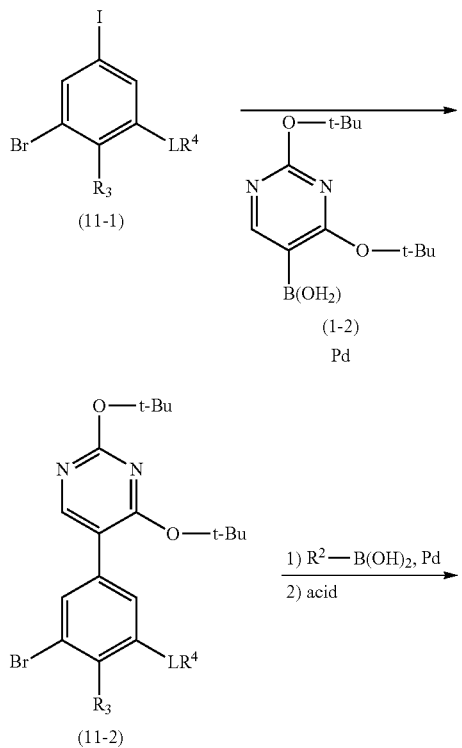

Scheme 12

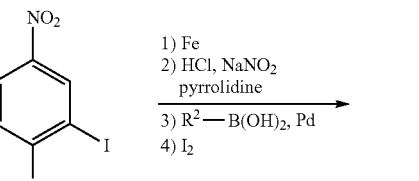
(10-1)

1) Fe
2) HCl, NaNO$_2$
 pyrrolidine
3) R$^2$—B(OH)$_2$, Pd
4) I$_2$

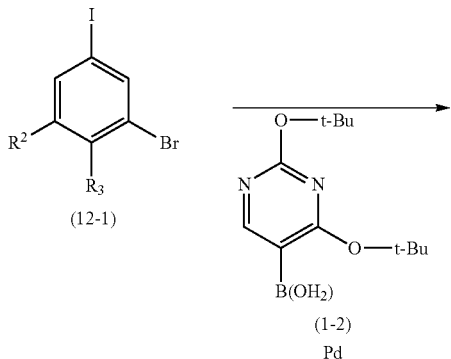

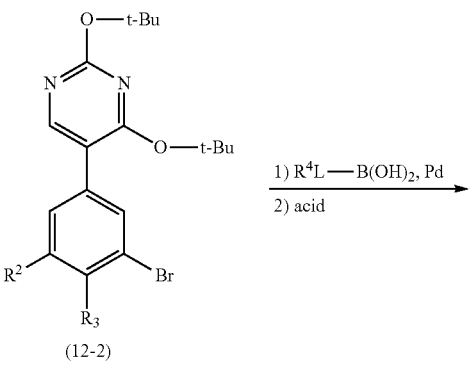

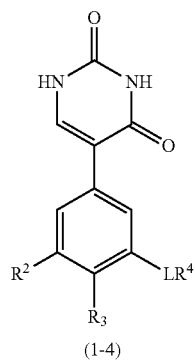

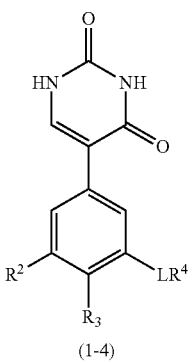

pyrrolinyldiazene. Suzuki reaction conditions deliver L-R$^4$ group. Then treatment with iodine delivers aryliodides of formula (11-1). Suzuki reaction between compounds of formulas (11-1) and (1-2) gives compounds of formula (11-2). Another Suzuki reaction installs R$^2$ and after acid conversion to the uracil, compounds of formula (1-4) are obtained. Compounds of formula (1-4) are representative of compounds of formula (I).

As depicted in Scheme 11, compounds of formula (1-4), wherein R$^2$ is aryl or heteroaryl, R$^3$ is described in the Summary of the Invention and L-R$^4$ is aryl, heteroaryl, styrylaryl or styrylheteroaryl, can be prepared from compounds of formula (10-1) using an alternative sequence. The nitro group in compounds of formula (10-1) can be converted to the corresponding pyrrolinyldiazene in a two step procedure. Initial reduction of the nitro group to an aniline can be achieved with iron, and then treatment with sodium nitrite and pyrrolidine under acid conditions deliver the As depicted in Scheme 12, compounds of formula (1-4), wherein R² is aryl or heteroaryl, R³ is described in the Summary of the Invention and L-R⁴ is aryl, heteroaryl, styrylaryl or styrylheteroaryl, can be prepared from compounds of formula (10-1). The chemical sequence is essentially the same as that described in Scheme 11 except the order of introduction of the R² and L-R⁴ groups is reversed and is useful when it is desirable to introduce the L-R⁴ group later in the synthetic sequence. The sequence gives compounds of formula (1-4) which are representative of compounds of formula (I).

EXAMPLES

The following examples are merely illustrative, and not limiting to this disclosure in any way.

Example 1

Preparation of N-(6-(3-tert-butyl-5-(2,4-dioxo-1,2,3,4-tetrahydropyrimidin-5-yl)-4-methoxyphenyl)naphthalen-2-yl)methanesulfonamide

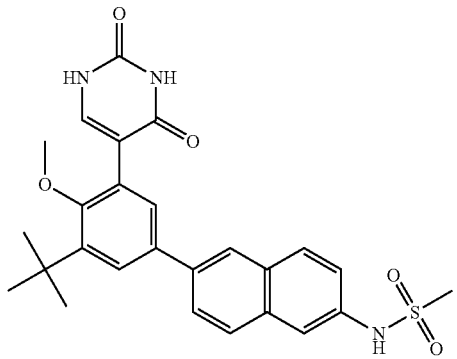 [SMILES: COc1c(-c2c[nH]c(=O)[nH]c2=O)cc(-c2ccc3cc(NS(C)(=O)=O)ccc3c2)cc1C(C)(C)C]

Part A

Preparation of 1-bromo-3-tert-butyl-5-iodo-2-methoxybenzene

A solution of 2-bromo-6-tert-butyl-4-iodophenol (5.0 g, 14.08 mmol) in acetone (50 mL) was treated with potassium carbonate (2.92 g, 21.13 mmol) and dimethylsulfate (1.95 g, 15.49 mmol) at reflux for 16 hours, cooled and concentrated. The residue was dissolved in ethyl acetate, washed with water, brine, dried (Na₂SO₄), filtered and concentrated in vacuo. The crude product was purified on an Isco 40 g silica cartridge eluting with 2% ethyl acetate in hexane to give the title compound.

Part B

Preparation of N-(6-(3-bromo-5-tert-butyl-4-methoxyphenyl)naphthalen-2-yl)methanesulfonamide In a 20 mL microwave tube was mixed the product from Part A (185 mg, 0.5 mmol), N-(6-(4,4,5,5-tetramethyl-1,3,2-dioxaborolan-2-yl)naphthalene-2-yl)methanesulfonamide (182 mg, 0.525 mmol), 1,3,5,7-tetramethyl-6-phenyl-2,4,8-trioxa-6-phosphaadamantane (4.38 mg, 0.015 mmol), potassium phosphate (223 mg, 1.050 mmol) and tris(dibenzylideneacetone) dipalladium(0) (4.58 mg, 5.00 μmol) in tetrahydrofuran (6.0 mL) and water (2.0 mL). The tube was sealed and the mixture was sparged with nitrogen for 5 minutes and then stirred for 4 hours. The reaction mixture was partitioned with ethyl acetate and 1 M HCl. The organic layer was washed with saturated NaHCO₃, brine, dried (Na₂SO₄) and filtered. The filtrate was treated with 3-mercaptopropyl functionalized silica gel (Aldrich catalog #538086), filtered through diatomaceous earth and concentrated in vacuo. The crude product was purified on an Isco 12 g silica cartridge eluting with 4:1 hexane/ethyl acetate to give title compound.

Part C

Preparation of N-(6-(3-tert-butyl-5-(2,4-di-tert-butoxypyrimidin-5-yl)-4-methoxy phenyl)naphthalen-2-yl)methanesulfonamide In a 5 mL microwave tube was added the product from Part B (0.053 g, 0.115 mmol), the product from Example 28 Part B (0.031 g, 0.115 mmol), potassium phosphate (0.049 g, 0.229 mmol) and 1,1'-bis(di-tert-butylphosphino)ferrocene palladium dichloride (3.74 mg, 5.73 μmol) in a solvent mix of tetrahydrofuran (3.0 mL) and water (1.0 mL). The tube was sealed and the mixture was sparged with nitrogen for 5 minutes and then stirred at 50° C. for 16 hours. The reaction mixture was cooled, partitioned with ethyl acetate and 1 M HCl. The organic layer was washed with saturated NaHCO₃, brine, dried (Na₂SO₄) and filtered. The filtrate was treated with 3-mercaptopropyl functionalized silica gel, filtered through diatomaceous earth and concentrated in vacuo. The crude product was purified on an Isco 12 g silica cartridge eluting with 30% ethyl acetate in hexane to give title compound.

Part D

Preparation of N-(6-(3-tert-butyl-5-(2,4-dioxo-1,2,3,4-tetrahydropyrimidin-5-yl)-4-methoxyphenyl)naphthalen-2-yl)methanesulfonamide The product from Part C (38 mg, 0.063 mmol) was treated with a mixture of methanol, concentrated HCl, and water (2.0 mL, 1.0 mL, 1.0 mL) to give a colorless solution followed by rapid formation of a white solid. The mixture was stirred for 1 hour and the solid was collected by filtration, washed with water and diethyl ether and dried to constant mass to give the title compound. ¹H NMR (300 MHz, DMSO-d₆) δ ppm 1.44 (s, 9H) 3.07 (s, 3H) 3.55 (s, 3H) 7.40 (dd, J=8.82, 2.21 Hz, 1H) 7.47-7.53 (m, 2H) 7.59 (d, J=2.21 Hz, 1H) 7.69 (d, J=1.84 Hz, 1H) 7.78 (dd, J=8.64, 1.65 Hz, 1H) 7.91 (d, J=8.82 Hz, 1H) 7.98 (d, J=8.82 Hz, 1H) 8.10 (s, 1H) 9.99 (s, 1H) 11.09 (dd, J=5.88, 1.84 Hz, 1H) 11.31 (d, J=1.84 Hz, 1H).

Example 2

Preparation of N-((6-(3-tert-butyl-5-(2,4-di-tert-butoxypyrimidin-5-yl)-2-methoxyphenyl)benzo[b]thiophen-3-yl)methyl)-N-(2,4-dimethoxybenzyl)methanesulfonamide

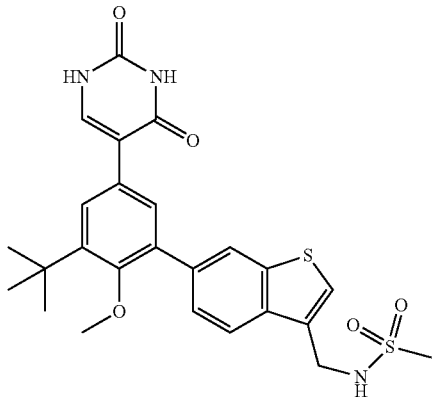 [SMILES: COc1c(-c2ccc3c(CNS(C)(=O)=O)csc3c2)cc(-c2c[nH]c(=O)[nH]c2=O)cc1C(C)(C)C]

Part A

Preparation of 5-(3-bromo-5-tert-butyl-4-methoxyphenyl)-2,4-di-tert-butoxypyrimidine To a 25 mL round-bottomed flask was added the product from Example 1 Part A (36 mg, 1.0 mmol), the product from Example 28 Part B (295 mg, 1.1 mmol), potassium phosphate (446 mg, 2.1 mmol), 1,3,5,7-tetramethyl-6-phenyl-2,4,8-trioxa-6-phosphaadamantane (8.77 mg, 0.030 mmol) and tris(dibenzylideneacetone)dipalladium(0) (9.16 mg, 10.0 μmol) in tetrahydrofuran (6.0 mL) and water (2.0 mL). The mixture was purged with nitrogen for 5 minutes and stirred at room temperature for 4 hours. The reaction mixture was partitioned with ethyl acetate and 0.1 M HCl. The organic layer was washed with saturated $NaHCO_3$, brine, dried ($Na_2SO_4$), filtered and the filtrate was treated with 3-mercaptopropyl functionalized silica gel, filtered and concentrated in vacuo. The crude product was purified by silica gel flash chromatography eluting with ethyl acetate/hexane (0% to 5%) to give the title compound.

Part B

Preparation of N-((6-(3-tert-butyl-5-(2,4-di-tert-butoxypyrimidin-5-yl)-2-methoxy phenyl)benzo[b]thiophen-3-yl)methyl)-N-(2,4-dimethoxybenzyl)methanesulfonamide The product from Part A (46.5 mg, 0.10 mmol) and N-(2,4-dimethoxybenzyl)-N-((6-(4,4,5,5-tetramethyl-1,3,2-dioxaborolan-2-yl)benzo[b]thiophen-3-yl)methyl)methanesulfonamide (51.7 mg, 0.100 mmol) were reacted in the same manner as Example 1 Part C at 50° C. for 2 hours to give crude product which was purified by silica gel flash chromatography eluting with ethyl acetate/hexane (10% to 25%) to give the title compound.

Part C

Preparation of N-((6-(3-tert-butyl-5-(2,4-di-tert-butoxypyrimidin-5-yl)-2-methoxy phenyl)benzo[b]thiophen-3-yl)methyl)-N-(2,4-dimethoxybenzyl)methanesulfonamide To a 25 mL round-bottomed flask was added the product from Part B (58 mg, 0.075 mmol) and trifluoroacetic acid (1.0 mL, 12.98 mmol) in dichloromethane (4 mL). The mixture was stirred at room temperature for 1 hour. The solvent was concentrated in vacuo and the product was triturated with 1% methanol/dichloromethane to give the title compound. $^1$H NMR (300 MHz, DMSO-$d_6$) δ ppm 1.42 (s, 9H) 2.95 (s, 3H) 3.19 (s, 3H) 4.44 (d, J=6.25 Hz, 2H) 7.38 (d, J=2.21 Hz, 1H) 7.47 (d, J=2.21 Hz, 1H) 7.62 (m, 2H) 7.70 (m, 2H) 8.00 (d, J=8.46 Hz, 1H) 8.13 (d, J=1.02 Hz, 1H) 11.12 (dd, J=5.88, 1.84 Hz, 1H) 11.22 (d, J=1.84 Hz, 1H).

Example 3

Preparation of N-((6-(3-tert-butyl-5-(2,4-dioxo-1,2,3,4-tetrahydropyrimidin-5-yl)-2-methoxyphenyl)-1H-inden-3-yl)methyl)methanesulfonamide

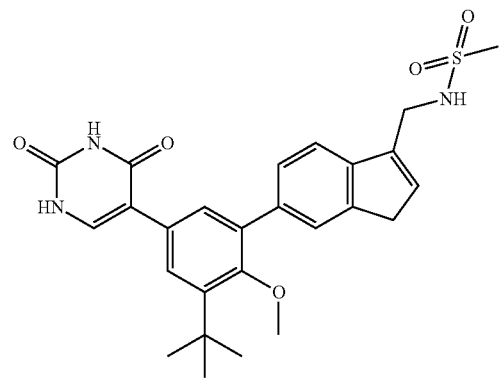 [SMILES: COc1c(-c2ccc3c(c2)CC=C3CNS(C)(=O)=O)cc(-c2c[nH]c(=O)[nH]c2=O)cc1C(C)(C)C]

Part A

Preparation of N-((6-(3-tert-butyl-5-(2,4-di-tert-butoxypyrimidin-5-yl)-2-methoxy phenyl)-1H-inden-3-yl)methyl)methanesulfonamide The product from Example 2 Part A (55.9 mg, 0.12 mmol) and N-((6-(4,4,5,5-tetramethyl-1,3,2-dioxaborolan-2-yl)-1H-inden-3-yl)methyl)methanesulfonamide (41.9 mg, 0.120 mmol) were reacted in the same manner as Example 2 Part B. The crude product was purified by silica gel flash chromatography eluting with ethyl acetate/hexane (5% to 25%) to give the title compound.

Part B

Preparation of N-((6-(3-tert-butyl-5-(2,4-dioxo-1,2,3,4-tetrahydropyrimidin-5-yl)-2-methoxyphenyl)-1H-inden-3-yl)methyl)methanesulfonamide To a 25 mL round-bottomed flask was added the product from Part A (33 mg, 0.054 mmol) in the mixed solvent of methanol (2 mL) and 5 M HCl (2 mL). The mixture was stirred at room temperature for 1 hour, filtered, washed with water, diethyl ether and dried to give the title compound. $^1$H NMR (300 MHz, DMSO-d$_6$) δ ppm 1.41 (s, 9H) 2.96 (s, 3H) 3.20 (s, 3H) 3.46 (s, 2H) 4.18 (d, J=5.15 Hz, 2H) 6.54 (s, 1H) 7.32 (d, J=2.21 Hz, 1H) 7.41 (d, J=2.21 Hz, 1H) 7.49 (m, 2H) 7.57 (d, J=7.71 Hz, 1H) 7.64 (s, 1H) 7.66 (s, 1H) 11.09 (s, 1H) 11.19 (s, 1H).

Example 4

Preparation of (E)-N-(4-(3-tert-butyl-5-(2,4-dioxo-1,2,3,4-tetrahydro pyrimidin-5-yl)-2-methoxystyryl)phenyl)methanesulfonamide

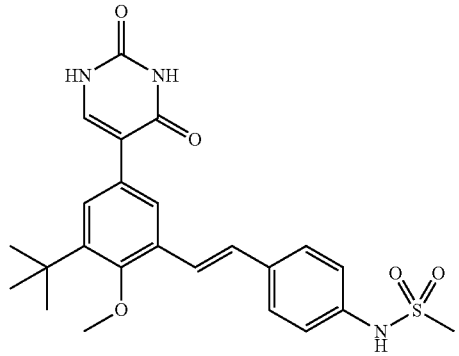 [SMILES: COc1c(/C=C/c2ccc(NS(C)(=O)=O)cc2)cc(-c2c[nH]c(=O)[nH]c2=O)cc1C(C)(C)C]

Part A

Preparation of (E)-N-(4-(3-tert-butyl-5-(2,4-di-tert-butoxypyrimidin-3-yl)-2-methoxy styryl)phenyl)methanesulfonamide The product from Example 2 Part A (55.9 mg, 0.12 mmol) and (E)-4-(methylsulfonamido) styrylboronic acid (28.9 mg, 0.120 mmol) were reacted in the same manner as Example 2 Step B. The crude product was purified by silica gel flash chromatography eluting with ethyl acetate/hexane (5% to 25%) to give the title compound.

Part B

Preparation of (E)-N-(4-(3-tert-butyl-5-(2,4-dioxo-1,2,3,4-tetrahydropyrimidin-5-yl)-2-methoxystyryl)phenyl)methanesulfonamide The product from Part A (39 mg, 0.067 mmol) was reacted in the same manner as Example 3 Step B to give the title compound. $^1$H NMR (300 MHz, DMSO-d$_6$) δ ppm 1.38 (s, 9H) 3.01 (s, 3H) 3.74 (s, 3H) 7.21 (m, 4H) 7.38 (d, J=2.21 Hz, 1H) 7.62 (d, J=8.46 Hz, 2H) 7.66 (m, 2H) 9.83 (s, 1H) 11.12 (s, 1H) 11.22 (s, 1H).

Example 5

Preparation of 5-(3-bromo-5-tert-butyl-4-methoxyphenyl)pyrimidine-2,4(1H,3H)-dione

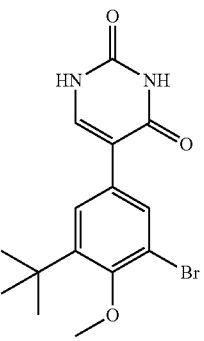 [SMILES: COc1c(Br)cc(-c2c[nH]c(=O)[nH]c2=O)cc1C(C)(C)C]

The product from Example 2 Part A (56 mg, 0.120 mmol) was reacted in the same manner as Example 2 Part C and the crude product was triturated with 1% methanol/dichloromethane to give the title compound. $^1$H NMR (300 MHz, DMSO-d$_6$) δ ppm 1.36 (s, 9H) 3.85 (s, 3H) 7.44 (d, J=2.21 Hz, 1H) 7.68 (d, J=2.21 Hz, 1H) 7.70 (s, 1H) 11.19 (s, 1H) 11.25 (s, 1H).

Example 6

N-((6-(3-tert-butyl-2-methoxy-5-(1-methyl-2,4-dioxo-1,2,3,4-tetrahydro pyrimidin-5-yl)phenyl)-1H-inden-3-yl)methyl)methanesulfonamide

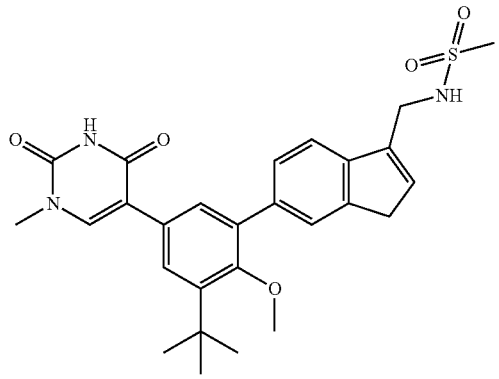 [SMILES: COc1c(-c2ccc3c(c2)CC=C3CNS(C)(=O)=O)cc(-c2cn(C)c(=O)[nH]c2=O)cc1C(C)(C)C]

Part A

Preparation of 1: 5-(3-bromo-5-tert-butyl-4-methoxyphenyl)-1-methylpyrimidine-2,4(1H,3H)-dione and 2: 5-(3-bromo-5-tert-butyl-4-methoxyphenyl)-1,3-dimethylpyrimidine-2,4(1H, 3H)-dione The product from Example 5 (750 mg, 2.123 mmol) and sodium hydroxide (2.336 mL, 2.336 mmol) were combined in N,N-dimethylformamide (10 mL). Dimethyl sulfate (0.223 mL, 2.336 mmol) was added and stirred for 2 hours. The reaction mixture was partitioned with ethyl acetate and H$_2$O. The organic layer was washed with brine, dried (Na₂SO₄), filtered and concentrated in vacuo to give crude product which was purified by silica gel flash chromatography eluting with methanol/dichloromethane (1% to 5%) to give the title compound 1 and title compound 2.

Part B

N-((6-(3-tert-butyl-2-methoxy-5-(1-methyl-2,4-dioxo-1,2,3,4-tetrahydropyrimidin-5-yl)phenyl)-1H-inden-3-yl)methyl)methanesulfonamide The product from Part A (compound 1) (55.1 mg, 0.15 mmol) and N-((6-(4,4,5,5-tetra methyl-1,3,2-dioxaborolan-2-yl)-1H-inden-3-yl)methyl)methanesulfonamide (52.4 mg, 0.150 mmol) were reacted in the same manner as Example 2 Part B to give crude product which was purified by silica gel flash chromatography eluting with ethyl acetate/hexane (20% to 60%) to give the title compound. $^1$H NMR (300 MHz, DMSO-d₆) δ ppm 1.41 (s, 9H) 2.96 (s, 3H) 3.21 (s, 3H) 3.31 (s, 3H) 3.47 (s, 2H) 4.18 (d, J=4.78 Hz, 2H) 6.55 (s, 1H) 7.35 (d, J=2.21 Hz, 1H) 7.46 (d, J=2.21 Hz, 1H) 7.50 (m, 2H) 7.58 (d, J=8.01 Hz, 1H) 7.64 (s, 1H) 7.94 (s, 1H) 11.41 (s, 1H).

Example 7

N-(6-(3-tert-butyl-2-methoxy-5-(1-methyl-2,4-dioxo-1,2,3,4-tetrahydro pyrimidin-5-yl)phenyl)naphthalen-2-yl)methanesulfonamide The product from Example 6 Part A (compound 1) (55.1 mg, 0.15 mmol) and N-(6-(4,4,5,5-tetramethyl-1,3,2-dioxaborolan-2-yl)naphthalene-2-yl)methanesulfonamide (52.1 mg, 0.150 mmol) were reacted in the same manner as Example 2 Part B to give crude product which was triturated with methanol/dichloromethane to give the title compound. $^1$H NMR (300 MHz, DMSO-d₆) δ ppm 1.43 (s, 9H) 3.08 (s, 3H) 3.21 (s, 3H) 3.32 (s, 3H) 7.41 (dd, J=8.82, 2.21 Hz, 1H) 7.45 (d, J=2.21 Hz, 1H) 7.51 (d, J=2.57 Hz, 1H) 7.68 (dd, J=8.46, 1.47 Hz, 1H) 7.72 (d, J=1.84 Hz, 1H) 7.93 (d, J=8.46 Hz, 1H) 7.98 (m, 3H) 10.02 (s, 1H) 11.42 (s, 1H).

Example 8

N-(6-(3-tert-butyl-5-(1,3-dimethyl-2,4-dioxo-1,2,3,4-tetrahydropyrimidin-5-yl)-2-methoxyphenyl)naphthalen-2-yl)methanesulfonamide

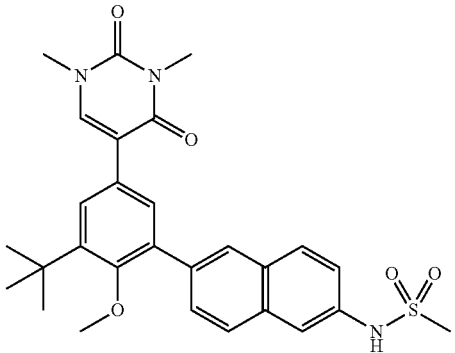 [SMILES: COc1c(-c2ccc3cc(NS(C)(=O)=O)ccc3c2)cc(-c2cn(C)c(=O)n(C)c2=O)cc1C(C)(C)C]

The product from Example 6 Part A (compound 2) (57.2 mg, 0.15 mmol) and N-(6-(4,4,5,5-tetramethyl-1,3,2-dioxaborolan-2-yl)naphthalene-2-yl)methanesulfonamide (52.1 mg, 0.150 mmol) were reacted in the same manner as Example 2 Part B to give crude product which was triturated with methanol/dichloromethane to give the title compound. $^1$H NMR (300 MHz, DMSO-d₆) δ ppm 1.43 (s, 9H) 3.08 (s, 3H) 3.22 (s, 3H) 3.25 (s, 3H) 3.39 (s, 3H) 7.41 (dd, J=8.82, 2.21 Hz, 1H) 7.45 (d, J=2.21 Hz, 1H) 7.53 (d, J=2.57 Hz, 1H) 7.69 (dd, J=8.46, 1.47 Hz, 1H) 7.72 (d, J=1.84 Hz, 1H) 7.93 (d, J=8.46 Hz, 1H) 7.97 (d, J=8.82 Hz, 1H) 8.00 (s, 1H) 8.03 (s, 1H) 10.02 (s, 1H).

Example 9

Preparation of N-(6-(3-tert-butyl-2-methoxy-5-(2-oxo-1,2-dihydropyridin-3-yl)phenyl)naphthalen-2-yl)methanesulfonamide

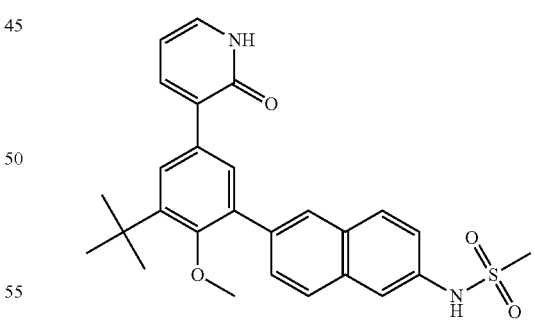

Part A

Preparation of 3-bromo-2-tert-butoxypyridine

To a solution of 3-bromo-2-fluoropyridine (500 mg, 2.84 mmol) in anhydrous tetrahydrofuran (10 mL) under nitrogen was added potassium tert-butoxide (540 mg, 4.8 mmol) in portions over 30 minutes at 25° C., and stirring was continued for 4 hours at 25° C. The mixture was concentrated in vacuo and purified by silica gel flash chromatography eluting with dichloromethane/hexanes (50% to 100%) to give the title compound.

Part B

Preparation of 2-tert-butoxypyridin-3-ylboronic acid

To a solution of the product from Part A (540 mg, 2.347 mmol) in anhydrous tetrahydrofuran (10 mL) under nitrogen at −78° C. was added 1.6M butyllithium in hexanes (1.760 mL, 2.82 mmol) dropwise. The solution was stirred for 10 minutes and treated dropwise with a solution of tributyl borate (0.886 mL, 3.29 mmol) in anhydrous tetrahydrofuran (2 mL), stirred at −78° C. for 3 hours, then allowed to warm to 0° C., cooling the reaction in an ice bath. The reaction mixture was treated with cold 1 M HCl (2.35 mL), followed by ice cold $H_2O$ (5 mL), then the layers were separated and the aqueous phase extracted with diethyl ether. The organic extracts were extracted with cold 2M aqueous NaOH and the combined alkaline phases were neutralized to pH-6 with 6 M aqueous HCl while stirring and cooling in an ice bath, causing the product to precipitate. The solid was collected by filtration and dried to give the title compound.

Part C

Preparation of 3-(3-bromo-5-tert-butyl-4-methoxyphenyl)-2-tert-butoxypyridine

The product from Example 1 Part A (151 mg, 0.410 mmol) and the product from Part B (80 mg, 0.41 mmol) were reacted in the same manner as Example 1 Part B for 48 hours to give crude product which was purified on an Isco 12 g silica cartridge eluting with 5% ethyl acetate in hexane to give the title compound.

Part D

Preparation of N-(6-(5-(2-tert-butoxypyridin-3-yl)-3-tert-butyl-2-methoxyphenyl) naphthalen-2-yl)methanesulfonamide The product from Part C (130 mg, 0.331 mmol) and N-(6-(4,4,5,5-tetramethyl-1,3,2-dioxaborolan-2-yl)naphthalen-2-yl)methanesulfonamide (115 mg, 0.331 mmol) were reacted in the same manner as Example 1 Part C to give crude product which was purified on an Isco 12 g silica cartridge eluting with 10% ethyl acetate in hexane to give the title compound.

Part E

Preparation of N-(6-(3-tert-butyl-2-methoxy-5-(2-oxo-1,2-dihydropyridin-3-yl) phenyl)naphthalen-2-yl)methanesulfonamide The product from Part D (65 mg, 0.122 mmol) was reacted in the same manner as Example 1 Part D to give the title compound. mp>300° C.; $^1$H NMR (300 MHz, DMSO-$d_6$) δ ppm 1.44 (s, 9H) 3.08 (s, 3H) 3.22 (s, 3H) 6.29 (t, J=6.62 Hz, 1H) 7.34-7.38 (m, 1H) 7.41 (dd, J=8.82, 2.21 Hz, 1H) 7.62-7.76 (m, 5H) 7.93 (d, J=8.46 Hz, 1H) 7.97 (d, J=8.82 Hz, 1H) 8.02 (s, 1H) 10.01 (s, 1H) 11.74 (s, 1H).

Example 10

Preparation of N-(6-(3-tert-butyl-2-methoxy-5-(6-oxo-1,6-dihydropyridin-3-yl)phenyl)naphthalen-2-yl)methanesulfonamide

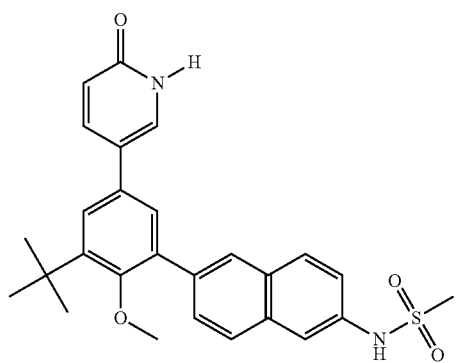 [SMILES: COc1c(-c2ccc3cc(NS(C)(=O)=O)ccc3c2)cc(-c2ccc(=O)[nH]c2)cc1C(C)(C)C]

The title compound was prepared according to the procedure from Example 9 substituting 5-bromo-2-fluoropyridine (1.0 g, 5.57 mmol) for 3-bromo-2-fluoropyridine in Part A to give the title compound. mp>300° C.; $^1$H NMR (300 MHz, DMSO-$d_6$) δ ppm 1.45 (s, 9H) 3.08 (s, 3H) 3.20 (s, 3H) 6.43 (d, J=9.56 Hz, 1H) 7.32-7.46 (m, 3H) 7.70-7.76 (m, 3H) 7.87 (dd, J=9.56, 2.94 Hz, 1H) 7.92 (d, J=8.82 Hz, 1H) 7.97 (d, J=8.82 Hz, 1H) 8.08 (s, 1H) 10.02 (s, 1H) 11.85 (s, 1H).

Example 11

Preparation of N-(6-(5-tert-butyl-2',4'-difluoro-4-methoxybiphenyl-3-yl)naphthalen-2-yl)methanesulfonamide

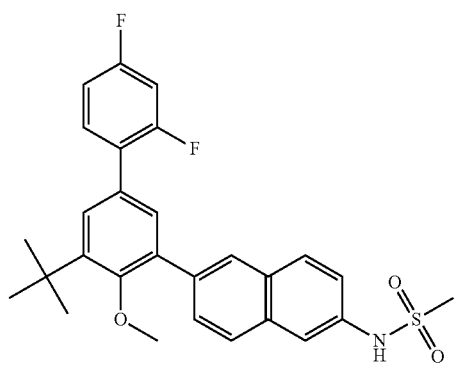 [SMILES: COc1c(-c2ccc3cc(NS(C)(=O)=O)ccc3c2)cc(-c2ccc(F)cc2F)cc1C(C)(C)C]

Part A

Preparation of 3'-bromo-5'-tert-butyl-2,4-difluoro-4'-methoxybiphenyl

The product from Example 1 Part A (0.185 g, 0.501 mmol) and 2-(4,4,5,5-tetramethyl-1,3,2-dioxaborolan-2-yl)-

1,5-difluorobenzene (0.120 g, 0.501 mmol) were reacted in the same manner as Example 1 Part B for 16 hours. The crude product was purified on an Isco 12 g silica cartridge eluting with 5% ethyl acetate in hexane to give the title compound.

Part B

Preparation of N-(6-(5-tert-butyl-2',4'-difluoro-4-methoxybiphenyl-3-yl) naphthalen-2-yl)methanesulfonamide The product from Part A (140 mg, 0.394 mmol) was reacted in the same manner as Example 1 Part C for 16 hours. The crude product was purified on an Isco 40 g silica cartridge eluting with 40% ethyl acetate in hexane to give the title compound. mp 225-228. ° C.; $^1$H NMR (300 MHz, DMSO-d$_6$) δ ppm 1.45 (s, 9H) 3.08 (s, 3H) 3.25 (s, 3H) 7.14-7.23 (m, 1H) 7.32 (d, J=2.57 Hz, 1H) 7.35-7.45 (m, 3H) 7.61-7.77 (m, 3H) 7.90-8.00 (m, 2H) 8.06 (s, 1H) 10.03 (s, 1H).

Example 12

Preparation of 5-(3-tert-butyl-4-methoxy-5-(1-oxo-2,3-dihydro-1H-inden-5-yl)phenyl)pyrimidine-2,4(1H,3H)-dione

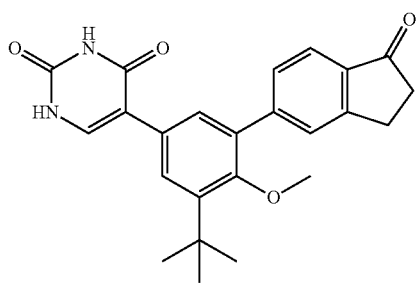 [SMILES: COc1c(-c2ccc3c(c2)CCC3=O)cc(-c2c[nH]c(=O)[nH]c2=O)cc1C(C)(C)C]

Part A

Preparation of 5-(3-tert-butyl-5-(2,4-di-tert-butoxypyrimidin-5-yl)-2-methoxy phenyl)-2,3-dihydro-1H-inden-1-one A solution of Example 2 Part A (0.150 g, 0.32 mmol) and 5-(4,4,5,5-tetramethyl-1,3,2-dioxaborolan-2-yl)-2,3-dihydro-1H-inden-1-one (0.092 g, 0.36 mmol) were reacted in the same manner as Example 50 Part A using 1,1'-bis(diphenylphosphino)ferrocene-palladium(II)dichloride dichloromethane complex as catalyst at 100° C. for 1.5 hours in the microwave and for 4 hours at 100° C. in an oil bath to give crude product which was purified by silica gel flash chromatography eluting with ethyl acetate/hexane (0% to 15%) to give the title compound.

Part B

Preparation of 5-(3-tert-butyl-4-methoxy-5-(1-oxo-2,3-dihydro-1H-inden-5-yl)phenyl)pyrimidine-2,4(1H,3H)-dione A solution of the product from Part A (0.028 g, 0.054 mmol) was reacted in the same manner as Example 1 Part D at room temperature to give the title compound. $^1$H NMR (300 MHz, DMSO-d$_6$) δ ppm 1.41 (s, 9H) 2.65-2.74 (m, 2H) 3.12-3.21 (m, 2H) 3.24 (s, 3H) 7.37 (d, J=2.21 Hz, 1H) 7.50 (d, J=2.21 Hz, 1H) 7.57-7.62 (m, 1H) 7.72 (d, J=8.46 Hz, 3H) 11.13 (s, 1H) 11.23 (s, 1H).

Example 13

Preparation of 5-(3-tert-butyl-5-(1-hydroxy-2,3-dihydro-1H-inden-5-yl)-4-methoxyphenyl)pyrimidine-2,4(1H,3H)-dione

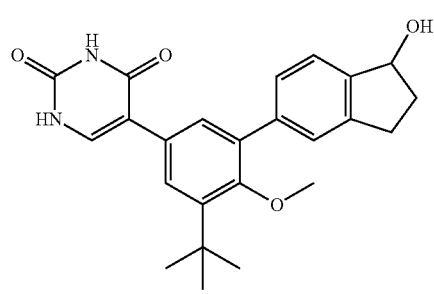 [SMILES: COc1c(-c2ccc3c(c2)CCC3O)cc(-c2c[nH]c(=O)[nH]c2=O)cc1C(C)(C)C]

Part A

Preparation of 5-(5-(2,4-di-tert-butoxypyrimidin-5-yl)-2-methoxy-3-(trifluoromethyl)phenyl)-2,3-dihydro-1H-inden-1-ol A solution of the product from Example 12 Part A (0.082 g, 0.16 mmol) in methanol (1.5 mL) and tetrahydrofuran (1.5 mL) at room temperature was treated with sodium borohydride (0.012 g, 0.32 mmol) and stirred for 1 hour. The solution was poured into 0.1M HCl, extracted into ethyl acetate, dried over sodium sulfate and concentrated in vacuo to give the title compound.

Part B

Preparation of 5-(3-tert-butyl-5-(1-hydroxy-2,3-dihydro-1H-inden-5-yl)-4-methoxyphenyl)pyrimidine-2,4(1H,3H)-dione A solution of the product from Part A (0.025 g, 0.05 mmol) was reacted in the same manner as Example 1 Part D at room temperature to give the title compound. $^1$H NMR (300 MHz, DMSO-d$_6$) δ ppm 1.40 (s, 9H) 2.00 (ddd, J=12.96, 8.73, 4.04 Hz, 1H) 2.27-2.41 (m, J=13.14, 8.00, 6.62, 6.43 Hz, 1H) 2.77-2.90 (m, 1H) 2.96-3.10 (m, 1H) 3.21 (s, 3H) 4.82 (dd, J=6.25, 4.04 Hz, 1H) 7.29 (d, J=2.21 Hz, 1H) 7.35-7.49 (m, 4H) 7.66 (s, 1H) 11.10 (s, 1H) 11.19 (s, 1H).

Example 14

Preparation of N-(6-(3-tert-butyl-2-methoxy-5-ureidophenyl)naphthalen-2-yl)methanesulfonamide

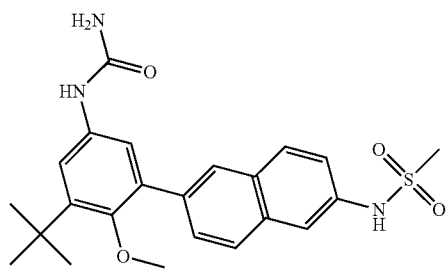 [SMILES: COc1c(-c2ccc3cc(NS(C)(=O)=O)ccc3c2)cc(NC(N)=O)cc1C(C)(C)C]

Part A

Preparation of 1-(3-tert-butyl-5-iodo-4-methoxyphenyl)urea

To a solution of 3-tert-butyl-5-iodo-4-methoxyaniline (915 mg, 3.0 mmol) in dioxane (20 mL) at 0° C. was added chloroacetyl isocyanate (0.256 mL, 3.00 mmol) dropwise to give a solution that was stirred at room temperature for 3 hours. 1,8-Diazabicyclo[5.4.0]undec-7-ene (0.904 mL, 6.00 mmol) was added and the solution was stirred for 18 hours and partitioned between ethyl acetate and 1 M HCl. The ethyl acetate was washed with $H_2O$, brine and dried ($Na_2SO_4$), filtered and concentrated in vacuo. The crude product was purified on an Isco 40 g silica cartridge eluting with methanol/dichloromethane (0% to 5%) to give the title compound.

Part B

Preparation of N-(6-(3-tert-butyl-2-methoxy-5-ureidophenyl)naphthalen-2-yl)methanesulfonamide The product from Part A (52 mg, 0.149 mmol) was reacted in the same manner as Example 1 Part B at 50° C. for 18 hours to give material that was dissolved in hot tetrahydrofuran (10 mL), treated with mercaptopropyl functionalized silica for 30 minutes and filtered through a diatomaceous earth plug. The filtrate was concentrated in vacuo to give the title compound. mp>300° C.; $^1$H NMR (300 MHz, DMSO-$d_6$) δ ppm 1.39 (s, 9H) 3.07 (s, 3H) 3.14 (s, 3H) 5.76 (s, 2H) 7.18 (d, J=2.57 Hz, 1H) 7.40 (dd, J=8.64, 2.02 Hz, 1H) 7.47 (d, J=2.57 Hz, 1H) 7.64 (dd, J=8.46, 1.84 Hz, 1H) 7.71 (d, J=2.21 Hz, 1H) 7.91 (d, J=8.82 Hz, 1H) 7.94 (s, 1H) 7.97 (d, J=8.82 Hz, 1H) 8.49 (s, 1H) 10.00 (s, 1H).

Example 15

Preparation of N-(6-(3-tert-butyl-5-(2-hydroxy-5-oxo-4,5-dihydro-1H-imidazol-1-yl)-2-methoxyphenyl)naphthalen-2-yl)methanesulfonamide

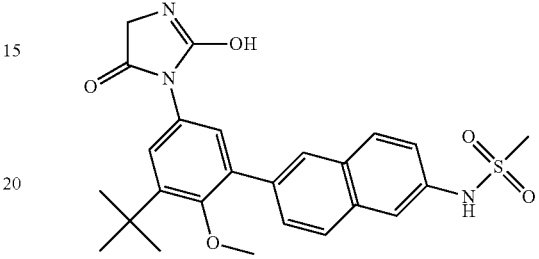

Part A

Preparation of ethyl 2-(3-(3-tert-butyl-5-iodo-4-methoxyphenyl)ureido)acetate

To a solution of 3-tert-butyl-5-iodo-4-methoxyaniline (458 mg, 1.5 mmol) in dioxane (5 mL) was added ethyl isocyanatoacetate (0.168 mL, 1.500 mmol) dropwise producing a solution that was stirred at room temperature for 16 hours. The reaction mixture was concentrated and the product was triturated in 9:1 hexane/ethyl acetate. The resulting solid was collected by filtration and dried to give the title compound.

Part B

Preparation of N-(6-(3-tert-butyl-5-(2-hydroxy-5-oxo-4,5-dihydro-1H-imidazol-1-yl)-2-methoxyphenyl)naphthalen-2-yl)methanesulfonamide The product from Part A (87 mg, 0.2 mmol) was reacted in the same manner as Example 1 Part B at 50° C. for 18 hours. The crude product was purified on an Isco 12 g silica cartridge eluting with methanol/dichloromethane (0.5% to 3%). The collected material was triturated in 1:1:1 methanol/ethyl acetate/hexane and filtered to collect the title compound m.p. 293-295° C.; $^1$H NMR (300 MHz, DMSO-$d_6$) δ ppm 1.42 (s, 9H) 3.08 (s, 3H) 3.25 (s, 3H) 4.05 (s, 2H) 7.27 (s, 2H) 7.42 (dd, J=8.82, 2.21 Hz, 1H) 7.67 (dd, J=8.46, 1.84 Hz, 1H) 7.73 (d, J=1.84 Hz, 1H) 7.89-8.03 (m, 3H) 8.29 (s, 1H) 10.03 (s, 1H).

Example 16

Preparation of N-(6-(3-tert-butyl-5-(2,4-dioxoimidazolidin-1-yl)-2-methoxy phenyl)naphthalen-2-yl)methanesulfonamide

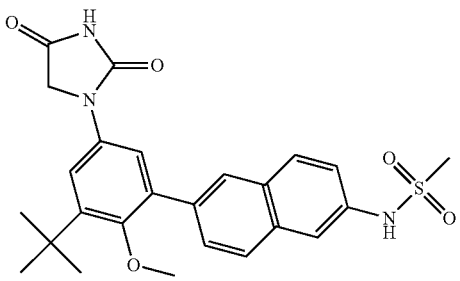 [SMILES: COc1c(-c2ccc3cc(NS(C)(=O)=O)ccc3c2)cc(N2CC(=O)NC2=O)cc1C(C)(C)C]

Part A

Preparation of 1-(3-tert-butyl-5-iodo-4-methoxyphenyl)imidazolidine-2,4-dione 3-tert-Butyl-5-iodo-4-methoxyaniline (915 mg, 3.0 mmol) and chloroacetyl isocyanate (0.256 mL, 3.00 mmol) were reacted in the same manner as Example 14 Part A to give crude product which was purified on an Isco 40 g silica cartridge eluting with methanol/dichloromethane (0% to 5%) to give the title compound.

Part B

Preparation of N-(6-(3-tert-butyl-5-(2,4-dioxoimidazolidin-1-yl)-2-methoxy phenyl)naphthalen-2-yl)methanesulfonamide The product from Part A (78 mg, 0.20 mmol) was reacted in the same manner as Example 1 Part B at 50° C. for 18 hours. The crude product was purified on an Isco 12 g silica cartridge eluting with methanol/dichloromethane (0.5% to 3%) and the resulting material was then triturated in 3:1 ethyl acetate/hexane and filtered to give the title compound. m.p. 280° C.; $^1$H NMR (300 MHz, DMSO-$d_6$) δ ppm 1.41 (s, 9H) 3.08 (s, 3H) 3.17 (s, 3H) 4.52 (s, 2H) 7.38-7.45 (m, 2H) 7.62 (d, J=2.57 Hz, 1H) 7.64-7.74 (m, 2H) 7.90-8.04 (m, 3H) 10.05 (s, 1H) 11.14 (s, 1H).

Example 17

Preparation of N-(6-(3-tert-butyl-2-methoxy-5-(3-phenylureido)phenyl) naphthalen-2-yl)methanesulfonamide

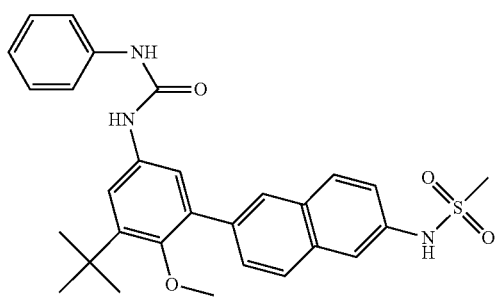 [SMILES: COc1c(-c2ccc3cc(NS(C)(=O)=O)ccc3c2)cc(NC(=O)Nc2ccccc2)cc1C(C)(C)C]

Part A

Preparation of 1-(3-tert-butyl-5-iodo-4-methoxyphenyl)-3-phenylurea 3-tert-Butyl-5-iodo-4-methoxyaniline (305 mg, 1 mmol) and phenyl isocyanate (0.109 mL, 1.000 mmol) were reacted in the same manner as Example 15 Part A to give the title compound.

Part B

Preparation of N-(6-(3-tert-butyl-2-methoxy-5-(3-phenylureido)phenyl) naphthalen-2-yl)methanesulfonamide The product from Part A (85 mg, 0.20 mmol) was reacted in the same manner as Example 1 Part B at 50° C. for 18 hours. The reaction mixture was cooled and the solid was collected by filtration, washed repeatedly with water and the crude product was triturated in 4 mL methanol, the solid collected and dried to give the title compound. m.p.>300; $^1$H NMR (300 MHz, DMSO-$d_6$) δ ppm 1.41 (s, 9H) 3.08 (s, 3H) 3.16 (s, 3H) 6.95 (t, J=7.35 Hz, 1H) 7.21-7.31 (m, 3H) 7.38-7.47 (m, 3H) 7.50 (d, J=2.94 Hz, 1H) 7.67 (dd, J=8.46, 1.84 Hz, 1H) 7.73 (d, J=1.84 Hz, 1H) 7.92 (d, J=8.82 Hz, 1H) 7.96-8.02 (m, 2H) 8.59 (s, 1H) 8.64 (s, 1H) 10.02 (s, 1H).

Example 18

Preparation of N-(6-(3-tert-butyl-5-(3-isopropylureido)-2-methoxyphenyl) naphthalen-2-yl)methanesulfonamide

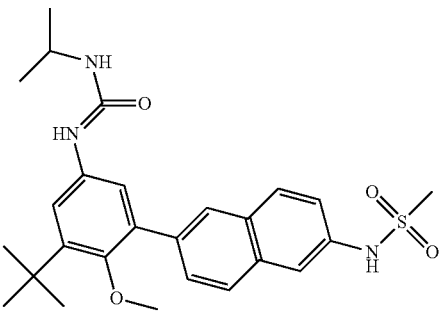

Part A

Preparation of 1-(3-tert-butyl-5-iodo-4-methoxyphenyl)-3-isopropylurea 3-tert-Butyl-5-iodo-4-methoxyaniline (305 mg, 1 mmol) and isopropyl isocyanate were reacted in the same manner as Example 15 Part A to give the title compound

Part B

Preparation of N-(6-(3-tert-butyl-5-(3-isopropylureido)-2-methoxyphenyl) naphthalen-2-yl)methanesulfonamide The product from Part A (78 mg, 0.20 mmol) was reacted in the same manner as Example 1 Part B at 50° C. for 18 hours. The crude product was triturated in 4 mL 1:1 ethyl acetate/methanol and the solid was collected and dried to give the title compound. m.p.>300; $^1$H NMR (300 MHz, DMSO-$d_6$) δ ppm 1.08 (d, J=6.62 Hz, 6H) 1.39 (s, 9H) 3.07 (s, 3H) 3.14 (s, 3H) 3.64-3.82 (m, 1H) 5.88 (d, J=7.72 Hz, 1H) 7.20 (d, J=2.57 Hz, 1H) 7.39 (d, J=2.21 Hz, 1H) 7.42 (d, J=2.57 Hz, 1H) 7.64 (dd, J=8.46, 1.84 Hz, 1H) 7.71 (d, J=2.21 Hz, 1H) 7.90 (d, J=8.82 Hz, 1H) 7.94 (s, 1H) 7.97 (d, J=9.19 Hz, 1H) 8.26 (s, 1H) 10.01 (s, 1H).

Example 19

Preparation of tert-butyl 2-(3-tert-butyl-4-methoxy-5-(6-(methylsulfonamido) naphthalen-2-yl)phenylamino)-2-oxoethylcarbamate

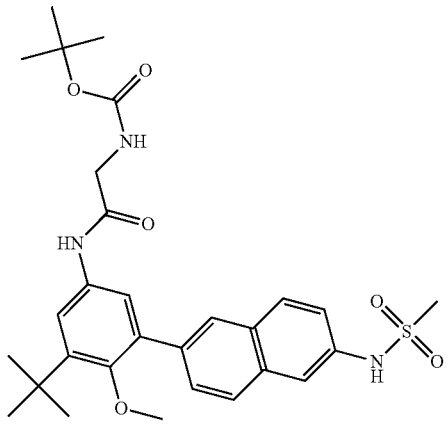 [SMILES: COc1c(-c2ccc3cc(NS(C)(=O)=O)ccc3c2)cc(NC(=O)CNC(=O)OC(C)(C)C)cc1C(C)(C)C]

Part A

Preparation of tert-butyl 2-(3-tert-butyl-5-iodo-4-methoxyphenylamino)-2-oxo ethylcarbamate 3-tert-Butyl-5-iodo-4-methoxyaniline (0.153 g, 0.5 mmol), N-(tert-butoxycarbonyl)glycine (0.096 g, 0.55 mmol), N,N-diisopropylethylamine (0.173 mL, 1.000 mmol) and O-benzotriazol-1-yl-N,N,N',N'-tetramethyluronium tetrafluoroborate (0.177 g, 0.550 mmol) were combined in dimethyl sulfoxide (2.5 mL), stirred for 48 hours and partitioned between ethyl acetate and water. The organic layer was washed with brine, dried (Na$_2$SO$_4$) and concentrated in vacuo. The crude product was purified on an Isco 12 g silica cartridge eluting with ethyl acetate/hexane (0% to 25%) to give the title compound.

Part B

Preparation of tert-butyl 2-(3-tert-butyl-4-methoxy-5-(6-(methylsulfonamido) naphthalen-2-yl)phenylamino)-2-oxoethylcarbamate The product from Part A (230 mg, 0.50 mmol) was reacted in the same manner as Example 1 Part B at 50° C. for 18 hours. The crude product was triturated in 15 mL of 1:1:1 dichloromethane/methanol/ethyl acetate and filtered to remove a small amount of solid. The filtrate was then concentrated and this residue was triturated with 5 mL of 4:1 dichloromethane/methanol mixture and filtered to collect the title compound. mp 221-223° C.; $^1$H NMR (300 MHz, DMSO-$d_6$) δ ppm 1.39 (s, 9H) 1.40 (s, 9H) 3.08 (s, 3H) 3.16 (s, 3H) 3.70 (d, J=5.88 Hz, 2H) 7.03 (t, J=6.07 Hz, 1H) 7.41 (dd, J=8.82, 1.84 Hz, 1H) 7.46 (d, J=2.57 Hz, 1H) 7.60-7.68 (m, 2H) 7.72 (d, J=1.84 Hz, 1H) 7.91 (s, 1H) 7.93-8.02 (m, 2H) 9.88 (s, 1H) 10.02 (s, 1H).

Example 20

Preparation of 2-amino-N-(3-tert-butyl-4-methoxy-5-(6-(methylsulfonamido) naphthalen-2-yl)phenyl) acetamide

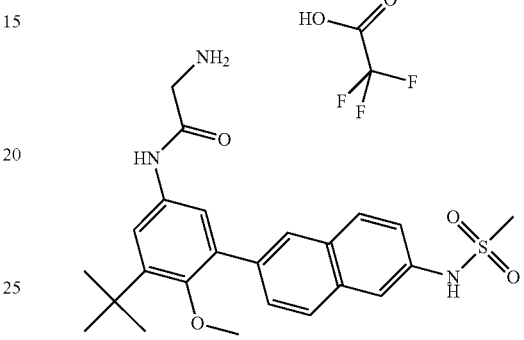

The product from Example 19 Part B (70 mg, 0.126 mmol) was reacted in the same manner as Example 2 Part C to give the title compound as the trifluoroacetic acid salt. $^1$H NMR (300 MHz, DMSO-$d_6$) δ ppm 1.41 (s, 9H) 3.09 (s, 3H) 3.18 (s, 3H) 3.69-3.83 (m, 2H) 7.42 (dd, J=8.82, 2.21 Hz, 1H) 7.50 (d, J=2.57 Hz, 1H) 7.60 (d, J=2.57 Hz, 1H) 7.65 (dd, J=8.46, 1.47 Hz, 1H) 7.73 (d, J=1.84 Hz, 1H) 7.91-8.01 (m, 3H) 8.09 (s, 3H) 10.04 (s, 1H) 10.40 (s, 1H).

Example 21

Preparation of ethyl 3-(3-(3-tert-butyl-4-methoxy-5-(6-(methylsulfonamido) naphthalen-2-yl)phenyl) ureido)propanoate

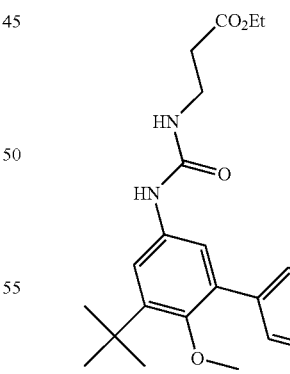

Part A

Preparation of ethyl 3-(3-(3-tert-butyl-5-iodo-4-methoxyphenyl)ureido)propanoate 3-tert-Butyl-5-iodo-4-methoxyaniline (305 mg, 1 mmol) and ethyl 3-isocyanatopropionate were reacted in the same manner as Example 15 Part A and purified on an Isco 40 g silica cartridge eluting with ethyl acetate/hexane (0% to 25%) to give the title compound (373 mg, 83%).

Part B

Preparation of ethyl 3-(3-(3-tert-butyl-4-methoxy-5-(6-(methylsulfonamido) naphthalen-2-yl)phenyl) ureido)propanoate The product from Part A (179 mg, 0.40 mmol) was reacted in the same manner as Example 1 Part B at 50° C. for 18 hours to give a solid that was triturated with 1:1 hexane/ethyl acetate and collected by filtration to give the title compound. m.p.>300° C.; $^1$H NMR (300 MHz, DMSO-$d_6$) δ ppm 1.19 (t, J=7.17 Hz, 3H) 1.39 (s, 9H) 2.44-2.54 (m, 2H) 3.08 (s, 3H) 3.14 (s, 3H) 3.28-3.34 (m, 2H) 4.08 (q, J=6.99 Hz, 2H) 6.15 (t, J=5.88 Hz, 1H) 7.22 (d, J=2.57 Hz, 1H) 7.37-7.46 (m, 2H) 7.64 (dd, J=8.46, 1.47 Hz, 1H) 7.72 (d, J=1.84 Hz, 1H) 7.90 (d, J=8.46 Hz, 1H) 7.94 (s, 1H) 7.97 (d, J=9.19 Hz, 1H) 8.54 (s, 1H) 10.01 (s, 1H).

Example 22

Preparation of N-(6-(3-tert-butyl-5-(3-ethylureido)-2-methoxyphenyl) naphthalen-2-yl)methanesulfonamide

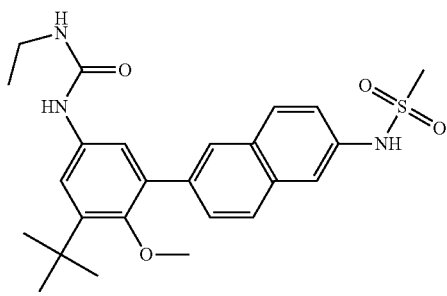 [SMILES: CCNC(=O)Nc1cc(-c2ccc3cc(NS(C)(=O)=O)ccc3c2)c(OC)c(C(C)(C)C)c1]

Part A

Preparation of 1-(3-tert-butyl-5-iodo-4-methoxyphenyl)-3-(2-chloroethyl)urea 3-tert-Butyl-5-iodo-4-methoxyaniline (305 mg, 1 mmol) and ethyl isocyanate were reacted in the same manner as Example 15 Part A to give the title compound.

Part B

Preparation of N-(6-(3-tert-butyl-5-(3-ethylureido)-2-methoxyphenyl)naphthalen-2-yl)methanesulfonamide The product from Part A (113 mg, 0.30 mmol) was reacted in the same manner as Example 1 Part B for 72 hours. The product was triturated in 5 mL of methanol and collected by filtration to give the title compound. mp>300° C.; $^1$H NMR (300 MHz, DMSO-$d_6$) δ ppm 1.04 (t, J=7.17 Hz, 3H) 1.39 (s, 9H) 3.03-3.12 (m, 2H) 3.08 (s, 3H) 3.14 (s, 3H) 6.00 (t, J=5.52 Hz, 1H) 7.23 (d, J=2.94 Hz, 1H) 7.41 (dd, J=8.82, 2.21 Hz, 1H) 7.44 (d, J=2.57 Hz, 1H) 7.64 (dd, J=8.64, 1.65 Hz, 1H) 7.72 (d, J=1.84 Hz, 1H) 7.91 (d, J=8.82 Hz, 1H) 7.94 (s, 1H) 7.97 (d, J=8.82 Hz, 1H) 8.38 (s, 1H) 10.00 (s, 1H).

Example 23

Preparation of tert-butyl 3-(3-tert-butyl-4-methoxy-5-(6-(methylsulfonamido) naphthalen-2-yl)phenylamino)-3-oxopropylcarbamate

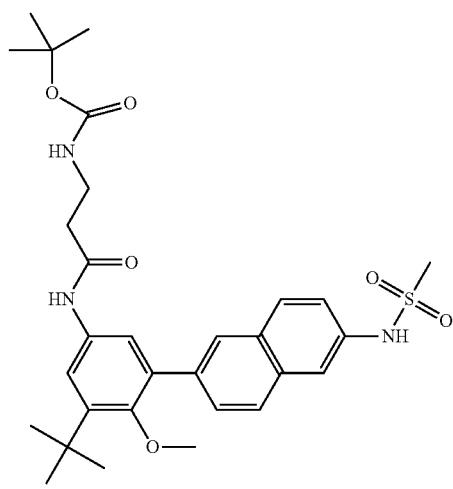 [SMILES: COc1c(-c2ccc3cc(NS(C)(=O)=O)ccc3c2)cc(NC(=O)CCNC(=O)OC(C)(C)C)cc1C(C)(C)C]

Part A

Preparation of 1-(3-tert-butyl-5-iodo-4-methoxyphenyl)-3-(2-chloroethyl)urea 3-tert-Butyl-5-iodo-4-methoxyaniline (305 mg, 1 mmol) and N-(tert-butoxycarbonyl)-Q-alanine (189 mg, 1.000 mmol) were reacted in the same manner as Example 19 Part A for 24 hours. The crude product was purified on an Isco 12 g silica cartridge eluting with 3% methanol in dichloromethane to give the title compound.

Part B

Preparation of tert-butyl 3-(3-tert-butyl-4-methoxy-5-(6-(methylsulfonamido) naphthalen-2-yl)phenylamino)-3-oxopropylcarbamate The product from Part A (100 mg, 0.21 mmol) was reacted in the same manner as Example 1 Part B for 16 hours. The crude product was triturated in dichloromethane to give title compound as a solid that was collected and dried. $^1$H NMR (300 MHz, DMSO-$d_6$) δ ppm 1.37 (s, 9H) 1.40 (s, 9H) 2.44 (t, J=7.17 Hz, 2H) 3.08 (s, 3H) 3.16 (s, 3H) 3.17-3.25 (m, 2H) 6.85 (t, J=5.70 Hz, 1H) 7.41 (dd, J=8.82, 2.21 Hz, 1H) 7.47 (d, J=2.57 Hz, 1H) 7.59-7.73 (m, 3H) 7.92 (d, J=10.66 Hz, 1H) 7.94 (s, 1H) 7.97 (d, J=8.82 Hz, 1H) 9.90 (s, 1H) 10.01 (s, 1H).

Example 24

Preparation of 3-amino-N-(3-tert-butyl-4-methoxy-5-(6-(methylsulfonamido) naphthalen-2-yl)phenyl) propanamide

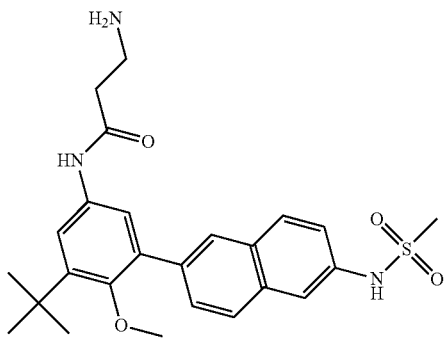 [SMILES: COc1c(-c2ccc3cc(NS(C)(=O)=O)ccc3c2)cc(NC(=O)CCN)cc1C(C)(C)C]

The product from Example 23 (60 mg, 0.105 mmol) was reacted in the same manner as Example 2 Part C to give the title compound. $^1$H NMR (300 MHz, DMSO-$d_6$) δ ppm 1.40 (s, 9H) 2.68 (t, J=6.62 Hz, 2H) 3.02-3.13 (m, 2H) 3.09 (s, 3H) 3.17 (s, 3H) 7.42 (dd, J=8.82, 2.21 Hz, 1H) 7.50 (d, J=2.57 Hz, 1H) 7.60-7.76 (m, 5H) 7.86-8.04 (m, 3H) 10.03 (s, 1H) 10.13 (s, 1H).

Example 25

Preparation of N-(6-(3-tert-butyl-2-methoxy-5-(2-oxooxazolidin-3-yl)phenyl)naphthalen-2-yl)methanesulfonamide

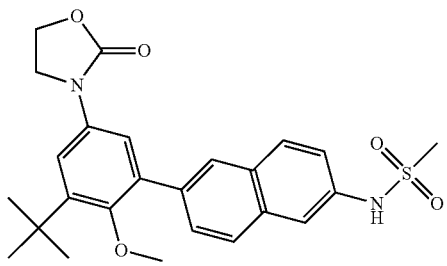 [SMILES: COc1c(-c2ccc3cc(NS(C)(=O)=O)ccc3c2)cc(N2CCOC2=O)cc1C(C)(C)C]

Part A

Preparation of 2-chloroethyl-3-tert-butyl-5-iodo-4-methoxyphenylcarbamate

To a solution of 3-tert-butyl-5-iodo-4-methoxyaniline (0.305 g, 1.0 mmol) in dichloromethane (5.00 mL) was added 2-chloroethyl chloroformate (0.143 g, 1.000 mmol) and triethylamine (0.279 mL, 2.0 mmol) to give a solution. The mixture was stirred for 3 hours and concentrated to give the title compound that was used without purification.

Part B

Preparation of 3-(3-tert-butyl-5-iodo-4-methoxyphenyl)oxazolidin-2-one

The product from Part A (412 mg, 1 mmol) in ethanol (5 mL) was treated with sodium ethoxide (681 mg, 2.100 mmol) and heated at 60° C. for 2 hours, cooled and neutralized to pH 7 with 1 M HCl. The mixture was diluted into water and extracted with ethyl acetate. The organics were combined, washed with brine, dried (Na$_2$SO$_4$) and concentrated. The residue was purified on an Isco 12 g silica cartridge eluting with 2:1 hexane/ethyl acetate to give the title compound.

Part C

Preparation of N-(6-(3-tert-butyl-2-methoxy-5-(2-oxooxazolidin-3-yl)phenyl) naphthalen-2-yl)methanesulfonamide The product from Part B (94 mg, 0.25 mmol) was reacted in the same manner as Example 1 Part B for 16 hours. The crude oil was purified on a 12 g Isco silica cartridge eluting with 2.5% methanol in dichloromethane. The desired fractions were combined and purified a second time on a 12 g Isco silica cartridge eluting with 3:2 hexane/ethyl acetate to give the title compound. mp 216-218° C.; $^1$H NMR (300 MHz, DMSO-$d_6$) δ ppm 1.42 (s, 9H) 3.08 (s, 3H) 3.18 (s, 3H) 4.11 (t, J=7.91 Hz, 2H) 4.42 (t, J=7.91 Hz, 2H) 7.38 (d, J=2.57 Hz, 1H) 7.42 (dd, J=8.82, 2.21 Hz, 1H) 7.57 (d, J=2.57 Hz, 1H) 7.67 (dd, J=8.46, 1.84 Hz, 1H) 7.73 (d, J=1.84 Hz, 1H) 7.93 (d, J=8.46 Hz, 1H) 7.96-8.00 (m, 2H) 10.03 (s, 1H).

Example 26

Preparation of N-(6-(3-tert-butyl-2-methoxy-5-(2-oxotetrahydropyrimidin-1(2H)-yl)phenyl)naphthalen-2-yl)methanesulfonamide

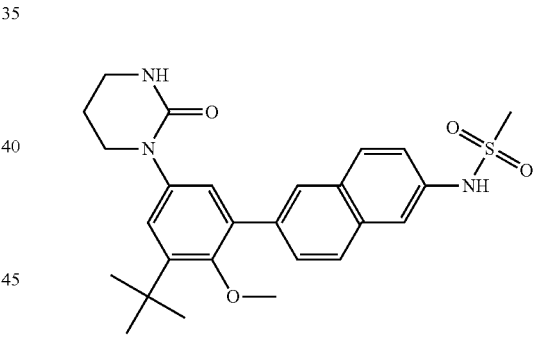

Part A

Preparation of 1-(3-tert-butyl-5-iodo-4-methoxyphenyl)-3-(3-chloropropyl)urea 3-tert-Butyl-5-iodo-4-methoxyaniline (305 mg, 1 mmol) and ethyl 3-chloropropyl isocyanate (0.103 mL, 1.000 mmol) were reacted in the same manner as Example 15 Part A to give the title compound which was used without purification.

Part B

Preparation of 1-(3-tert-butyl-5-iodo-4-methoxyphenyl)tetrahydropyrimidin-2(1H)-one The crude product from Part A (425 mg, 1 mmol) in tetrahydrofuran (2 mL) was treated with potassium tert-butoxide (2.200 mL, 2.200 mmol), stirred 18 hours and partitioned between ethyl acetate and 1 M HCl. The ethyl acetate layer was washed with saturated NaHCO$_3$, H$_2$O, and brine. The organic layer was dried (Na$_2$SO$_4$), filtered and concentrated in vacuo. The crude product was purified on an Isco 12 g silica cartridge eluting with 4:1 hexane/ethyl acetate to give the title compound.

Part C

Preparation of N-(6-(3-tert-butyl-2-methoxy-5-(2-oxotetrahydropyrimidin-1(2H)-yl)phenyl)naphthalen-2-yl)methanesulfonamide The product from Part B (116 mg, 0.30 mmol) was reacted in the same manner as Example 1 Part B for 18 hours, giving the title compound. mp>300° C.; $^1$H NMR (300 MHz, DMSO-d$_6$) δ ppm 1.40 (s, 9H) 1.88-1.98 (m, 2H) 3.07 (s, 3H) 3.19 (s, 3H) 3.19-3.27 (m, 2H) 3.61-3.66 (m, 2H) 6.51 (s, 1H) 7.17 (q, J=2.70 Hz, 2H) 7.40 (dd, J=9.01, 2.02 Hz, 1H) 7.66 (dd, J=8.46, 1.47 Hz, 1H) 7.71 (d, J=1.84 Hz, 1H) 7.89-7.99 (m, 3H) 10.01 (s, 1H).

Example 27

Preparation of N-(6-(3-tert-butyl-2-methoxy-5-(2-oxoimidazolidin-1-yl) phenyl)naphthalen-2-yl)methanesulfonamide

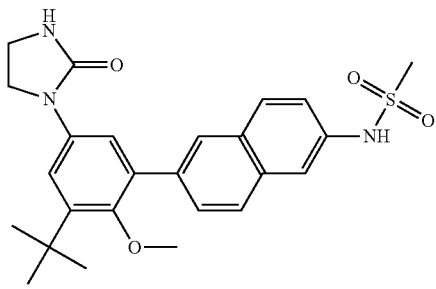 [SMILES: COc1c(-c2ccc3cc(NS(C)(=O)=O)ccc3c2)cc(N2CCNC2=O)cc1C(C)(C)C]

Part A

Preparation of 1-(3-tert-butyl-5-iodo-4-methoxyphenyl)-3-(2-chloroethyl)urea 3-tert-Butyl-5-iodo-4-methoxyaniline (305 mg, 1 mmol) and ethyl 2-chloroethyl isocyanate (0.085 mL, 1.000 mmol) were reacted in the same manner as Example 15 Part A to give the title compound which was used without purification.

Part B

Preparation of 1-(3-tert-butyl-5-iodo-4-methoxyphenyl)imidazolidin-2-one

The crude product from Part A (411 mg, 1 mmol) was reacted in the same manner as Example 26 Part B to give crude product which was purified on an Isco 12 g silica cartridge eluting with 4:1 hexane/ethyl acetate to give the title compound.

Part C

Preparation of N-(6-(3-tert-butyl-2-methoxy-5-(2-oxoimidazolidin-1-yl)phenyl) naphthalen-2-yl)methanesulfonamide The product from Part B (112 mg, 0.30 mmol) was reacted in the same manner as Example 1 Part B for 72 hours. The crude product was triturated in 1:1 ethyl acetate/methanol (5 mL) and the solid collected by filtration to give the title compound. m.p. 284-286° C.; $^1$H NMR (300 MHz, DMSO-d$_6$) δ ppm 1.41 (s, 9H) 3.08 (s, 3H) 3.15 (s, 3H) 3.34-3.43 (m, 2H) 3.85-3.93 (m, 2H) 6.87 (s, 1H) 7.36 (d, J=2.57 Hz, 1H) 7.41 (dd, J=8.82, 2.21 Hz, 1H) 7.56 (d, J=2.57 Hz, 1H) 7.66 (dd, J=8.46, 1.47 Hz, 1H) 7.72 (d, J=1.84 Hz, 1H) 7.92 (d, J=8.82 Hz, 1H) 7.97 (d, J=8.09 Hz, 2H) 10.01 (s, 1H).

Example 28

Preparation of N-(6-(3-tert-butyl-5-(2,4-dioxo-1,2,3,4-tetrahydropyrimidin-5-yl)-2-methoxyphenyl)naphthalen-2-yl)methanesulfonamide

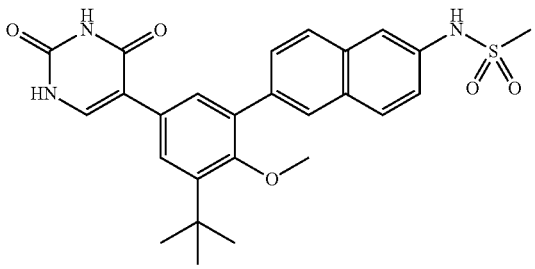 [SMILES: COc1c(-c2ccc3cc(NS(C)(=O)=O)ccc3c2)cc(-c2c[nH]c(=O)[nH]c2=O)cc1C(C)(C)C]

Part A

Preparation of 5-bromo-2,4-di-tert-butoxypyrimidine

The title compound was prepared from 5-bromo-2,4-dichloropyrimidine according to the procedure of *Organic Letters* 8(18), 4121 (2006). $^1$H NMR (300 MHz, CDCl$_3$) δ ppm 1.60 (s, 9H) 1.65 (s, 9H) 8.25 (s, 1H).

Part B

Preparation of 2,4-di-tert-butoxypyrimidin-5-ylboronic acid

The title compound was prepared from the product of Part A according to the procedure of *Chemica Scripta* 26, 305 (1986). $^1$H NMR (300 MHz, DMSO-d$_6$) δ ppm 1.56 (s, 9H) 1.59 (s, 9H) 7.60 (s, 2H) 8.35 (s, 1H).

Part C

Preparation of 2,4-di-tert-butoxy-5-(3-tert-butyl-5-iodo-4-methoxyphenyl) pyrimidine A nitrogen-purged flask was charged with 1-tert-butyl-3,5-diiodo-2-methoxybenzene (100 mg, 0.240 mmol) and anhydrous 1,2-dimethoxyethane (0.8 mL), and the solution sparged with nitrogen for 15 minutes. Tetrakis(triphenylphosphine)palladium(0) (8.33 mg, 7.2 mol) was and the mixture was sparged with nitrogen for 10 minutes. The product of Part B (70.9 mg, 0.264 mmol) and 1 M aqueous NaHCO$_3$ (0.6 mL, 0.6 mmol) were added, and the mixture was heated at reflux (oil bath temperature 100° C.) for 2 hours. The reaction mixture was cooled to room temperature, diluted with ethyl acetate (50 mL), and washed with H$_2$O (25 mL) and brine (25 mL), dried (MgSO$_4$), filtered, and concentrated in vacuo to give crude product which was purified by silica gel flash chromatography eluting with 1% ethyl acetate/dichloromethane to give the title compound. $^1$H NMR (500 MHz, CDCl$_3$) δ ppm 1.41 (s, 9H) 1.65 (s, 18H) 3.92 (s, 3H) 7.45 (s, 1H) 7.82 (s, 1H) 8.18 (s, 1H).

Part D

Preparation of N-(6-(3-tert-butyl-5-(2,4-di-tert-butoxypyrimidin-5-yl)-2-methoxy phenyl)naphthalen-2-yl)methanesulfonamide The product of Part C (84.2 mg, 0.164 mmol) and N-(6-(4,4,5,5-tetramethyl-1,3,2-dioxa borolan-2-yl)naphthalen-2-yl)methanesulfonamide (74.2 mg, 0.214 mmol) were reacted in the same manner as Example 1 Part B at 50° C. for 2 hours. The crude product was purified by silica gel flash chromatography eluting with 10% ethyl acetate/dichloromethane to give the title compound. $^1$H NMR (300 MHz, DMSO-d$_6$) δ ppm 1.45 (s, 9H) 1.59 (s, 9H) 1.62 (s, 9H) 3.08 (s, 3H) 3.23 (s, 3H) 7.39-7.45 (m, 2H) 7.51 (d, J=2.21 Hz, 1H) 7.70-7.76 (m, 2H) 7.93 (dd, J=8.82, 2.94 Hz, 2H) 8.06 (d, J=0.74 Hz, 1H) 8.40 (s, 1H) 10.01 (s, 1H).

Part E

Preparation of N-(6-(3-tert-butyl-5-(2,4-dioxo-1,2,3,4-tetrahydropyrimidin-5-yl)-2-methoxyphenyl)naphthalen-2-yl)methanesulfonamid A solution of the product of Part D (40 mg, 0.066 mmol) in methanol (0.7 mL) and 6 N HCl (0.35 mL) was stirred at 25° C. for 2 hours. During the course of the reaction, the product precipitated out of solution. The mixture was vacuum filtered and the collected solids were washed with small volumes of methanol and dried in vacuo. The crude product was dissolved in 1:1 (v/v) methanol/dimethyl sulfoxide (1 mL) and purified by RP-C$_{18}$ HPLC (Waters Prep LC, 25 mm Module with Nova Pak HR C$_{18}$ 6 m 25×100 mm Prep Pak cartridge) eluting with a 30 minute gradient of 90:10 0.1% trifluoroacetic acid in H$_2$O/acetonitrile to 25:75 0.1% trifluoroacetic acid in H$_2$O/acetonitrile at 10 mL/minute. This gave the title compound. $^1$H NMR (300 MHz, DMSO-d$_6$) δ ppm 1.42 (s, 9H) 3.08 (s, 3H) 3.20 (s, 3H) 7.38-7.50 (m, 3H) 7.67-7.71 (m, 1H) 7.71 (dd, J=5.52, 1.84 Hz, 2H) 7.92 (d, J=8.82 Hz, 1H) 7.97 (d, J=9.19 Hz, 1H) 8.01 (s, 1H) 10.01 (s, 1H) 11.12 (dd, J=4.04, 1.10 Hz, 1H) 11.22 (s, 1H).

Example 29

Preparation of N-(6-(3-tert-butyl-2-methoxy-5-(2-oxopyrrolidin-1-yl)phenyl) naphthalen-2-yl)methanesulfonamide

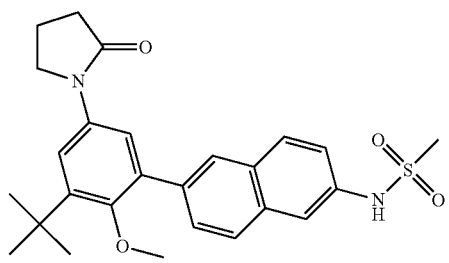 [SMILES: COc1c(-c2ccc3cc(NS(C)(=O)=O)ccc3c2)cc(N2CCCC2=O)cc1C(C)(C)C]

Part A

Preparation of 1-(3-tert-butyl-5-iodo-4-methoxyphenyl)pyrrolidin-2-one

In a 5 mL microwave tube under N$_2$ flush were added 1-tert-butyl-3,5-diiodo-2-methoxybenzene (208 mg, 0.5 mmol), 2-pyrrolidone (0.092 mL, 1.200 mmol), potassium phosphate (223 mg, 1.050 mmol), (+/−)-trans-1,2-diaminocyclohexane (0.012 mL, 0.100 mmol) and copper(I) iodide (2.381 mg, 0.013 mmol) in dioxane (2 mL). The tube was sealed, sparged with N$_2$ for 10 minutes, heated by microwave irradiation at 110° C. for 1 hour, cooled and partitioned between ethyl acetate and water adjusting the pH to 1 with HCl. The aqueous layer was extracted with ethyl acetate. The organics were combined, washed with H$_2$O, and brine. The organic was dried (Na$_2$SO$_4$), filtered, and stirred for 0.5 hours with 3-mercaptopropyl functionalized silica, filtered and concentrated. The crude product was purified on an Isco 12 g silica cartridge eluting with 4:1 hexane/ethyl acetate to give the title compound.

Part B

Preparation of N-(6-(3-tert-butyl-2-methoxy-5-(2-oxopyrrolidin-1-yl)phenyl) naphthalen-2-yl)methanesulfonamide The product from Part A (0.09 g, 0.241 mmol) and N-(6-(4,4,5,5-tetramethyl-1,3,2-dioxa borolan-2-yl)naphthalene-2-yl)methanesulfonamide (0.092 g, 0.265 mmol) were reacted in the same manner as Example 1 Part B at 50° C. for 18 hours giving crude product which was purified on an Isco 12 g silica cartridge eluting with methanol/dichloromethane (0% to 2%) to give the title compound. mp 229-230° C.; $^1$H NMR (300 MHz, DMSO-d$_6$) δ ppm 1.41 (s, 9H) 2.00-2.14 (m, 2H) 2.38-2.50 (m, 2H) 3.08 (s, 3H) 3.18 (s, 3H) 3.87 (t, J=6.99 Hz, 2H) 7.41 (dd, J=8.82, 2.21 Hz, 1H) 7.46 (d, J=2.57 Hz, 1H) 7.60-7.69 (m, 2H) 7.72 (d, J=1.84 Hz, 1H) 7.84-8.01 (m, 3H) 10.02 (s, 1H).

Example 30

Preparation of N-(6-(3-tert-butyl-2-methoxy-5-(2-oxopyridin-1(2H)-yl) phenyl)naphthalen-2-yl)methanesulfonamide

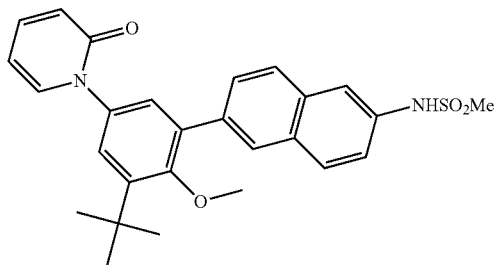

Part A

Preparation of 1-(3-tert-butyl-5-iodo-4-methoxyphenyl)pyridin-2(1H)-one

In a 20 mL microwave tube were added pyridin-2-ol (190 mg, 2 mmol), copper(I) iodide (76 mg, 0.400 mmol), 1-tert-butyl-3,5-diiodo-2-methoxybenzene (998 mg, 2.400 mmol), potassium phosphate (849 mg, 4.00 mmol) and N,N'-dimethylethylenediamine (0.086 mL, 0.800 mmol) in dioxane (10 mL). The tube was sealed and the mixture was sparged with $N_2$ for 10 minutes and heated in an oil bath at 110° C. for 16 hours. The mixture was cooled and partitioned into ethyl acetate. The organic layer was washed with saturated $NaHCO_3$, brine, dried ($Na_2SO_4$), filtered and the filtrate was treated with 3-mercaptopropyl functionalized silica gel, filtered through diatomaceous earth and concentrated in vacuo to give crude product which was purified on an Isco 12 g silica cartridge eluting with 3:2 hexane/ethyl acetate to give the title compound.

Part B

Preparation of N-(6-(3-tert-butyl-2-methoxy-5-(2-oxopyridin-1(2H)-yl)phenyl) naphthalen-2-yl)methanesulfonamide The product from Part A (153 mg, 0.40 mmol) was reacted in the same manner as Example 1 Part B at 50° C. for 18 hours giving a crude product which was purified on an Isco 12 g silica cartridge eluting with ethyl acetate/hexane (10% to 100%) to give the title compound. m.p. 258-260° C.; $^1$H NMR (300 MHz, DMSO-$d_6$) δ ppm 1.43 (s, 9H) 3.08 (s, 3H) 3.26 (s, 3H) 6.26-6.35 (m, 1H) 6.48 (d, J=8.82 Hz, 1H) 7.27 (d, J=2.57 Hz, 1H) 7.33 (d, J=2.57 Hz, 1H) 7.42 (dd, J=8.82, 1.84 Hz, 1H) 7.45-7.54 (m, 1H) 7.68-7.81 (m, 3H) 7.96 (t, J=8.27 Hz, 2H) 8.04 (s, 1H) 10.03 (s, 1H).

Example 31

Preparation of N-(6-(5-benzoyl-3-tert-butyl-2-methoxyphenyl)naphthalen-2-yl)methanesulfonamide

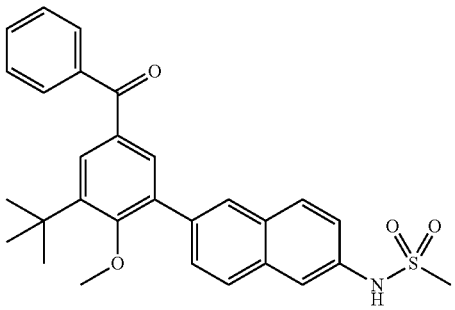 [SMILES: COc1c(-c2ccc3cc(NS(C)(=O)=O)ccc3c2)cc(C(=O)c2ccccc2)cc1C(C)(C)C]

Part A

Preparation of 1-tert-butyl-3-iodo-2-methoxy-5-(1-phenylvinyl)benzene

A solution of 1-tert-butyl-3,5-diiodo-2-methoxybenzene (4.94 g, 11.87 mmol) in dimethoxyethane (50 mL) and water (30 mL) was treated with 1-phenylvinylboronic acid (2.283 g, 15.43 mmol), tetrakis(triphenylphosphine)palladium(0) (0.686 g, 0.593 mmol) and sodium bicarbonate (2.492 g, 29.7 mmol) followed by heating at 100° C. for 3 hours. 1 N HCl was added and the mixture was extracted with ethyl acetate, then dried ($Na_2SO_4$), filtered and concentrated in vacuo to give crude product which was purified by silica gel flash chromatography eluting with 50:1 hexanes/ethyl acetate to give the title compound.

Part B

Preparation of (3-tert-butyl-5-iodo-4-methoxyphenyl)(phenyl)methanone

The product from Part A (1.10 g, 2.80 mmol) was dissolved in acetone and cooled to −78° C., then potassium permanganate (4.43 g, 28.0 mmol) was added and the resultant solution stirred at −78° C. for 2 hours. The solution was slowly warmed to room temperature and stirred for an additional 3 hours. Isopropanol (10 mL) and dichloromethane (25 mL) were added, and the mixture was stirred for 15 minutes and then filtered The filtrate was concentrated in vacuo to give the title compound.

Part C

Preparation of N-(6-(5-benzoyl-3-tert-butyl-2-methoxyphenyl)naphthalen-2-yl) methanesulfonamide The product from Part B (0.115 g, 0.292 mmol) was reacted in the same manner as Example 1 Part B at 50° C. for 24 hours to give crude product which was purified on an Isco 12 g silica cartridge eluting with hexanes in ethyl acetate to provide the title compound. $^1$H NMR (300 MHz, DMSO-$d_6$) δ ppm 1.44 (s, 9H), 3.08 (s, 3H), 3.30 (s, 3H), 7.42 (dd, J=8.8, 2.2 Hz, 1H), 7.65 (m, 2H), 7.72 (m, 2H), 7.79 (m, 3H), 7.85 (m, 1H), 7.98 (m, 2H), 10.03 (s, 1H).

Example 32

Preparation of (E)-N-(4-(5-benzoyl-3-tert-butyl-2-methoxystyryl)phenyl) methanesulfonamide

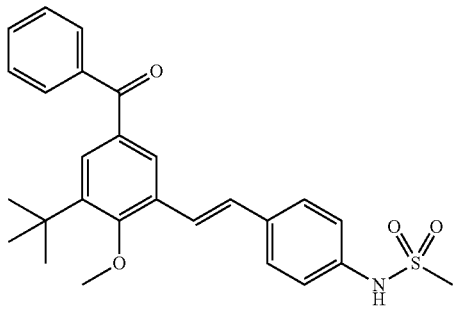 [SMILES: COc1c(/C=C/c2ccc(NS(C)(=O)=O)cc2)cc(C(=O)c2ccccc2)cc1C(C)(C)C]

(E)-4-(Methylsulfonamido)styryl boronic acid (0.673 g, 0.279 mmol) and the product from Example 31 Part B (0.100 g, 0.254 mmol) were reacted in the same manner as Example 1 Part C at 60° C. for 24 hours to give crude product which was purified on an Isco 12 g silica cartridge eluting with hexanes in ethyl acetate to provide the title compound. $^1$H NMR (300 MHz, DMSO-d$_6$) δ ppm 1.39 (s, 9H), 3.01 (s, 3H), 3.84 (s, 3H), 7.16 (d, J=16.5 Hz, 1H), 7.22 (d, J=8.5 Hz, 2H), 7.30 (d, J=16.5 Hz, 1H), 7.62 (m, 6H), 7.78 (m, 2H), 7.91 (d, J=2.2 Hz, 1H), 9.85 (s, 1H).

Example 33

Preparation of N-(6-(2-amino-3-tert-butyl-5-(2,4-dioxo-1,2,3,4-tetrahydro pyrimidin-5-yl)phenyl) naphthalen-2-yl)methanesulfonamide

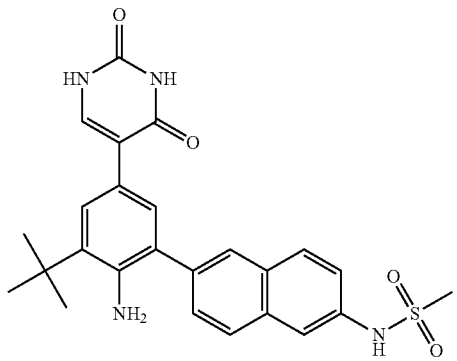 [SMILES: CC(C)(C)c1cc(-c2c[nH]c(=O)[nH]c2=O)cc(-c2ccc3cc(NS(C)(=O)=O)ccc3c2)c1N]

Part A

Preparation of 2-tert-butyl-4-iodoaniline

In a 500 mL round-bottomed flask was combined 2-tert-butylaniline (7.46 g, 50 mmol) and sodium bicarbonate (7.56 g, 90 mmol) in water (50 mL). The mixture was cooled to 0° C. and iodine (12.69 g, 50.0 mmol) was added portion-wise over 20 minutes. The mixture was stirred for 16 hours at room temperature, partitioned between ethyl acetate and 10% aqueous sodium thiosulfate and stirred vigorously for 20 minutes. The ethyl acetate layer was washed with brine, dried (Na$_2$SO$_4$), filtered and concentrated in vacuo to give a dark oil that was purified on an Isco 120 g silica cartridge eluting with ethyl acetate/hexane (0% to 10%) to give the title compound.

Part B

Preparation of 2-tert-butyl-4-(2,4-di-tert-butoxypyrimidin-5-yl)aniline

The product from Part A (138 mg, 0.5 mmol) and the product from Example 28 Part B (134 mg, 0.500 mmol) were reacted in the same manner as Example 1 Part B for 1 hour to give crude product which was purified on an Isco 12 g silica cartridge eluting with 15% ethyl acetate in hexane to give the title compound.

Part C

Preparation of 2-bromo-6-tert-butyl-4-(2,4-di-tert-butoxypyrimidin-5-yl)aniline

The product from Part B (160 mg, 0.431 mmol) and 1,3-dibromo-5,5-dimethylimidazolidine-2,4-dione (62.2 mg, 0.217 mmol) were combined in chloroform (4 mL). The reaction mixture was stirred for 1 hour, washed with sodium thiosulfate, brine, dried (Na$_2$SO$_4$), filtered and concentrated in vacuo to give crude product which was purified on an Isco 12 g silica cartridge eluting with 9:1 hexane/ethyl acetate to give the title compound.

Part D

Preparation of N-(6-(2-amino-3-tert-butyl-5-(2,4-di-tert-butoxypyrimidin-5-yl) phenyl)naphthalen-2-yl) methanesulfonamide The product from Part C (80 mg, 0.178 mmol) and N-(6-(4,4,5,5-tetramethyl-1,3,2-dioxaborolan-2-yl)naphthalen-2-yl)methanesulfonamide (61.7 mg, 0.178 mmol) were reacted in the same manner as Example 1 Part C at 50° C. for 16 hours to give crude product which was purified on an Isco 12 g silica cartridge eluting with methanol/dichloromethane (0% to 3%) to give the title compound.

Part E

Preparation of N-(6-(2-amino-3-tert-butyl-5-(2,4-dioxo-1,2,3,4-tetrahydro pyrimidin-5-yl)phenyl) naphthalen-2-yl)methanesulfonamide The product from Part D (77 mg, 0.130 mmol) was reacted in the same manner as Example 1 Part D giving a solid that was washed repeatedly with diethyl ether and dried to constant mass giving the title compound. m.p. 254-260° C.; $^1$H NMR (300 MHz, DMSO-d$_6$) δ ppm 1.43 (s, 9H) 3.07 (s, 3H) 7.18 (d, J=1.84 Hz, 1H) 7.38-7.46 (m, 2H) 7.51-7.59 (m, 2H) 7.74 (d, J=2.21 Hz, 1H) 7.86-7.98 (m, 3H)

10.03 (s, 1H) 11.00 (dd, J=5.88, 1.84 Hz, 1H) 11.13 (d, J=1.84 Hz, 1H).

Example 34

Preparation of N-(6-(3-tert-butyl-5-(2,4-dioxo-1,2,3,4-tetrahydropyrimidin-5-yl)-2-iodophenyl)naphthalen-2-yl)methanesulfonamide

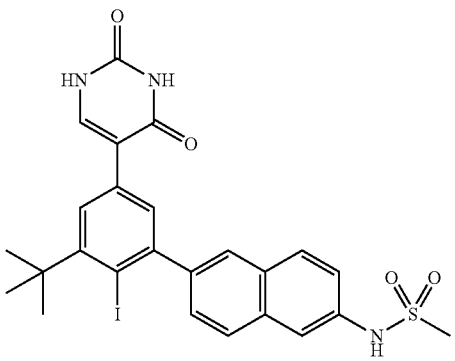 [SMILES: CC(C)(C)c1cc(-c2c[nH]c(=O)[nH]c2=O)cc(-c2ccc3cc(NS(C)(=O)=O)ccc3c2)c1I]

Part A

Preparation of N-(6-(3-tert-butyl-5-(2,4-di-tert-butoxypyrimidin-5-yl)-2-iodo phenyl)naphthalen-2-yl)methanesulfonamide To a 10 mL round-bottomed flask was added the product from Example 33 Part D (59 mg, 0.100 mmol), tert-butyl nitrite (0.012 mL, 0.100 mmol), copper(I) iodide (19.02 mg, 0.100 mmol), sodium iodide (14.97 mg, 0.100 mmol) and iodine (12.67 mg, 0.050 mmol) in 1,2-dimethoxyethane (2 mL). The mixture was heated at 60° C. for 2 hours. The reaction mixture was partitioned with ethyl acetate and 10% sodium thiosulfate. The organic layer was washed with brine, dried ($Na_2SO_4$), filtered and concentrated in vacuo to give crude product which was purified by silica gel flash chromatography eluting with ethyl acetate/hexane (5% to 20%) to give the title compound.

Part B

Preparation of N-(6-(3-tert-butyl-5-(2,4-dioxo-1,2,3,4-tetrahydropyrimidin-5-yl)-2-iodophenyl)naphthalen-2-yl)methanesulfonamide The product from Part A (30 mg, 0.043 mmol) was reacted in the same manner as Example 3 Part B to give the title compound. $^1$H NMR (300 MHz, DMSO-$d_6$) δ ppm 1.61 (s, 9H) 3.07 (s, 3H) 7.39 (m, 3H) 7.69 (m, 3H) 7.80 (s, 1H) 7.88 (d, J=8.82 Hz, 1H) 7.93 (d, J=8.82 Hz, 1H) 10.00 (s, 1H) 11.22 (s, 1H) 11.27 (s, 1H).

Example 35

N-(6-(3-tert-butyl-5-(2,4-dioxo-1,3,4-dioxo-1,2,3,4-tetrahydropyrimidin-5-yl)-2-vinyl phenyl)naphthalen-2-yl)methanesulfonamide

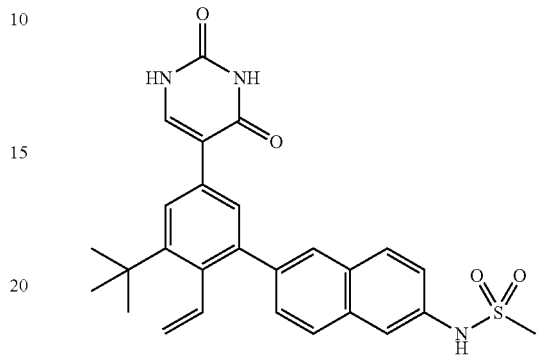

Part A

Preparation of N-(6-(3-tert-butyl-5-(2,4-di-tert-butoxypyrimidin-5-yl)-2-vinyl phenyl)naphthalen-2-yl)methanesulfonamide To a 5 mL microwave tube was added the product from Example 34 Part A (210 mg, 0.3 mmol), tributyl(vinyl)stannane (0.175 mL, 0.600 mmol), potassium phosphate (134 mg, 0.63 mmol), 1,3,5,7-tetramethyl-6-phenyl-2,4,8-trioxa-6-phosphaadamantane (8.77 mg, 0.030 mmol) and tris(dibenzylideneacetone)dipalladium(0) (13.74 mg, 0.015 mmol) in dimethyl sulfoxide (3 mL). The mixture was purged with nitrogen for 5 minutes and microwaved at 100° C. for 1 hour. The reaction mixture was partitioned with ethyl acetate and 0.1 M HCl. The organic layer was washed with saturated $NaHCO_3$, brine, dried ($Na_2SO_4$), filtered and the filtrate treated with 3-mercaptopropyl functionalized silica gel, filtered and concentrated in vacuo to give crude product which was purified by silica gel flash chromatography eluting with ethyl acetate/hexane (10% to 20%) to give the title compound.

Part B

Preparation of N-(6-(3-tert-butyl-5-(2,4-dioxo-1,2,3,4-tetrahydropyrimidin-5-yl)-2-vinylphenyl)naphthalen-2-yl)methanesulfonamide The product from Part A (30 mg, 0.050 mmol) was reacted in the same manner as Example 3 Part B to give the title compound. $^1$H NMR (300 MHz, DMSO-$d_6$) δ ppm 1.43 (s, 9H) 3.05 (s, 3H) 4.63 (dd, J=17.65, 2.21 Hz, 1H) 5.12 (dd, J=11.21, 2.02 Hz, 1H) 7.16 (dd, J=17.83, 11.21 Hz, 1H) 7.37 (m, 3H) 7.60 (d, J=1.84 Hz, 1H) 7.67 (d, J=1.84 Hz, 1H) 7.74 (m, 2H) 7.78 (d, J=8.82 Hz, 1H) 7.87 (d, J=9.19 Hz, 1H) 9.95 (s, 1H) 11.15 (s, 1H) 11.23 (s, 1H).

Example 36

N-(6-(3-tert-butyl-5-(2,4-dioxo-1,2,3,4-tetrahydropyrimidin-5-yl)-2-ethyl phenyl)naphthalen-2-yl)methanesulfonamide

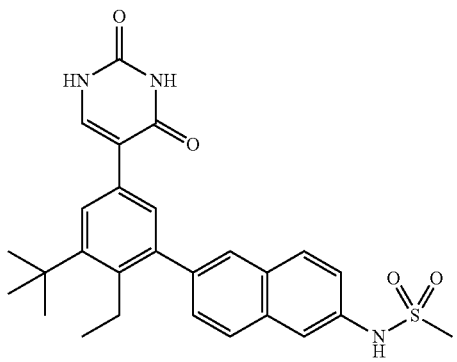 [SMILES: CCc1c(-c2ccc3cc(NS(C)(=O)=O)ccc3c2)cc(-c2c[nH]c(=O)[nH]c2=O)cc1C(C)(C)C]

Part A

Preparation of N-(6-(3-tert-butyl-5-(2,4-di-tert-butoxypyrimidin-5-yl)-2-ethyl phenyl)naphthalen-2-yl)methanesulfonamide To a 100 mL round-bottomed flask was added the product from Example 35 Part A (132 mg, 0.219 mmol), 10% palladium on carbon (20 mg, 0.019 mmol) and methanol (10 mL). The mixture was hydrogenated for 24 hours, filtered and concentrated in vacuo to give crude product which was purified by silica gel flash chromatography eluting with ethyl acetate/hexane (10% to 20%) to give the title compound.

Part B

N-(6-(3-tert-butyl-5-(2,4-dioxo-1,2,3,4-tetrahydropyrimidin-5-yl)-2-ethylphenyl) naphthalen-2-yl)methanesulfonamide The product from Part A (92 mg, 0.152 mmol) was reacted in the same manner as Example 3 Part B to give the title compound. $^1$H NMR (300 MHz, DMSO-$d_6$) δ ppm 0.69 (t, J=7.17 Hz, 3H) 1.46 (s, 9H) 2.96 (q, J=7.17 Hz, 2H) 3.07 (s, 3H) 7.19 (d, J=1.84 Hz, 1H) 7.41 (dd, J=8.82, 2.21 Hz, 1H) 7.46 (dd, J=8.46, 1.84 Hz, 1H) 7.54 (d, J=1.84 Hz, 1H) 7.65 (s, 1H) 7.73 (d, J=1.84 Hz, 1H) 7.81 (s, 1H) 7.89 (d, J=8.82 Hz, 1H) 7.93 (d, J=9.19 Hz, 1H) 9.98 (s, 1H) 11.10 (s, 1H) 11.19 (s, 1H).

Example 37

Preparation of N-(6-(5-(2,4-dioxo-1,2,3,4-tetrahydropyrimidin-5-yl)-2-methoxy-3-(perfluoroethyl)phenyl)naphthalen-2-yl)methanesulfonamide

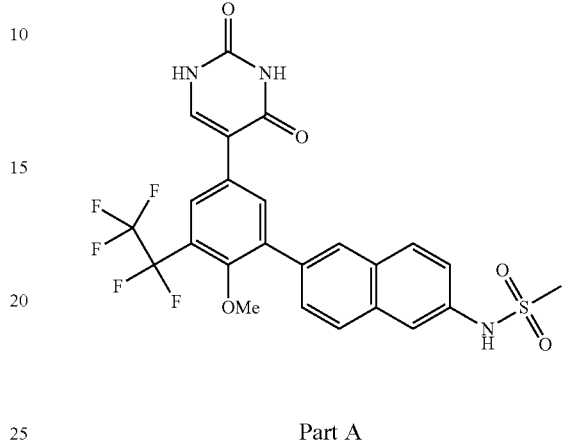

Part A

Preparation of N-(6-(2-methoxy-5-nitro-3-(perfluoroethyl)phenyl)naphthalen-2-yl)methanesulfonamide 1-Bromo-2-methoxy-5-nitro-(3-perfluoroethyl)benzene (0.25 g, 0.630 mmol) and N-(6-(4,4,5,5-tetramethyl-1,3,2-dioxaborolan-2-yl)naphthalene-2-yl)methanesulfonamide (0.219 g, 0.630 mmol) were reacted in the same manner as Example 1 Part B at 50° C. for 16 hours to give crude product which was purified on an Isco 12 g silica cartridge eluting with 3:1 hexane/ethyl acetate to give the title compound.

Part B

Preparation of N-(6-(5-amino-2-methoxy-3-(perfluoroethyl)phenyl)naphthalen-2-yl)methanesulfonamide A mixture of the product from Part A (0.27 g, 0.551 mmol), iron (0.154 g, 2.75 mmol), and ammonium chloride (0.044 g, 0.826 mmol) in a solvent mixture of tetrahydrofuran, ethanol, and water 3:3:1 (15 mL) was heated at 95-100° C. for 2 hours. The reaction mixture was filtered through a plug of diatomaceous earth and rinsed repeatedly with tetrahydrofuran. The filtrate was concentrated in vacuo and the residue was dissolved in ethyl acetate, washed with water, brine, dried (Na$_2$SO$_4$), filtered and concentrated in vacuo to give the title compound that was used without purification.

Part C

Preparation of N-(6-(5-iodo-2-methoxy-3-(perfluoroethyl)phenyl)naphthalen-2-yl)methanesulfonamide The product from Part B (0.25 g, 0.543 mmol) was reacted in the same manner as Example 34 Part A for 3 hours to give material that was purified on an Isco 40 g silica cartridge eluting with ethyl acetate/hexane (5% to 30%) to give the title compound.

Part D

Preparation of N-(6-(5-(2,4-di-tert-butoxypyrimidin-5-yl)-2-methoxy-3-(perfluoro ethyl)phenyl)naphthalen-2-yl)methanesulfonamide The product from Part C (0.13 g, 0.228 mmol) and the product from Example 28 Part B (0.064 g, 0.239 mmol) were reacted in the same manner as Example 1 Part B at 50° C. for 16 hours to give crude product which was purified on an Isco 40 g silica cartridge eluting with 15% ethyl acetate in hexane to give the title compound.

Part E

Preparation of N-(6-(5-(2,4-dioxo-1,2,3,4-tetrahydropyrimidin-5-yl)-2-methoxy-3-(perfluoroethyl)phenyl)naphthalen-2-yl)methanesulfonamide The product from Part D (0.10 g, 0.150 mmol) was reacted in the same manner as Example 1 Part D to give crude product which was purified on an Isco 4 g silica cartridge eluting with ethyl acetate to give a light yellow oil that was triturated in 95:5 dichloromethane/methanol to give the title compound. $^1$H NMR (300 MHz, DMSO-$d_6$) δ ppm 3.09 (s, 3H) 3.28 (s, 3H) 7.43 (dd, J=8.82, 1.84 Hz, 1H) 7.67-7.77 (m, 2H) 7.85-8.03 (m, 5H) 8.10 (s, 1H) 10.10 (s, 1H) 11.28 (s, 1H) 11.36 (s, 1H).

Example 38

Preparation of N-(6-(5-(2,4-dioxo-1,2,3,4-tetrahydropyrimidin-5-yl)-3-(furan-3-yl)-2-methoxyphenyl)naphthalen-2-yl)methanesulfonamide

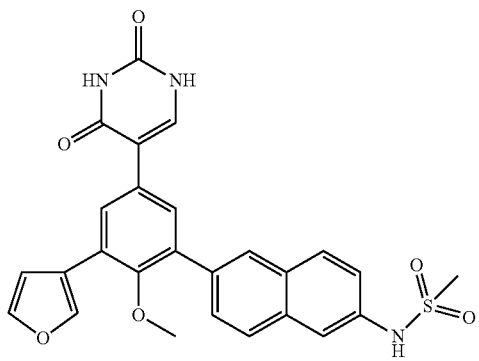 [SMILES: COc1c(-c2ccoc2)cc(-c2c[nH]c(=O)[nH]c2=O)cc1-c1ccc2cc(NS(C)(=O)=O)ccc2c1]

Part A

Preparation of 2-iodo-4-nitrophenol

2-Iodophenol (5.94 g, 27.0 mmole) was dissolved in acetonitrile (54 mL) and cooled in an ice bath. A solution of 1:1 v/v of glacial acetic acid/70% nitric acid was added dropwise and the solution was stirred 30 minutes in the ice bath. The reaction mixture was poured onto 500 g of ice water and extracted with dichloromethane. The combined organic extracts were washed with water and brine, dried (MgSO$_4$), filtered and concentrated in vacuo leaving a residue which was purified by silica gel flash chromatography eluting with ethyl acetate/hexane (5% to 50%) to give the title compound.

Part B

Preparation of 2-bromo-6-iodo-4-nitrophenol

Product from Part A (3.54 g, 13.36 mmole) was dissolved in acetonitrile (60 mL) and treated with 1,3-dibromo-5,5-dimethylhydantoin (2.1 g, 7.35 mmole) and stirred at room temperature for 15 hours. The resulting reaction mixture was concentrated in vacuo to a residue which was dissolved in dichloromethane, washed with water, 10% NaS$_2$O$_3$ solution, brine, dried (MgSO$_4$), filtered and concentrated in vacuo leaving a solid which was purified by silica gel flash chromatography eluting with ethyl acetate/hexane (5% to 50%) to give the title compound Part C Preparation of 1-bromo-3-iodo-2-methoxy-5-nitrobenzene Product from Part B (1.92 g, 5.58 mmole) was reacted in the same manner as Example 1 Part A for 20 hours giving crude product which was purified by silica gel flash chromatography eluting with ethyl acetate/hexane (0% to 50%) to give the title compound.

Part D

Preparation of N-(6-(3-bromo-2-methoxy-5-nitrophenyl)naphthalen-2-yl)methanesulfonamide Product from Part C (1.26 g, 3.52 mmole) and N-(6-(4,4,5,5-tetramethyl-1,3,2-dioxaborolan-2-yl)naphthalen-2-yl)methanesulfonamide (1.22 g, 3.52 mmole) were reacted in the same manner as Example 1 Part B for 96 hours giving crude product which was purified by silica gel flash chromatography eluting with methanol/dichloromethane (0% to 5%) giving the title compound.

Part E

Preparation of N-(6-(3-(furan-3-yl)-2-methoxy-5-nitrophenyl)naphthalen-2-yl)methanesulfonamide Product from Part D (0.1 g, 0.226 mmole), furan-3-ylboronic acid (32 mg, 0.282 mmole), 2 M sodium carbonate (0.52 mL) and tetrakis(triphenylphosphine)palladium(0) (13 mg, 0.011 mmol) were combined and dissolved in 1,2-dimethoxyethane (2.3 mL) purged with N$_2$ and heated at 80° C. for 18 hours. The reaction mixture was diluted with 50 mL of ethyl acetate, washed with 10% HCl, 10% NaHCO$_3$, brine, dried (Na$_2$SO$_4$), filtered and concentrated in vacuo giving the title compound.

Part F

Preparation of N-(6-(5-amino-3-(furan-3-yl)-2-methoxyphenyl)naphthalen-2-yl)methanesulfonamide The product from Part E (0.101 g, 0.230 mmol) was reacted in the same manner as Example 37 Part B at 80° C. for 1 hour giving crude product which was partitioned between water and dichloromethane and the aqueous phase was extracted with dichloromethane, the organics combined, dried (MgSO$_4$), filtered and concentrated in vacuo to provide the title compound which was used as isolated in the next step.

Part G

Preparation of N-(6-(3-(furan-3-yl)-5-iodo-2-methoxyphenyl)naphthalen-2-yl)methanesulfonamide The product from Part F (0.10 g, 0.247 mmol) was reacted in the same manner as Example 34 Part A for 1 hour giving crude residue which was purified by silica gel flash chromatography eluting with dichloromethane/hexane to give a mixture of 5-iodo and 5-protio compounds suitable for use as isolated in the next step.

Part H

Preparation of N-(6-(5-(2,4-di-tert-butoxypyrimidin-5-yl)-3-(furan-3-yl)-2-methoxyphenyl)naphthalen-2-yl)methanesulfonamide The product mixture from Part G (0.039 g) and product from Example 28 Part B (0.021 g, 0.077 mmol) were reacted in the same manner as Example 1 Part B for 18 hours giving crude product which was purified by silica gel flash chromatography eluting with dichloromethane/hexane to give the title compound.

Part I

Preparation of N-(6-(5-(2,4-dioxo-1,2,3,4-tetrahydropyrimidin-5-yl)-3-(furan-3-yl)-2-methoxyphenyl)naphthalen-2-yl)methanesulfonamide The product from Part H (0.027 g, 0.044 mmol) was reacted in the same manner as Example 1 Part D to give title compound. $^1$H NMR (300 MHz, DMSO-d$_6$) δ ppm 3.09 (s, 3H) 3.25 (s, 3H) 7.07 (d, J=1.47 Hz, 1H) 7.42 (dd, J=8.82, 2.21 Hz, 1H) 7.57 (d, J=2.21 Hz, 1H) 7.69-7.89 (m, 5H) 7.93 (d, J=8.82 Hz, 1H) 7.98 (d, J=8.82 Hz, 1H) 8.08 (s, 1H) 8.21 (s, 1H) 10.02 (s, 1H) 11.23 (d, J=5.88 Hz, 1H) 11.28 (s, 1H).

Example 39

Preparation of N-(6-(5-(2,4-dioxo-1,2,3,4-tetrahydropyrimidin-5-yl)-2-methoxy-3-(thiophen-2-yl)phenyl)naphthalen-2-yl)methanesulfonamide

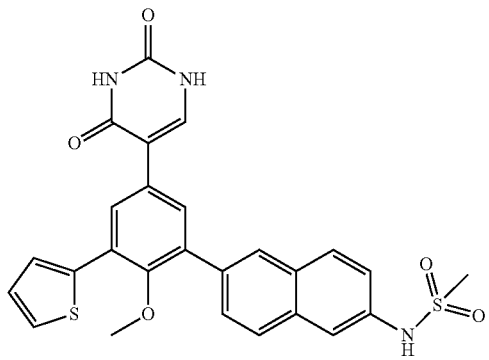 [SMILES: COc1c(-c2ccc3cc(NS(C)(=O)=O)ccc3c2)cc(-c2c[nH]c(=O)[nH]c2=O)cc1-c1cccs1]

Part A

Preparation of N-(6-(5-amino-3-bromo-2-methoxyphenyl)naphthalen-2-yl) methanesulfonamide The product from Example 38 Part D (0.10 g, 0.222 mmol) was reacted in the same manner as Example 38 Part F to give the title compound.

Part B

Preparation of N-(6-(3-bromo-5-iodo-2-methoxyphenyl)naphthalen-2-yl)methane sulfonamide The product from Part A (0.094 g, 0.222 mmol) was reacted in the same manner as Example 38 Part G to give the title compound contaminated with an undetermined amount of the corresponding des-iodo compound.

Part C

Preparation of N-(6-(3-bromo-5-(2,4-di-tert-butoxypyrimidin-5-yl)-2-methoxy phenyl)naphthalen-2-yl)methanesulfonamide The product from Part B (0.051 g, 0.048 mmol-assume 50% iodo analog) was reacted in the same manner as Example 38 Part H to give the title compound.

Part D

Preparation of N-(6-(5-(2,4-di-tert-butoxypyrimidin-5-yl)-2-methoxy-3-(thiophen-2-yl)phenyl)naphthalen-2-yl)methanesulfonamide The product from Part C (0.0281 g, 0.045 mmol) as a solution in 1,2-dimethoxyethane (1 mL) was combined at room temperature in a microwave tube with thiophen-2-ylboronic acid (8.01 mg, 0.063 mmol), sodium carbonate, (0.022 g, 0.206 mmol), 1,1'-bis(di-tertbutylphosphino)ferrocene palladium dichloride (2.37 mg, 0.0036 mmol) and water (100 µL). The tube was sealed and sparged with nitrogen for 5 minutes, then all gas lines were removed and the vessel heated in an oil bath at 55° C. for 18 hours. The contents of the tube were partitioned between ethyl acetate and brine. The aqueous phase was extracted with ethyl acetate, the organics combined, dried (MgSO$_4$) and concentrated in vacuo to give crude product which was purified by silica gel flash chromatography eluting with ethyl acetate/hexanes to give the title compound.

Part E

Preparation of N-(6-(5-(2,4-dioxo-1,2,3,4-tetrahydropyrimidin-5-yl)-2-methoxy-3-(thiophen-2-yl)phenyl)naphthalen-2-yl)methanesulfonamide The product from Part D (18.8 mg, 0.030 mmol) was reacted in the same manner as Example 1 Part D to give the title compound. $^1$H NMR (300 MHz, DMSO-d$_6$) δ ppm 3.08 (s, 3H) 3.25 (s, 3H) 7.17 (dd, J=5.15, 3.68 Hz, 1H) 7.42 (dd, J=8.82, 2.21 Hz, 1H) 7.56-7.82 (m, 4H) 7.85-8.05 (m, 4H) 8.10 (s, 1H) 9.90-10.20 (m, 1H) 11.30 (s, 1H).

Example 40

Preparation of N-(6-(5-(2,4-dioxo-1,2,3,4-tetrahydropyrimidin-5-yl)-3-(furan-2-yl)-2-methoxyphenyl)naphthalen-2-yl)methanesulfonamide

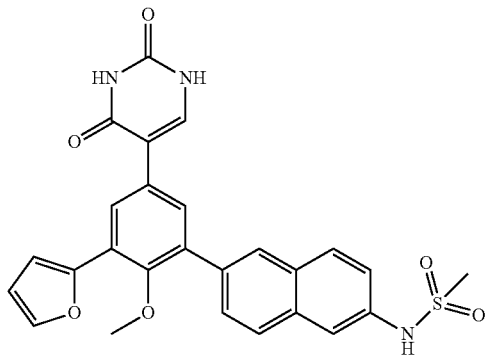 [SMILES: COc1c(-c2ccc3cc(NS(C)(=O)=O)ccc3c2)cc(-c2c[nH]c(=O)[nH]c2=O)cc1-c1ccco1]

Part A

Preparation of N-(6-(5-(2,4-di-tert-butoxypyrimidin-5-yl)-3-(furan-2-yl)-2-methoxyphenyl)naphthalen-2-yl)methanesulfonamide The product from Example 39 Part C (0.0568 g, 0.090 mmol) and furan-2-ylboronic acid (0.016 g, 0.142 mmol) were reacted in the same manner as Example 1 Part C at 55° C. for 18 hours to give crude product which was purified by silica gel flash chromatography eluting with ethyl acetate/hexanes to provide the title compound.

Part B

Preparation of N-(6-(5-(2,4-dioxo-1,2,3,4-tetrahydropyrimidin-5-yl)-3-(furan-2-yl)-2-methoxyphenyl)naphthalen-2-yl)methanesulfonamide The product from Part A (0.049 g, 0.080 mmol) was reacted in the same manner as Example 1 Part D giving the title compound. $^1$H NMR (300 MHz, DMSO-$d_6$) δ ppm 3.09 (s, 3H) 3.30 (s, 3H) 6.66 (dd, J=3.31, 1.84 Hz, 1H) 7.04 (d, J=3.31 Hz, 1H) 7.42 (dd, J=8.82, 2.21 Hz, 1H) 7.53 (d, J=2.21 Hz, 1H) 7.68-7.88 (m, 4H) 7.91-8.03 (m, 3H) 8.11 (s, 1H) 10.03 (s, 1H) 11.17-11.25 (m, 1H) 11.30 (s, 1H).

Example 41

Preparation of N-(6-(5-(2,4-dioxo-1,2,3,4-tetrahydropyrimidin-5-yl)-2-methoxy-3-(1-methyl-1H-pyrazol-4-yl)phenyl)naphthalen-2-yl)methanesulfonamide

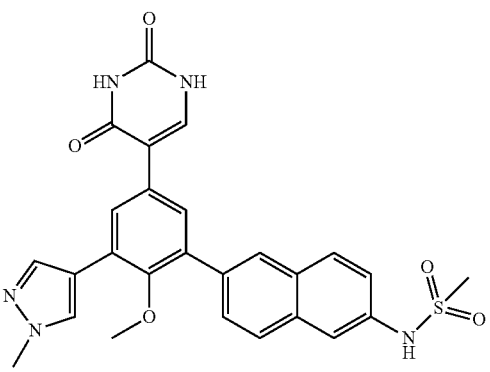 [SMILES: COc1c(-c2ccc3cc(NS(C)(=O)=O)ccc3c2)cc(-c2c[nH]c(=O)[nH]c2=O)cc1-c1cnn(C)c1]

Part A

Preparation of N-(6-(5-(2,4-di-tert-butoxypyrimidin-5-yl)-2-methoxy-3-(1-methyl-1H-pyrazol-4-yl)phenyl)naphthalen-2-yl)methanesulfonamide The product from Example 39 Part C (0.050 g, 0.080 mmol) and 1-methyl-4-(4,4,5,5-tetramethyl-1,3,2-dioxaborolan-2-yl)-1H-pyrazole (0.0276 mg, 0.133 mmol) were reacted in the same manner as Example 1 Part C to give the title compound.

Part B

Preparation of N-(6-(5-(2,4-dioxo-1,2,3,4-tetrahydropyrimidin-5-yl)-2-methoxy-3-(1-methyl-1H-pyrazol-4-yl)phenyl)naphthalen-2-yl)methanesulfonamide The product from Part A (0.045 g, 0.072 mmol) was reacted in the same manner as Example 1 Part D to give the title compound. $^1$H NMR (300 MHz, DMSO-$d_6$) δ ppm 3.08 (s, 3H) 3.23 (s, 3H) 3.91 (s, 3H) 7.42 (dd, J=8.82, 2.21 Hz, 1H) 7.50 (d, J=2.21 Hz, 1H) 7.69-7.85 (m, 4H) 7.89-8.02 (m, 3H) 8.07 (s, 1H) 8.20 (s, 1H) 9.91-10.14 (m, 1H) 11.13-11.23 (m, 1H) 11.27 (s, 1H).

115

Example 42

Preparation of N-(6-(5-(2,4-dioxo-1,2,3,4-tetrahydropyrimidin-5-yl)-2-methoxy-3-(5-methylfuran-2-yl)phenyl)naphthalen-2-yl)methanesulfonamide

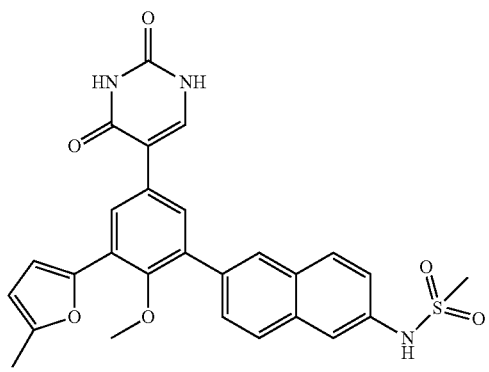 [SMILES: COc1c(-c2ccc3cc(NS(C)(=O)=O)ccc3c2)cc(-c2c[nH]c(=O)[nH]c2=O)cc1-c1ccc(C)o1]

Part A

Preparation of N-(6-(5-(2,4-di-tert-butoxypyrimidin-5-yl)-2-methoxy-3-(5-methyl furan-2-yl)phenyl)naphthalen-2-yl)methanesulfonamide The product from Example 39 Part C (0.035 g, 0.055 mmol) and 4,4,5,5-tetramethyl-2-(5-methylfuran-2-yl)-1,3,2-dioxaborolane (15.72 mg, 0.072 mmol) were reacted in the same manner as Example 1 Part C to give the title compound.

Part B

Preparation of N-(6-(5-(2,4-dioxo-1,2,3,4-tetrahydropyrimidin-5-yl)-2-methoxy-3-(5-methylfuran-2-yl)phenyl)naphthalen-2-yl)methane sulfonamide The product from Part A (10 mg, 0.016 mmol) was reacted in the same manner as Example 1 Part D to give the title compound. $^1$H NMR (300 MHz, DMSO-$d_6$) δ ppm 2.38 (s, 3H) 3.08 (s, 3H) 3.29 (s, 3H) 6.27 (d, J=2.21 Hz, 1H) 6.92 (d, J=2.94 Hz, 1H) 7.42 (dd, J=8.82, 2.21 Hz, 1H) 7.47 (d, J=2.21 Hz, 1H) 7.71-7.81 (m, 3H) 7.88-8.02 (m, 3H) 8.10 (s, 1H) 9.89-10.19 (m, 1H) 11.12-11.23 (m, 1H) 11.29 (s, 1H).

116

Example 43

Preparation of N-(6-(5-(2,4-dioxo-1,2,3,4-tetrahydropyrimidin-5-yl)-2-methoxy-3-(thiophen-3-yl)phenyl)naphthalen-2-yl)methanesulfonamide

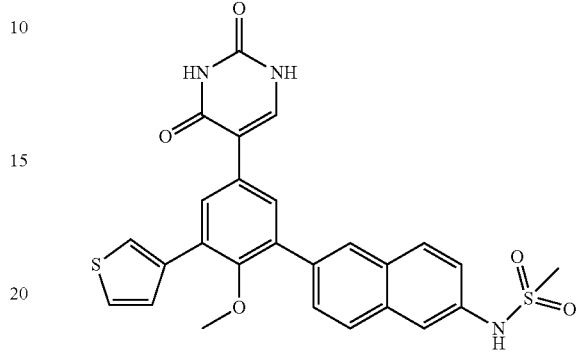

Part A

Preparation of 3-bromo-5-iodo-4-methoxyaniline

The product from Example 38 Part C (0.36 g, 1.01 mmol) was reacted in the same manner as Example 37 Part B at reflux for 90 minutes to give the title compound.

Part B

Preparation of (E)-1-((3-bromo-5-iodo-4-methoxyphenyl)diazenyl)pyrrolidine

The product from Part A (0.32 g, 1 mmol) was dissolved in tetrahydrofuran (5 mL), cooled to 0° C. in an ice bath and concentrated HCl (0.15 mL) was added. The resulting clear yellow solution was treated dropwise with NaNO$_2$ (93 mg, 1.35 mmol) in 0.3 mL water and the resulting thick solution becomes clear then opaque again over the course of 15 minutes stirring in the cold. To this mixture was added pyrrolidine (0.7 mL, 8.3 mmole) and the mixture was stirred 15 minutes in an ice bath. The mixture was treated with 100 mL of ethyl acetate, washed with water and brine, dried (Na$_2$SO$_4$), filtered and concentrated in vacuo leaving a residue which was purified on an Isco 12 g silica cartridge eluting with ethyl acetate/hexane (5% to 50%) to give the title compound.

Part C

Preparation of (E)-N-(6-(3-bromo-2-methoxy-5-(pyrrolidin-1-yldiazenyl)phenyl) naphthalen-2-yl)methanesulfonamide The product from Part B (0.107 g, 0.26 mmol) and N-(6-(4,4,5,5-tetramethyl-1,3,2-dioxaborolan-2-yl)naphthalen-2-yl)methanesulfonamide (91 mg, 0.26 mmol) were reacted in the same manner as Example 1 Part B for 17 hours to give the title compound.

Part D

Preparation of N-(6-(3-bromo-5-iodo-2-methoxyphenyl)naphthalen-2-yl)methane sulfonamide The product from Part C (0.1 g, 0.199 mmol) was dissolved in 1,2-dichloroethane (2 mL), $I_2$ (50 mg, 0.199 mmol) was added and the resulting reaction mixture was heated at 80° C. in a sealed tube for 4 hours. The reaction mixture was diluted with 50 mL of dichloromethane, washed with 30% aqueous $Na_2S_2O_3$ and brine, dried ($Na_2SO_4$), filtered and concentrated in vacuo leaving a residue which was purified on an Isco 12 g silica cartridge eluting with ethyl acetate/hexane (5% to 80%) to give the title compound.

Part E

Preparation of N-(6-(3-bromo-5-(2,4-di-tert-butoxypyrimidin-5-yl)-2-methoxy phenyl)naphthalen-2-yl)methanesulfonamide The product from Part D (23 mg, 0.043 mmole) and 2,4-di-tert-butoxypyrimidin-5-yl boronic acid (14 mg, 0.052 mmol) were reacted in the same manner as Example 1 Part B for 18 hours to give the title compound.

Part F

Preparation of N-(6-(5-(2,4-di-tert-butoxypyrimidin-5-yl)-2-methoxy-3-(thiophen-3-yl)phenyl)naphthalen-2-yl)methanesulfonamide The product from Part E (25 mg, 0.04 mmole) and thiophen-3-ylboronic acid (6.1 mg, 0.048 mmole) were reacted in the same manner as Example 1 Part C at 40° C. for 1 hour, then heated at 50° C. for 1 hour to give a residue which was purified on an Isco 4 g silica cartridge eluting with methanol/dichloromethane (1% to 3%) to give the title compound.

Part G

Preparation of N-(6-(5-(2,4-dioxo-1,2,3,4-tetrahydropyrimidin-5-yl)-2-methoxy-3-(thiophen-3-yl)phenyl)naphthalen-2-yl)methanesulfonamide The product from Part F (12 mg, 0.019 mmol) was reacted in the same manner as Example 3 Part B to give the title compound. $^1$H NMR (300 MHz, DMSO-$d_6$) δ ppm 3.07 (s, 3H) 3.20 (s, 3H) 7.41 (dd, J=8.82, 2.21 Hz, 2H) 7.51-7.70 (m, 4H) 7.72-7.81 (m, 2H) 7.83-8.03 (m, 4H) 8.07 (s, 1H) 10.02 (s, 1H) 11.28 (s, 1H).

Example 44

Preparation of N-((6-(5-(2,4-dioxo-1,2,3,4-tetrahydropyrimidin-5-yl)-2-methoxy-3-(5-methylfuran-2-yl)phenyl)-1H-inden-3-yl)methyl)methanesulfonamide

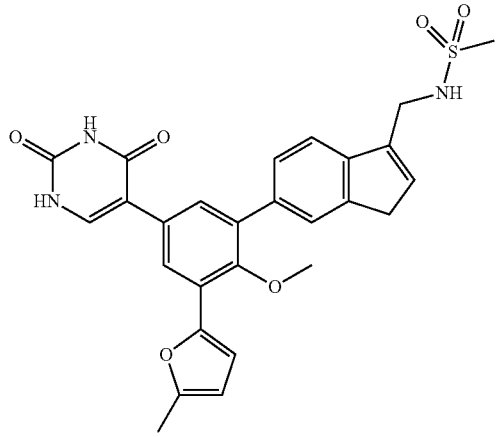 [SMILES: COc1c(-c2ccc3c(c2)CC=C3CNS(C)(=O)=O)cc(-c2c[nH]c(=O)[nH]c2=O)cc1-c1ccc(C)o1]

Part A

Preparation of (E)-1-((3-bromo-4-methoxy-5-(5-methylfuran-2-yl)phenyl) diazenyl)pyrrolidine 1-((3-Bromo-5-iodo-4-methoxyphenyl)diazenyl)pyrrolidine (0.15 g, 0.366 mmol) and 4,4,5,5-tetramethyl-2-(5-methylfuran-2-yl)-1,3,2-dioxaborolane (0.076 g, 0.366 mmol), were reacted in the same manner as Example 1 Part B for 18 hours to give crude product which was purified on an Isco 12 g silica cartridge eluting with ethyl acetate/hexane (0% to 25%) to give the title compound.

Part B

Preparation of 2-(3-bromo-5-iodo-2-methoxyphenyl)-5-methylfuran

The product from Part A (0.10 g, 0.275 mmol) was reacted in the same manner as Example 43 Part D using acetonitrile as solvent and heating at 100° C. for 2 hours to give crude product which was purified on an Isco 12 g silica cartridge eluting with ethyl acetate/hexane (0% to 10%) to give the title compound.

Part C

Preparation of 5-(3-bromo-4-methoxy-5-(5-methylfuran-2-yl)phenyl)-2,4-di-tert-butoxypyrimidine The product from Part B (0.045 g, 0.114 mmol) and the product from Example 28 Part B (0.032 g, 0.12 mmol) were reacted in the same manner as Example 1 Part B for 18 hours to give crude product which was purified on an Isco 4 g silica cartridge eluting with ethyl acetate/hexane (10% to 20%) to give the title compound.

Part D

Preparation of N-((6-(5-(2,4-di-tert-butoxypyrimidin-5-yl)-2-methoxy-3-(5-methyl furan-2-yl)phenyl)-1H-inden-3-yl)methyl)methanesulfonamide The product from Part C (0.035 g, 0.072 mmol) and N-((6-(4,4,5,5-tetramethyl-1,3,2-dioxa borolan-2-yl)-1H-inden-3-yl)methyl)methanesulfonamide (0.028 g, 0.079 mmol) were reacted in the same manner as Example 1 Part C for 2.5 hours to give crude product which was purified on an Isco 4 g silica cartridge eluting with ethyl acetate/hexane (0% to 20%) to give the title compound.

Part E

Preparation of N-((6-(5-(2,4-dioxo-1,2,3,4-tetrahydropyrimidin-5-yl)-2-methoxy-3-(5-methylfuran-2-yl)phenyl)-1H-inden-3-yl)methyl)methanesulfonamide The product from Part D (0.015 g, 0.024 mmol) was reacted in the same manner as Example 3 Part B to give the title compound. $^1$H NMR (300 MHz, DMSO-$d_6$) δ ppm 2.38 (s, 3H) 2.96 (s, 3H) 3.29 (s, 3H) 3.47 (s, 2H) 4.19 (d, J=4.78 Hz, 2H) 6.26 (d, J=2.94 Hz, 1H) 6.56 (s, 1H) 6.90 (d, J=3.31 Hz, 1H) 7.38 (d, J=2.21 Hz, 1H) 7.50 (t, J=6.07 Hz, 1H) 7.58 (d, J=1.10 Hz, 2H) 7.74 (d, J=9.56 Hz, 2H) 7.86 (d, J=2.21 Hz, 1H) 11.16 (s, 1H) 11.27 (s, 1H).

Example 45

Preparation of (E)-N'-((3'-tert-butyl-5'-(2-(1,1-dioxidoisothiazolidin-2-yl))-2'methoxybiphenyl-4-yl)methylene)methanesulfonylhydrazide

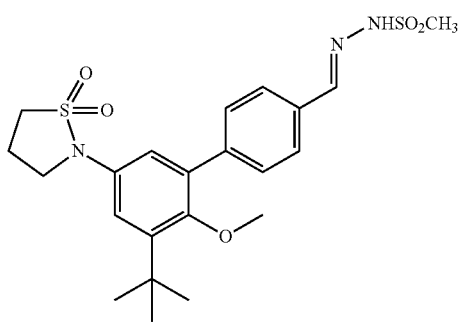

Part A

Preparation of tert-butyl 3-bromo-5-tert-butyl 4-methoxyphenylcarbamate

To a flask containing N-(3-bromo-5-tert-butyl-4-methoxyphenyl)acetamide (2.2 g, 7.33 mmol) was added 6 N HCl (24.4 mL, 147 mmol) and the solution was heated at reflux for 2 hours. The cooled solution was basified carefully with saturated NaHCO$_3$ solution, extracted with ethyl acetate, the organic extracts combined, washed with brine, dried (Na$_2$SO$_4$), filtered and concentrated in vacuo to give a residue which was dissolved in tetrahydrofuran (36.6 mL) and di-tert-butyl dicarbonate (1.87 mL, 8.1 mmol) was added and refluxed for 3 hours, cooled and solvent removed in vacuo to give crude product which was purified by silica gel flash chromatography eluting with 30% ethyl acetate/hexane to give the title compound.

Part B

Preparation of 2-(3-bromo-5-tert-butyl-4-methoxyphenyl)isothiazolidine 1,1-dioxide To a solution of product from Part A (442 mg, 1.2 mmol) in dichloromethane (5 mL) was added trifluoroacetic acid (5 mL) and stirring was continued at room temperature for 1 hour, solvent was removed in vacuo and the crude product was dissolved in 1:1 ethyl acetate/saturated NaHCO$_3$. The phases were separated and the aqueous phase was extracted with ethyl acetate, the organic extracts were washed with brine, dried (Na$_2$SO$_4$), filtered and concentrated in vacuo. Benzene (2.5 mL) was added followed by pyridine (0.37 mL, 4.6 mmol) and 3-chloropropane-1-sulfonyl chloride (0.15 mL, 1.2 mmol) and stirring was continued at room temperature for 6 hours. Solvent was removed in vacuo and the crude residue was placed under vacuum for 1 hour, 2 M NaOH (3.0 mL, 6 mmol) was added and the solution was heated at 45° C. for 18 hours. The cooled solution was diluted with H$_2$O, extracted with ethyl acetate, the organic extracts were washed with brine, dried (Na$_2$SO$_4$), filtered and concentrated in vacuo to give crude product which was purified by silica gel flash chromatography eluting with 25% ethyl acetate/hexane to give the title compound.

Part C

Preparation of 3'-tert-butyl-5'-(2-(1,1-dioxidoisothiazolidin-2-yl))-2'-methoxy biphenyl-4-carbaldehyde To a microwave tube containing ethanol (1 mL) and toluene (1 mL) was added product from Part B (65 mg, 0.18 mmol), 4-formylphenylboronic acid (35 mg, 0.23 mmol), and 1 M Na$_2$CO$_3$ (0.18 mL, 0.18 mmol) and the solution was de-gassed with N$_2$ for 15 minutes. 1,1'-Bis(diphenyl phosphino)ferrocene-palladium(II)dichloride dichloromethane complex (7.3 mg, 9 mmol) was added and the solution was de-gassed another 5 minutes, the tube sealed and heated in the microwave at 100° C. for 30 minutes, cooled and diluted with 1:1 ethyl acetate/H$_2$O and filtered through diatomaceous earth. The phases were separated and the aqueous phase was extracted with ethyl acetate, the organic extracts were washed with brine, dried (Na$_2$SO$_4$), filtered and concentrated in vacuo to give the title compound.

Part D

Preparation of (E)-N'-((3'-tert-butyl-5'-(2-(1,1-dioxidoisothiazolidin-2-yl))-2'methoxybiphenyl-4-yl)methylene)methanesulfonylhydrazide To a solution of the product from Part C (45 mg, 0.12 mmol) in methanol (0.5 mL) was added methanesulfonohydrazide (13 mg, 0.12 mmol) with rapid stirring. After stirring at 35° C. for 1 hour, the solvent was removed in vacuo, and the crude product was suspended in diethyl ether, filtered, and the resulting solid collected by filtration to give the title compound. $^1$H NMR (300 MHz, DMSO-$d_6$) δ ppm 1.39 (s, 9H) 2.31-2.45 (m, 2H), 3.09 (s, 3H), 3.21 (s, 3H), 3.48 (t, J=7.54 Hz, 2H), 3.76 (t, J=6.43 Hz, 2H), 7.02 (d, J=2.57 Hz, 1H), 7.18 (d, J=2.94 Hz, 1H), 7.58 (d, J=8.46 Hz, 2H), 7.77 (d, J=8.46 Hz, 2H), 8.05 (s, 1H), 11.11 (s, 1H).

Example 46

Preparation of N-(6-(3-tert-butyl-5-(2-(1,1-dioxido-isothiazolidin-2-yl))-2-methoxyphenyl)naphthalene-2-yl)methanesulfonamide

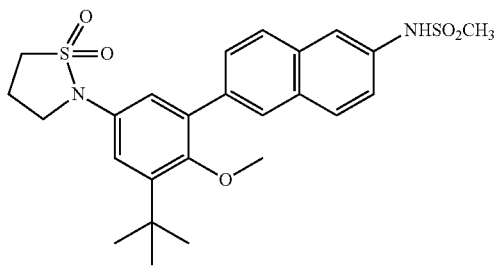

N-(6-(3-tert-butyl-5-(2-(1,1-dioxidoisothiazolidin-2-yl))-2-methoxyphenyl)naphthalene-2-yl)methanesulfonamide The product from Example 45 Part B (52 mg, 0.14 mmol) and N-(6-(4,4,5,5-tetramethyl-1,3,2-dioxaborolan-2-yl)naphthalene-2-yl)methanesulfonamide (64.8 mg, 0.19 mmol) were reacted in the same manner as Example 43 Part C to give crude product which was purified by silica gel flash chromatography eluting with ethyl acetate/hexane (20% to 30%) to give the title compound. $^1$H NMR (300 MHz, DMSO-$d_6$) δ ppm 1.41 (s, 9H), 2.30-2.45 (m, 2H), 3.08 (s, 3H), 3.18 (s, 3H), 3.49 (t, J=7.54 Hz, 2H), 3.77 (t, J=6.62 Hz, 2H), 7.15 (dd, J=29.78, 2.57 Hz, 2H), 7.42 (dd, J=8.64, 2.02 Hz, 1H), 7.61-7.76 (m, 2H), 7.86-8.04 (m, 3H), 10.03 (s, 1H).

Example 47

Preparation of N-(3-tert-butyl-4-methoxy-5-(6-(methylsulfonamido) naphthalen-2-yl)phenyl)acetamide

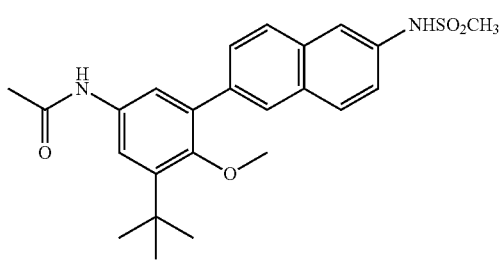

N-(3-tert-butyl-4-methoxy-5-(6-(methylsulfona-mido)naphthalen-2-yl)phenyl)acetamide N-(3-bromo-5-tert-butyl-4-methoxyphenyl)acetamide (24 mg, 0.08 mmol) and N-(6-(4,4,5,5-tetramethyl-1,3,2-dioxaborolan-2-yl)naphthalene-2-yl)methanesulfonamide (64 mg, 0.18 mmol), were reacted in the same manner as Example 43 Part C, heating in an oil bath at 90° C. for 18 hours to give crude product which was purified on an Isco 4 g silica cartridge eluting with 5% methanol/chloroform to give the title compound. $^1$H NMR (300 MHz, DMSO-$d_6$) δ ppm 1.39 (s, 9H), 2.02 (s, 3H), 3.06 (s, 3H), 3.16 (s, 3H), 7.34-7.76 (m, 5H), 7.84-8.00 (m, 3H), 9.91 (s, 1H).

Example 48

Preparation of 5-(3-bromo-4-methoxy-5-(trifluoromethyl)phenyl)pyrimidine-2,4(1H,3H)-dione

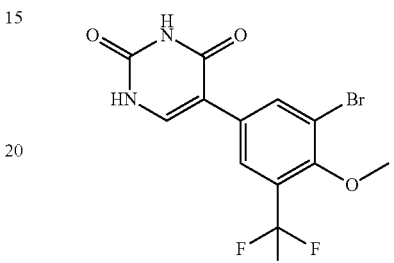

Part A

Preparation of 4-iodo-2-(trifluoromethyl)phenol

A solution of 2-trifluoromethylphenol (10 g, 61.7 mmol) in methanol (125 mL) at room temperature was treated with sodium hydroxide (13.87 g, 93 mmol) and stirred until homogeneous. The mixture was cooled in an ice bath and sodium iodide (2.96 g, 74 mmol) was added portionwise followed by the addition of 10% sodium hypochlorite (84 mL, 136 mmol) dropwise, dividing these reagents into 3 portions and adding them sequentially over 30 minutes. The solution was then adjusted to pH 1 by dropwise addition of concentrated hydrochloric acid and poured into brine. The product was extracted into ethyl acetate, concentrated in vacuo and purified by silica gel flash chromatography eluting with ethyl acetate/hexane (0% to 5%) to give the title compound.

Part B

Preparation of 2-bromo-4-iodo-6-(trifluoromethyl)phenol

A solution of the product from Part A (15.9 g, 55.2 mmol) in chloroform (230 mL) at room temperature was treated with bromohydantoin (8.68 g, 30.4 mmol) and stirred for 1.5 hours. The reaction solution was washed with water, concentrated in vacuo and purified by silica gel flash chromatography eluting with dichloromethane/hexane (50% to 100%) to give the title compound.

Part C

Preparation of 1-bromo-5-iodo-2-methoxy-3-(trifluoromethyl)benzene

The product from Part B (12.12 g, 33.0 mmol) was reacted in the same manner as Example 1 Part A at 60° C. for 7 hours to give crude product which was purified by silica gel flash chromatography eluting with ethyl acetate/hexane (0% to 2%) to give the title compound.

Part D

Preparation of 5-(3-bromo-4-methoxy-5-(trifluoromethyl)phenyl)-2,4-di-tert-butoxypyrimidine The product from Part C (0.40 g, 1.05 mmol) and the product from Example 28 Part B (0.338 g, 1.26 mmol) were reacted in the same manner as Example 1 Part B to give crude product which was purified by silica gel flash chromatography eluting with ethyl acetate/hexane (2% to 5%) to give the title compound.

Part E

Preparation of 5-(3-bromo-4-methoxy-5-(trifluoromethyl)phenyl)pyrimidine-2,4(1H,3H)-dione A solution of the product from Part D (0.027 g, 0.058 mmol) in dichloromethane (1 mL) at room temperature was treated with 4 M HCl in dioxane (1 mL) for 2 hours. The precipitate was filtered and dried to give the title compound. $^1$H NMR (300 MHz, DMSO-$d_6$) δ ppm 3.88 (s, 3H) 7.91 (s, 1H) 7.93 (d, J=2.21 Hz, 1H) 8.17 (d, J=2.21 Hz, 1H) 11.37 (s, 2H).

Example 49

Preparation of N-(6-(5-(2,4-dioxo-1,2,3,4-tetrahydropyrimidin-5-yl)-2-methoxy-3-(trifluoromethyl)phenyl)naphthalen-2-yl)methanesulfonamide

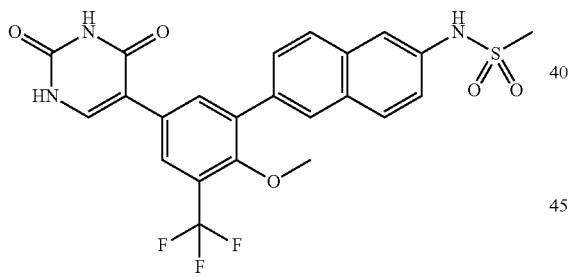

Part A

Preparation of N-(6-(5-(2,4-di-tert-butoxypyrimidin-5-yl)-2-methoxy-3-(trifluoromethyl)phenyl)naphthalen-2-yl)methanesulfonamide A solution of the product from Example 48 Part D (0.075 g, 0.16 mmol) in toluene (1 mL) and ethanol (1 mL) in a tube was treated with N-(6-(4,4,5,5-tetramethyl-1,3,2-dioxaborolan-2-yl)naphthalene-2-yl)methanesulfonamide (0.060 g, 0.17 mmol), 1 M sodium carbonate solution (0.24 mL, 0.24 mmol), and tetrakis(triphenylphosphine)palladium(0) (0.0055 g, 0.0047 mmol), then nitrogen was bubbled through the solution for 15 minutes before the tube was sealed and heated to 90° C. for 2 hours. The solution was cooled, poured into 0.25 M HCl solution, extracted into ethyl acetate, concentrated in vacuo and purified by silica gel flash chromatography eluting with methanol/dichloromethane (0% to 2%) to give the title compound.

Part B

Preparation of N-(6-(5-(2,4-dioxo-1,2,3,4-tetrahydropyrimidin-5-yl)-2-methoxy-3-(trifluoromethyl)phenyl)naphthalen-2-yl)methanesulfonamide A solution of the product from Part A (0.62 g, 0.10 mmol) was reacted in the same manner as Example 2 Part C for 1 hour to give the title compound. $^1$H NMR (300 MHz, DMSO-$d_6$) δ ppm 3.09 (s, 3H) 3.32 (s, 3H) 7.43 (dd, J=8.82, 2.21 Hz, 1H) 7.74-7.78 (m, 2H) 7.91-8.02 (m, 5H) 8.13 (s, 1H) 10.07 (s, 1H) 11.31 (dd, J=6.25, 1.10 Hz, 1H) 11.36 (d, J=1.47 Hz, 1H).

Example 50

Preparation of (E)-N-(4-(5-(2,4-dioxo-1,2,3,4-tetrahydropyrimidin-5-yl)-2-methoxy-3-(trifluoromethyl)styryl)phenyl)methanesulfonamide

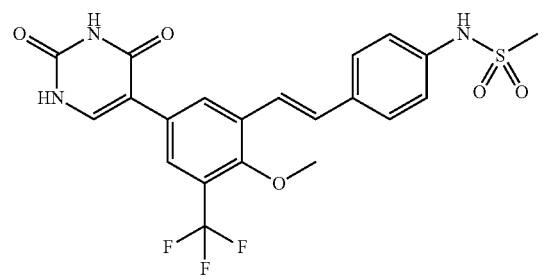 [SMILES: COc1c(/C=C/c2ccc(NS(C)(=O)=O)cc2)cc(-c2c[nH]c(=O)[nH]c2=O)cc1C(F)(F)F]

Part A

Preparation of (E)-N-(4-(5-(2,4-di-tert-butoxypyrimidin-5-yl)-2-methoxy-3-(trifluoromethyl)styryl)phenyl)methanesulfonamide A solution of the product from Example 48 Part D (0.075 g, 0.16 mmol) and (E)-4-(methylsulfonamido)styryl boronic acid (0.042 g, 0.17 mmol) were reacted in the same manner as Example 49 Part A to give crude product which was purified by silica gel flash chromatography eluting with methanol/dichloromethane (0% to 2%) to give the title compound.

Part B

Preparation of (E)-N-(4-(5-(2,4-dioxo-1,2,3,4-tetrahydropyrimidin-5-yl)-2-methoxy-3-(trifluoromethyl)styryl)phenyl)methanesulfonamide A solution of the product from Part A (0.64 g, 0.11 mmol) was reacted in the same manner as Example 2 Part C for 1 hour to give the title compound. $^1$H NMR (300 MHz, DMSO-$d_6$) δ ppm 3.03 (s, 3H) 3.81 (s, 3H) 7.21-7.43 (m, 4H) 7.65 (d, J=8.46 Hz, 2H) 7.81 (d, J=2.21 Hz, 1H) 7.89 (d, J=5.88 Hz, 1H) 8.13 (d, J=1.84 Hz, 1H) 9.90 (s, 1H) 11.33 (d, J=5.88 Hz, 1H) 11.36 (d, J=1.10 Hz, 1H).

Example 51

Preparation of N-((6-(5-(2,4-dioxo-1,2,3,4-tetrahydropyrimidin-5-yl)-2-methoxy-3-(trifluoromethyl)phenyl)benzo[b]thiophen-3-yl)methyl)methanesulfonamide

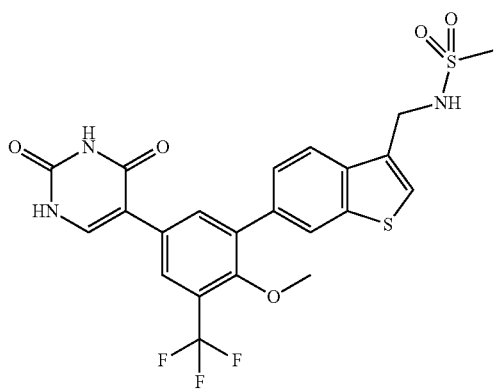 [SMILES: COc1c(-c2ccc3c(CNS(C)(=O)=O)csc3c2)cc(-c2c[nH]c(=O)[nH]c2=O)cc1C(F)(F)F]

Part A

Preparation of N-((6-(5-(2,4-di-tert-butoxypyrimidin-5-yl)-2-methoxy-3-(trifluoromethyl)phenyl)benzo[b]thiophen-3-yl)methyl)-N-(2,4-dimethoxybenzyl)methanesulfonamide A solution of the product from Example 48 Part D (0.095 g, 0.199 mmol) and N-(2,4-dimethoxybenzyl)-N-((6-(4,4,5,5-tetramethyl-1,3,2-dioxaborolan-2-yl)benzo[b]thiophen-3-yl)methyl)methanesulfonamide (0.113 g, 0.22 mmol) were reacted in the same manner as Example 49 Part A at 85° C. to give crude product which was purified by silica gel flash chromatography eluting with ethyl acetate/hexane (0% to 20%) to give the title compound.

Part B

Preparation of N-((6-(5-(2,4-dioxo-1,2,3,4-tetrahydropyrimidin-5-yl)-2-methoxy-3-(trifluoromethyl)phenyl)benzo[b]thiophen-3-yl)methyl)methane sulfonamide A solution of the product from Part A (0.97 g, 0.12 mmol) was reacted in the same manner as Example 2 Part C for 1 hour to give the title compound. ¹H NMR (300 MHz, DMSO-d₆) δ ppm 2.95 (s, 3H) 3.32 (s, 3H) 4.45 (d, J=5.88 Hz, 2H) 7.64 (t, J=6.07 Hz, 1H) 7.70 (dd, J=8.46, 1.47 Hz, 1H) 7.73 (s, 1H) 7.89 (d, J=2.21 Hz, 1H) 7.93 (dd, J=4.04, 1.84 Hz, 2H) 8.05 (d, J=8.46 Hz, 1H) 8.26 (d, J=1.47 Hz, 1H) 11.32 (d, J=5.88 Hz, 1H) 11.36 (s, 1H).

Example 52

Preparation of N-((6-(2-methoxy-5-(1-(methylsulfonyl)-2,4-dioxo-1,2,3,4-tetrahydropyrimidin-5-yl)-3-(trifluoromethyl)phenyl)-1H-inden-3-yl)methyl)methanesulfonamide

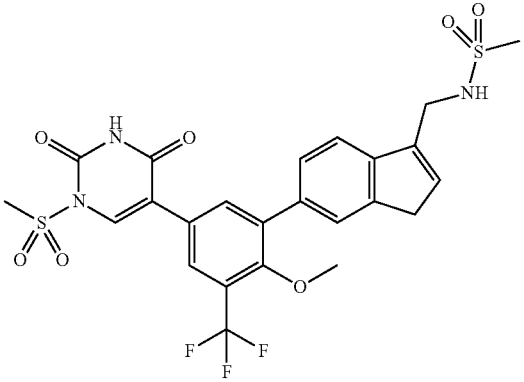

Part A

Preparation of N-((6-(5-(2,4-di-tert-butoxypyrimidin-5-yl)-2-methoxy-3-(trifluoromethyl)phenyl)-1H-inden-3-yl)methyl)methanesulfonamide A solution of the product from Example 48 Part D (0.080 g, 0.17 mmol) and N-((6-(4,4,5,5-tetramethyl-1,3,2-dioxaborolan-2-yl)-1H-inden-3-yl)methyl)methanesulfonamide (0.0685 g, 0182 mmol) was reacted in the same manner as Example 49 Part A at 60° C. for 3 hours to give crude product which was purified by silica gel flash chromatography eluting with ethyl acetate/hexane (0% to 20%) to give the title compound.

Part B

Preparation of 5-(3-(3-(aminomethyl)-1H-inden-6-yl)-4-methoxy-5-(trifluoromethyl)phenyl)pyrimidine-2,4(1H,3H)-dione hydrochloride The product from Part A (0.052 g, 0.08 mmol) in dioxane (4 mL) was treated with 4 M HCl in dioxane (3 mL) at room temperature for 4 hours and concentrated in vacuo to give the title compound which is used immediately in the next step.

Part C

Preparation of N-((6-(2-methoxy-5-(1-(methylsulfonyl)-2,4-dioxo-1,2,3,4-tetrahydropyrimidin-5-yl)-3-(trifluoromethyl)phenyl)-1H-inden-3-yl)methyl)methanesulfonamide To a solution of the product of Part B (0.037 g, 0.079 mmol) in dichloromethane (3 mL) cooled in an ice bath was added diisopropylethylamine (0.055 mL, 0.32 mmol) followed by methanesulfonyl chloride (0.0068 mL, 0.087 mmol). The ice bath was removed and the solution was stirred at room temperature for 2 hours with no reaction seen. Another 0.005 μL of methanesulfonyl chloride was added and the solution was stirred another 1 hour. The solution was poured into 1 M HCl, extracted into ethyl acetate, concentrated in vacuo and the crude product was purified by silica gel flash chromatography eluting with methanol/dichloromethane (0% to 5%) to give the title compound. $^1$H NMR (300 MHz, DMSO-d$_6$) δ 2.96 (s, 3H) 3.35 (s, 3H) 3.49 (d, J=1.10 Hz, 2H) 3.74 (s, 3H) 4.19 (d, J=4.78 Hz, 2H) 6.59 (s, 1H) 7.50 (t, J=6.07 Hz, 1H) 7.54-7.59 (m, 1H) 7.61-7.67 (m, 1H) 7.72 (s, 1H) 7.79 (s, 2H) 8.01 (s, 1H) 12.17 (s, 1H).

HCV Polymerase Inhibition Assay

Either two-fold serial dilutions (fractional inhibition assay) or a narrower range of dilutions spanning the IC$_{50}$ of the inhibitor (tight binding assay) of the inhibitors were incubated with 20 mM Tris-Cl pH 7.4, 2 mM MnCl$_2$, 1 mM dithiothreitol, 1 mM ethylene diamine tetraacetic acid (EDTA), 60 to 125 μM GTP and 20 to 50 nM Δ21 NS5B (HCV Strain 1B (BK, Genbank accession number M58335, or H77, Genbank accession number AF011751)) for 15 minutes at room temperature. The reaction was initiated by the addition of 20 μM CTP, 20 μM ATP, 1 μM $^3$H-UTP (10 mCi/umol), 5 nM template RNA and 0.1 U/μl RNase inhibitor (RNasin, Promega), and allowed to proceed for 2 to 4 hours at room temperature. Reaction volume was 50 μL. The reaction was terminated by the addition of 1 volume of 4 mM spermine in 10 mM Tris-Cl pH 8.0, 1 mM EDTA. After incubation for at least 15 minutes at room temperature, the precipitated RNA was captured by filtering through a GF/B filter (Millipore) in a 96 well format. The filter plate was washed three times with 200 μL each of 2 mM spermine, 10 mM Tris-Cl pH 8.0, 1 mM EDTA, and 2 times with ethanol. After air-drying, 30 μL of Microscint 20 scintillation cocktail (Packard) was added to each well, and the retained cpm were determined by scintillation counting. IC$_{50}$ values were calculated by a two-variable nonlinear regression equation using an uninhibited control and a fully inhibited control sample to determine the minimum and maximum for the curve. Tight-binding assays were performed on those compounds exhibiting IC$_{50}$ values less than 0.005 μM in the fractional inhibition assay in order to more precisely measure the IC$_{50}$ values. Retained cpm were plotted vs. inhibitor concentration and fit to equation 1 using non-linear regression (ref. 1) to obtain the IC$_{50}$ values:

$$\text{Retained cpm} = A[\text{sqrt}\{(IC_{50}+I_t-E_t)^2+4*IC_{50}*E_t\}-(IC_{50}+I_t-E_t)] \quad \text{(eqn 1)}$$

where A=Vmax[S]/2(Km+[S]); It=total inhibitor concentration and Et=total active concentration of enzyme.

Ref. Morrison, J. F. and S. R. Stone. 1985. Approaches to the study and analysis of the inhibition of enzymes by slow- and tight-binding inhibitors. Comments Mol. Cell. Biophys. 2: 347-368.

The sequence of the template RNA used was: 5'-GGGC-GAAUUG GGCCCUCUAG AUGCAUGCUC GAGCG-GCCGC CAGUGUGAUG GAUAUCUGCA GAAUUCGCCC UUGGUGGCUC CAUCUUAGCC CUAGUCACGG CUAGCUGUGA AAGGUCCGUG AGCCGCUUGA CUGCAGAGAG UGCUGAUACU GGCCUCUCUG CAGAUCAAGUC-3' (SEQ ID NO: 1)

When tested by the above method, the compounds of this invention inhibit HCV polymerase 1A and/or 1B. The legend in the table below is as follows: A—IC$_{50}$≤0.01 uM; B—0.1 uM≥IC$_{50}$>0.01 uM; C—1 uM≥IC$_{50}$>0.1 uM; and D—IC$_{50}$>1 uM; ND—not determined.

TABLE IC$_{50}$

| compound | 1a | 1b | compound | 1a | 1b |
|---|---|---|---|---|---|
| 1 | C | C | 2 | A | A |
| 3 | A | A | 4 | A | B |
| 5 | D | D | 6 | A | B |
| 7 | A | B | 8 | C | C |
| 9 | A | B | 10 | C | D |
| 11 | D | D | 12 | B | B |
| 13 | C | C | 14 | A | B |
| 15 | A | B | 16 | B | B |
| 17 | D | D | 18 | D | D |
| 19 | D | D | 20 | D | D |
| 21 | C | D | 22 | C | C |
| 23 | C | D | 24 | D | D |
| 25 | C | C | 26 | B | B |
| 27 | B | B | 28 | A | B |
| 29 | B | B | 30 | B | B |
| 31 | D | D | 32 | D | D |
| 33 | A | B | 34 | A | B |
| 35 | A | A | 36 | B | B |
| 37 | A | B | 38 | A | B |
| 39 | A | A | 40 | A | A |
| 41 | C | C | 42 | A | B |
| 43 | A | A | 44 | B | B |
| 45 | C | C | 46 | B | B |
| 47 | C | D | 48 | D | D |
| 49 | A | B | 50 | B | B |
| 51 | A | B | 52 | B | B |

HCV Polymerase Replicon Assay

Two stable subgenomic replicon cell lines were used for compound characterization in cell culture: one derived from genotype 1a-H77 and one derived from genotype 1b-Con1 (obtained from Apath, LLC, St. Louis, Mo.). All replicon constructs were bicistronic subgenomic replicons similar to those described by SCIENCE 285:110-3 (1999). The genotype 1a replicon construct contains NS3-NS5B coding region derived from the H77 strain of HCV (1a-H77) (J. VIROL. 77:3181-90 (2003)). The replicon also has a firefly luciferase reporter and a neomycin phosphotransferase (Neo) selectable marker. These two coding regions, separated by the FMDV 2a protease, comprise the first cistron of the bicistronic replicon construct, with the second cistron containing the NS3-NS5B coding region with addition of adaptive mutations E1202G, K1691R, K2040R and S2204I. The 1b-Con1 replicon construct is identical to the 1a-H77 replicon, except that the NS3-NS5B coding region was derived from the 1b-Con1 strain, and the adaptive mutations are E1202G, T1280I and S2204I. Replicon cell lines were maintained in Dulbecco's modified Eagles medium (DMEM) containing 10% (v/v) fetal bovine serum (FBS), 100 IU/mL penicillin, 100 mg/mL streptomycin (Invitrogen), and 200 mg/mL G418 (Invitrogen).

The inhibitory effects of compounds on HCV replication were determined by measuring activity of the luciferase reporter gene. Briefly, replicon-containing cells were seeded into 96 well plates at a density of 5000 cells per well in 100 μL DMEM containing 5% FBS. 16-24 hours later, the compounds were diluted in dimethyl sulfoxide (DMSO) to generate a 200× stock in a series of eight half-log dilutions. The dilution series was then further diluted 100-fold in the medium containing 5% FBS. Medium with the inhibitor was added to the overnight cell culture plates already containing 100 μL of DMEM with 5% FBS. In assays measuring inhibitory activity in the presence of human plasma, the medium from the overnight cell culture plates was replaced with DMEM containing 40% human plasma and 5% FBS. The cells were incubated for three days in the tissue culture incubators and were then lysed for RNA extraction. For the luciferase assay, 30 μL of Passive Lysis buffer (Promega)

was added to each well, and then the plates were incubated for 15 minutes with rocking to lyse the cells. Luciferin solution (50 to 100 μL, Promega) was added to each well, and luciferase activity was measured with a Victor II luminometer (Perkin-Elmer). The percent inhibition of HCV RNA replication was calculated for each compound concentration and the $EC_{50}$ value was calculated using nonlinear regression curve fitting to the 4-parameter logistic equation and GraphPad Prism 4 software.

When tested by the above method, the compounds of this invention inhibit HCV polymerase 1A and/or 1B. The legend in the table below is as follows: A—$EC_{50} \leq 0.01$ μM; B—$0.1$ μM$\geq EC_{50}>0.01$ μM; C—$1$ μM$\geq EC_{50}>0.1$ μM; and D—$EC_{50}>1$ μM; ND—not determined.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

SEQUENCE LISTING

```
<160> NUMBER OF SEQ ID NOS: 1

<210> SEQ ID NO 1
<211> LENGTH: 171
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 5' end
<220> FEATURE:
<221> NAME/KEY: misc_feature
<222> LOCATION: (171)..(171)
<223> OTHER INFORMATION: 3' end

<400> SEQUENCE: 1
gggcgaauug ggcccucuag augcaugcuc gagcggccgc cagugugaug gauaucugca      60
gaauucgccc uugguggcuc caucuuagcc cuagucacgg cuagcuguga aagguccgug     120
agccgcuuga cugcagagag ugcugauacu ggccucucug cagaucaagu c              171
```

TABLE EC$_{50}$

| compound | 1a | 1b | compound | 1a | 1b |
|---|---|---|---|---|---|
| 1 | ND | ND | 2 | B | A |
| 3 | A | A | 4 | A | A |
| 5 | D | D | 6 | C | A |
| 7 | B | A | 8 | C | B |
| 9 | A | A | 10 | C | D |
| 11 | ND | D | 12 | C | C |
| 13 | D | D | 14 | C | B |
| 15 | C | B | 16 | C | C |
| 17 | ND | ND | 18 | ND | ND |
| 19 | ND | ND | 20 | ND | ND |
| 21 | C | C | 22 | C | C |
| 23 | D | D | 24 | ND | ND |
| 25 | D | D | 26 | B | A |
| 27 | C | B | 28 | A | A |
| 29 | C | B | 30 | C | B |
| 31 | ND | ND | 32 | ND | ND |
| 33 | C | B | 34 | C | B |
| 35 | B | A | 36 | C | C |
| 37 | C | B | 38 | C | B |
| 39 | B | A | 40 | C | B |
| 41 | D | D | 42 | B | A |
| 43 | C | B | 44 | C | B |
| 45 | D | C | 46 | C | B |
| 47 | D | C | 48 | D | D |
| 49 | B | A | 50 | C | B |
| 51 | C | B | 52 | C | A |

We claim:

1. A compound or salt thereof, wherein:
the compound corresponds in structure to formula (I-L0):

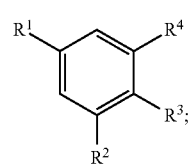

(I-L0)

$R^1$ is selected from the group consisting of:

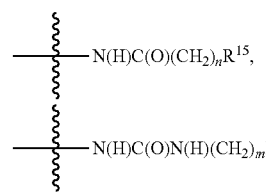

and benzoyl;
n is selected from the group consisting of 1, 2, and 3;
$R^{15}$ is selected from the group consisting of hydrogen, amino, and amino substituted with alkoxycarbonyl;
m is selected from the group consisting of 0, 1, 2, and 3;
$R^{16}$ is selected from the group consisting of hydrogen, aryl, alkyl, and alkyloxycarbonyl;
$R^2$ is selected from the group consisting of alkyl and 5-6-membered heterocyclyl, wherein:

(a) the alkyl optionally is substituted with one or more halo, and
(b) the heterocyclyl optionally is substituted with up to three substituents independently selected from the group consisting of alkyl and oxo;

$R^3$ is selected from the group consisting of alkyl, alkenyl, alkynyl, alkyloxy, alkenyloxy, alkynyloxy, amino, and halo;

$R^4$ is a fused 2-ring carbocyclyl optionally substituted with one or more substituents independently selected from the group consisting of $R^E$, $R^F$, and $R^J$;

each $R^E$ is independently selected from the group consisting of hydroxy and oxo;

each $R^F$ is $C_1$-$C_6$alkyl optionally substituted with one or more amino, wherein the amino optionally is substituted with one or two $C_1$-$C_6$alkylsulfonyl, wherein the amino portion of the alkylsulfonylamino optionally is substituted with $C_1$-$C_6$alkyl; and each $R^J$ is $C_1$-$C_6$alkylsulfonylamino.

2. The compound or salt of claim 1, wherein $R^1$ is

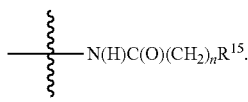

3. The compound or salt of claim 2, wherein n is 1.
4. The compound or salt of claim 2, wherein n is 2.
5. The compound or salt of claim 2, wherein $R^{15}$ is amino.
6. The compound or salt of claim 2, wherein $R^{15}$ is tert-butoxycarbonylamino.
7. The compound or salt of claim 1, wherein $R^1$ is

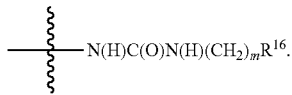

8. The compound or salt of claim 7, wherein m is 0.
9. The compound or salt of claim 7, wherein m is 2.
10. The compound or salt of claim 7, wherein $R^{16}$ is hydrogen.
11. The compound or salt of claim 7, wherein $R^{16}$ is phenyl.
12. The compound or salt of claim 7, wherein $R^{16}$ is $C_1$-$C_3$-alkyl.
13. The compound or salt of claim 7, wherein $R^{16}$ is $C_1$-$C_3$-alkyloxycarbonyl.
14. The compound or salt of claim 1, wherein $R^1$ is benzoyl.
15. The compound or salt of claim 1, wherein $R^2$ is selected from the group consisting of tert-butyl, perfluoroethyl, and trifluoromethyl.
16. The compound or salt of claim 1, wherein $R^2$ is selected from the group consisting of furanyl, pyrazolyl, and thiophenyl, wherein each such substituent optionally is substituted with methyl.
17. The compound or salt of claim 1, wherein $R^3$ is selected from the group consisting of $C_2$-$C_3$-alkenyl, $C_1$-$C_3$-alkyl, alkyloxy, amino, and halo.
18. The compound or salt of claim 1, wherein $R^3$ is methoxy.
19. The compound or salt of claim 1, wherein $R^4$ is selected from the group consisting of naphthalenyl, dihydronaphthalenyl, tetrahydronaphthalenyl, hexahydronaphthalenyl, octahydronaphthalenyl, decahydronaphthalenyl, indenyl, dihydroindenyl, hexahydroindenyl, octahydroindenyl, pentalenyl, octahydropentalenyl, and hexahydropentalenyl.

20. The compound or salt of claim 1, wherein:
$R^4$ is a fused 2-ring carbocyclyl selected from the group consisting of naphthalenyl, indenyl, and dihydroindenyl, wherein each such substituent is substituted with a substituent selected from the group consisting of $R^F$ and $R^J$;
$R^F$ is alkylsulfonylaminoalkyl; and
$R^J$ is alkylsulfonylamino.

21. A compound or salt thereof, wherein the compound is selected from the group consisting of
N-(6-(3-tert-butyl-5-(2,4-dioxo-1,2,3,4-tetrahydropyrimidin-5-yl)-4-methoxyphenyl)naphthalen-2-yl)methanesulfonamide;
N-(6-(3-tert-butyl-2-methoxy-5-ureidophenyl)naphthalen-2-yl)methanesulfonamide;
N-(6-(3-tert-butyl-2-methoxy-5-(3-phenylureido)phenyl) naphthalen-2-yl)methanesulfonamide;
N-(6-(3-tert-butyl-5-(3-isopropylureido)-2-methoxyphenyl) naphthalen-2-yl)methanesulfonamide;
tert-butyl 2-(3-tert-butyl-4-methoxy-5-(6-(methylsulfonamido) naphthalen-2-yl)phenylamino)-2-oxoethylcarbamate;
2-amino-N-(3-tert-butyl-4-methoxy-5-(6-(methylsulfonamido) naphthalen-2-yl)phenyl)acetamide;
ethyl 3-(3-(3-tert-butyl-4-methoxy-5-(6-(methylsulfonamido) naphthalen-2-yl)phenyl)ureido)propanoate;
N-(6-(3-tert-butyl-5-(3-ethylureido)-2-methoxyphenyl) naphthalen-2-yl)methanesulfonamide;
tert-butyl 3-(3-tert-butyl-4-methoxy-5-(6-(methylsulfonamido) naphthalen-2-yl)phenylamino)-3-oxopropylcarbamate;
3-amino-N-(3-tert-butyl-4-methoxy-5-(6-(methylsulfonamido) naphthalen-2-yl)phenyl)propanamide;
N-(6-(5-benzoyl-3-tert-butyl-2-methoxyphenyl)naphthalen-2-yl)methanesulfonamide;
(E)-N-(4-(5-benzoyl-3-tert-butyl-2-methoxystyryl)phenyl) methanesulfonamide;
(E)-N'-((3'-tert-butyl-5'-(2-(1,1-dioxidoisothiazolidin-2-yl))-2'methoxybiphenyl-4-yl)methylene)methanesulfonylhydrazide;
N-(3-tert-butyl-4-methoxy-5-(6-(methylsulfonamido) naphthalen-2-yl)phenyl)acetamide; and
(E)-N-(4-(5-(2,4-dioxo-1,2,3,4-tetrahydropyrimidin-5-yl)-2-methoxy-3-(trifluoromethyl)styryl)phenyl)methanesulfonamide.

22. A pharmaceutical composition comprising one or more compounds and/or salts recited in claim 1 and one or more excipients.

23. The pharmaceutical composition of claim 22, wherein the pharmaceutical composition further comprises one or more additional therapeutic agents.

24. A method for inhibiting replication of a hepatitis C virus, wherein the method comprises exposing the virus to one or more compounds and/or salts recited in claim 1.

25. A method for treating hepatitis C in a human in need of such treatment, wherein the method comprises administering to the human one or more compounds and/or salts recited in claim 1.

26. The method of claim 25, wherein the method further comprises administering to the human one or more additional therapeutic agents selected from the group consisting of an interferon agent, ribavirin, an HCV inhibitor, and an HIV inhibitor.

* * * * *